US008017601B2

(12) United States Patent
Kim et al.

(10) Patent No.: US 8,017,601 B2
(45) Date of Patent: Sep. 13, 2011

(54) BIS-ARYL KINASE INHIBITORS AND METHOD

(75) Inventors: Tae-Seong Kim, Thousands Oaks, CA (US); Jean-Christophe Harmange, Andover, MA (US); Steven Bellon, Wellesley, MA (US); Shon Booker, Thousand Oaks, CA (US); Noel D'Angelo, Thousand Oaks, CA (US); Celia Dominguez, Los Angeles, CA (US); Ingrid M. Fellows, Fresno, CA (US); Julie Germain, Medford, MA (US); Timothy S. Harvey, Thousand Oaks, CA (US); Joseph L. Kim, Wayland, MA (US); Matthew Lee, Calabasas, CA (US); Longbin Liu, Thousand Oaks, CA (US); Vinod F. Patel, Acton, MA (US); Andrew Tasker, Simi Valley, CA (US)

(73) Assignee: Amgen Inc., Thousand Oaks, CA (US)

( * ) Notice: Subject to any disclaimer, the term of this patent is extended or adjusted under 35 U.S.C. 154(b) by 1414 days.

(21) Appl. No.: 11/479,187

(22) Filed: Jun. 30, 2006

(65) Prior Publication Data
US 2007/0054903 A1    Mar. 8, 2007

Related U.S. Application Data

(60) Provisional application No. 60/696,389, filed on Jun. 30, 2005.

(51) Int. Cl.
C07D 403/02        (2006.01)
A61K 31/538        (2006.01)
(52) U.S. Cl. .................. 514/230.5; 514/232.8; 514/310; 514/314; 514/412; 544/126; 544/405; 546/148; 546/176; 548/360.1
(58) Field of Classification Search .................... None
See application file for complete search history.

(56) References Cited

U.S. PATENT DOCUMENTS 6,080,790 A * 6/2000 Boyd et al. ............. 514/650
6,518,257 B1 * 2/2003 Tasaka et al. ............ 514/63

FOREIGN PATENT DOCUMENTS

| EP | 0860433 A1 | 8/1998 |
| EP | 1411046 A1 | 4/2004 |
| EP | 1415987 A1 | 5/2004 |
| WO | WO 00/47212 A1 | 8/2000 |

OTHER PUBLICATIONS

Rosowsky et al., Antimicrobial Agents and Chemotherapy (1995), 39(1), pp. 79-86.*
Written Opinion of the International Search Authority for PCT/US2006/025699, 2007.*
Chemical Abstracts 132:315905, Takeuchi et al, JP 2000119653, 20000425, 114 pages.*
Jia, J. et al., "1-(2-Naphthyl)-1H-pyrazole-5-carboxylamides as potent factor Xa inhibitors. Part 2: A survey of P4 motifs", Bioorganic & Medicinal Chemistry Letter, 14 (5), 1221-1227, (2004).
Fischer-Durand et al., "Synthesis of 4-benzidinyl butyric acid: a key intermediate for antibodies production against benzidin", Synthetic Communications, 28 (6), 963-970, (1998).
Ten Have R. et al., "Novel Synthesis of 4(5)-Monosubstituted Imidazoles via Cycloaddition of Tosymethyl Isocyanide to Aldimines", Tetrahedron, Elsevier Science Publishers, Amsterdam, 53 (33), 11355-11368, (1997).
Mueller-Westerhoff et al., "The synthesis of dithiolene dyes with strong near-IR absorption", Tetrahydron, 47 (6), 909-932, (1991).
Okushima, H. et al., "A novel class of cardiotonics synthesis and pharmacological properties of 4-(substituted-amino)phenylpyridazinones and related derivatives", Journal of Medicinal Chemistry, American Chemical Society, Washington, 30 (7), 1157-1161, (1987).
Takahashi et al., "An efficient synthesis of 3-substituted pyrazoles by reaction of gamma, gamma-diethoxy-alpha-dimethylaminonitriles (masked beta-oxoaldehyde equivalents) with hydrazine dihydrochloride", Synthesis, 6/7, 690-691, (1985).
Ahlbrecht et al., "Diels-alder reaktionenmit 1,4-dimethyl-2,3-dimethylenhexahydropyrazin; ein einfacher weg zu octahydro- und tetrahydrozhinoxalinen", Synthesis, 3, 231-234, (1983).
Milton, J. Kornet at al., "Synthesis of alpha-methylenebutyrolactams as potential antitumor agents", Journal of Pharmaceutical Sciences, 68 (3), 350-353, (1979).
Sheinkman et al., "Reactions of cyclic ammonium cations, VII. Quinolination of 1-alkyl-2,3-dihydroindoles and 1-alkyl-1,2,3,4-tetrahydroquinolines", Chem, Heterocycl. Compd., 6, 1413-1419, (1970).
Sheinkman et al., "1-arylisoquinoline derivatives", U.S.S.R. From: Otkrytiya, Izobret., Prom. Obraztsy, Toyarnye Znaki, 46 (31), 30, (1969).
Bonnier et al., "Reactivite du 2-methyl naphthalene vis-à-vis radicaux libres phenyle", Tetrahedron Letters, 7, 627-630, (1967).
Nazarov et al., "Synthesis of steroid compounds and related substances, Communication 37. Synthesis of steroid analogs not containing a B ring", Izv. Akad. Nau k SSSR Ser, Khim, 567-572, (1956).
Hey and Lawton: "Synthesis of 2-phenylnaphthalenes", Journal of the Chemical Society, 374-383, (1940).
Avogadro et al., "Ricerche sulle diossime" Gazzetta Chimica Italiana, 53 (1), 698-707, (1923).

* cited by examiner

*Primary Examiner* — Zinna Northington Davis
(74) *Attorney, Agent, or Firm* — Olga Mekhovich

(57) ABSTRACT

Selected compounds are effective for prophylaxis and treatment of diseases, such as HGF mediated diseases. The invention encompasses novel compounds, analogs, prodrugs and pharmaceutically acceptable salts thereof, pharmaceutical compositions and methods for prophylaxis and treatment of diseases and other maladies or conditions involving, cancer and the like. The subject invention also relates to processes for making such compounds as well as to intermediates useful in such processes.

18 Claims, No Drawings

SEQUENCE LISTING

<160> NUMBER OF SEQ ID NOS: 2

<210> SEQ ID NO 1
<211> LENGTH: 39
<212> TYPE: DNA
<213> ORGANISM: Homo sapiens

<400> SEQUENCE: 1
attgacggat ccatgctaaa tccagagctg gtccaggca                     39

<210> SEQ ID NO 2
<211> LENGTH: 37
<212> TYPE: DNA
<213> ORGANISM: Homo sapiens

<400> SEQUENCE: 2
acaacagaat tcaatacgga gcgacacatt ttacgtt                       37

BIS-ARYL KINASE INHIBITORS AND METHOD

CROSS-REFERENCE TO RELATED APPLICATIONS

This application claims the benefit of U.S. Provisional Application No. 60/696,389 filed Jun. 30, 2005, which is incorporated herein by reference in its entirety.

FIELD OF THE INVENTION

This invention is in the field of pharmaceutical agents and specifically relates to compounds, compositions, uses and methods for treating inflammation, angiogenesis and cancer.

BACKGROUND OF THE INVENTION

Protein kinases represent a large family of proteins, which play a central role in the regulation of a wide variety of cellular processes, maintaining control over cellular function. A partial list of such kinases includes abl, Akt, bcr-abl, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

Certain diseases are known to be associated with deregulated angiogenesis, for example ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias).

At the center of the network regulating the growth and differentiation of the vascular system and its components, both during embryonic development and normal growth, and in a wide number of pathological anomalies and diseases, lies the angiogenic factor known as Vascular Endothelial Growth Factor" (VEGF; originally termed "Vascular Permeability Factor", VPF), along with its cellular receptors (see G. Breier et al., Trends in Cell Biology, 6:454-456 (1996)).

VEGF is a dimeric, disulfide-linked 46-kDa glycoprotein related to "Platelet-Derived Growth Factor" (PDGF); it is produced by normal cell lines and tumor cell lines; is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor"(PlGF) and VEGF-C.

VEGF receptors (VEGFR) are transmembranous receptor tyrosine kinases. They are characterized by an extracellular domain with seven immunoglobulin-like domains and an intracellular tyrosine kinase domain. Various types of VEGF receptor are known, e.g. VEGFR-1 (also known as flt-1), VEGFR-2 (also known as KDR), and VEGFR-3.

A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerates tumor growth. Increased VEGF expression could explain the occurrence of cerebral edema in patients with glioma. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants, which inhibited signal transduction, and with antisense-VEGF RNA techniques. All approaches led to a reduction in the growth of glioma cell lines or other tumor cell lines in vivo as a result of inhibited tumor angiogenesis.

Angiogenesis is regarded as an absolute prerequisite for tumors, which grow beyond a diameter of about 1-2 mm; up to this limit, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into avascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels. See R. Connell and J. Beebe, Exp. Opin. Ther. Patents, 11:77-114 (2001).

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production.

Inflammatory cytokines stimulate VEGF production. Hypoxia results in a marked up regulation of VEGF in numerous tissues, hence situations involving infarct, occlusion, ischemia, anemia, or circulatory impairment typically invoke VEGF/VPF-mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features. As such, regulators of angiogenesis have become an important therapeutic target.

The hepatocyte growth factor receptor ("c-Met") is a unique receptor tyrosine kinase shown to be overexpressed in a variety of malignancies. c-Met typically comprises, in its native form, a 190-kDa heterodimeric (a disulfide-linked 50-kDa α-chain and a 145-kDa β-chain) membrane-spanning tyrosine kinase protein (Proc. Natl. Acad. Sci. USA, 84:6379-6383 (1987)). c-Met is mainly expressed in epithelial cells and stimulation of c-Met leads to scattering, angiogenesis, proliferation and metastasis. (See Cytokine and Growth Factor Reviews, 13:41-59 (2002)).

The ligand for c-Met is hepatocyte growth factor (also known as scatter factor, HGF and SF). HGF is a heterodimeric protein secreted by cells of mesodermal origin (Nature, 327: 239-242 (1987); J. Cell Biol., 111:2097-2108 (1990)).

Various biological activities have been described for HGF through interaction with c-met (Hepatocyte Growth Factor-Scatter Factor (HGF-SF) and the c-Met Receptor, Goldberg and Rosen, eds., Birkhauser Verlag-Basel, 67-79 (1993). The biological effect of HGF/SF may depend in part on the target cell. HGF induces a spectrum of biological activities in epithelial cells, including mitogenesis, stimulation of cell motility and promotion of matrix invasion (Biochem. Biophys. Res. Comm., 122:1450-1459 (1984); Proc. Natl. Acad. Sci. U.S.A., 88:415-419 (1991)). It stimulates the motility and invasiveness of carcinoma cells, the former having been implicated in the migration of cells required for metastasis. HGF can also act as a "scatter factor", an activity that promotes the dissociation of epithelial and vascular endothelial cells (Nature, 327:239-242 (1987); J. Cell Biol., 111:2097-2108 (1990); EMBO J., 10:2867-2878 (1991); Proc. Natl. Acad. Sci. USA, 90:649-653 (1993)). Therefore, HGF is thought to be important in tumor invasion (Hepatocyte Growth Factor-Scatter Factor (HGF-SF) and the C-Met Receptor, Goldberg and Rosen, eds., Birkhauser Verlag-Basel, 131-165 (1993)).

HGF and c-Met are expressed at abnormally high levels in a large variety of solid tumors. High levels of HGF and/or c-Met have been observed in liver, breast, pancreas, lung, kidney, bladder, ovary, brain, prostate, gallbladder and myeloma tumors in addition to many others. The role of HGF/c-Met in metastasis has been investigated in mice using cell lines transformed with HGF/c-Met (J. Mol. Med., 74:505-513 (1996)). Overexpression of the c-Met oncogene has also been suggested to play a role in the pathogenesis and progression of thyroid tumors derived from follicular epithelium (Oncogene, 7:2549-2553 (1992)): HGF is a morphogen (Development, 110:1271-1284 (1990); Cell, 66:697-711 (1991)) and a potent angiogenic factor (J. Cell Biol., 119:629-641 (1992)).

Recent work on the relationship between inhibition of angiogenesis and the suppression or reversion of tumor progression shows great promise in the treatment of cancer (Nature, 390:404-407 (1997)), especially the use of multiple angiogenesis inhibitors compared to the effect of a single inhibitor. Angiogenesis can be stimulated by HGF, as well as vascular endothelial growth factor (VEGF) and basic fibroblast growth factor (bFGF).

Angiogenesis, the process of sprouting new blood vessels from existing vasculature and arteriogenesis, the remodeling of small vessels into larger conduit vessels are both physiologically important aspects of vascular growth in adult tissues. These processes of vascular growth are required for beneficial processes such as tissue repair, wound healing, recovery from tissue ischemia and menstrual cycling. They are also required for the development of pathological conditions such as the growth of neoplasias, diabetic retinopathy, rheumatoid arthritis, psoriasis, certain forms of macular degeneration, and certain inflammatory pathologies. The inhibition of vascular growth in these contexts has also shown beneficial effects in preclinical animal models. For example, inhibition of angiogenesis by blocking vascular endothelial growth factor or its receptor has resulted in inhibition of tumor growth and in retinopathy. Also, the development of pathological pannus tissue in rheumatoid arthritis involves angiogenesis and might be blocked by inhibitors of angiogenesis.

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Certain diseases are known to be associated with deregulated angiogenesis, for example ocular neovascularization, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias). Treatment of malaria and related viral diseases may also be mediated by HGF and cMet.

Elevated levels of HGF and c-Met have also been observed in non-oncological settings, such as hypertension, myocardial infarction and rheumatoid arthritis. It has been observed that levels of HGF increase in the plasma of patients with hepatic failure (Gohda et al., supra) and in the plasma (Hepatol., 13:734-750 (1991)) or serum (J. Biochem., 109:8-13 (1991)) of animals with experimentally induced liver damage. HGF has also been shown to be a mitogen for certain cell types, including melanocytes, renal tubular cells, keratinocytes, certain endothelial cells and cells of epithelial origin (Biochem. Biophys. Res. Commun., 176:45-51 (1991); Biochem. Biophys. Res. Commun., 174:831-838 (1991); Biochem., 30:9768-9780 (1991); Proc. Natl. Acad. Sci. USA, 88:415-419 (1991)). Both HGF and the c-Met protooncogene have been postulated to play a role in microglial reactions to CNS injuries (Oncogene, 8:219-222 (1993)).

In view of the role of HGF and/or c-Met in potentiating or promoting such diseases or pathological conditions, it would be useful to have a means of substantially reducing or inhibiting one or more of the biological effects of HGF and its receptor. Thus a compound that reduces the effect of HGF would be a useful compound.

T cells play a pivotal role in the regulation of immune responses and are important for establishing immunity to pathogens. In addition, T cells are often activated during inflammatory autoimmune diseases, such as rheumatoid arthritis, inflammatory bowel disease, type I diabetes, multiple sclerosis, Sjogren's disease, myasthenia gravis, psoriasis, and lupus. T cell activation is also an important component of transplant rejection, allergic reactions, and asthma.

T cells are activated by specific antigens through the T cell receptor (TCR), which is expressed on the cell surface. This activation triggers a series of intracellular signaling cascades mediated by enzymes expressed within the cell (Kane, L P et al. Current Opinion in Immunol. 200, 12, 242). These cascades lead to gene regulation events that result in the production of cytokines, like interleukin-2 (IL-2). IL-2 is a critical cytokine in T cell activation, leading to proliferation and amplification of specific immune responses.

One class of enzymes shown to be important in signal transduction is the kinase enzymes Members of the Src-family of tyrosine kinases include, for example: Lck, Fyn(B), Fyn(T), Lyn, Src, Yes, Hck, Fgr and Blk (for review see: Bolen, J B, and Brugge, J S Annu. Rev. Immunol 1997, 15, 371). Gene disruption studies suggest that inhibition of some members of the src family of kinases would potentially lead to therapeutic benefit. Src(−/−) mice have abnormalities in bone remodeling or osteopetrosis (Soriano, P. Cell 1991, 64, 693), suggesting that inhibition of this kinase might be useful in diseases of bone resorption, such as osteoporosis. Lck(−/−)

mice have defects in T cell maturation and activation (Anderson, S J et al. Adv. Immunol. 1994, 56, 151), suggesting that inhibition of this kinase might be useful in diseases of T cell mediated inflammation. In addition, human patients have been identified with mutations effecting Lck kinase activity (Goldman, F D et al. J. Clin. Invest. 1998, 102, 421). These patients suffer from a severe combined immunodeficiency disorder (SCID).

Without wishing to imply that the compounds disclosed in the present invention possess pharmacological activity only by virtue of an effect on a single biological process, it is believed that the compounds modulate T cell activation by way of inhibition of one or more of the multiple protein tyrosine kinases involved in early signal transduction steps leading to T cell activation, for example by way of inhibition of Lck kinase.

Src-family kinases are also important for signaling downstream of other immune cell receptors. Fyn, like Lck, is involved in TCR signaling in T cells (Appleby, M W et al. Cell 1992, 70, 751). Hck and Fgr are involved in Fcγ receptor signaling leading to neutrophil activation (Vicentini, L. et al. J. Immunol. 2002, 168, 6446). Lyn and Src also participate in Fcγ receptor signaling leading to release of histamine and other allergic mediators (Turner, H. and Kinet, J-P Nature 1999, 402, B24). These findings suggest that Src family kinase inhibitors may be useful in treating allergic diseases and asthma.

PCT publication WO 03/000660 describes substituted phenyl compounds. Substituted quinolines are described in U.S. Pat. No. 6,143,764. WO 02/32872 describes substituted quinolines. WO 00/47212 describes substituted quinazoline derivatives.

Compounds of the current invention have not been described for the treatment of cancer and inflammation.

DESCRIPTION OF THE INVENTION

A class of compounds useful in treating cancer and angiogenesis is defined by Formula 1

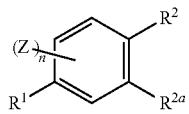

1 including enantiomers, diastereomers, salts, solvates and N-oxides thereof
wherein
j is one to six;
n and m are each independently zero to three;
p at each occurancwe is independently zero to six;
q is zero to four;
t is zero, 1 one two;
$R^1$ is an aryl ring system or a 5-14-membered nitrogen containing heteroaryl or heterocyclyl ring system; any of which may be optionally independently substituted with 1 to 4 Z groups;

$R^2$ is

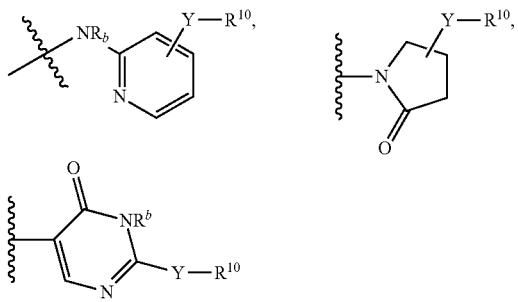

—$NR^aR^b$, or —Y—$R^{10}$;
$R^{2a}$ is hydrogen or Z;
or alternatively, $R^2$ and $R^{2a}$ together with the respective phenyl ring carbon atoms to which they are each bonded combine to form one of the following ring systems:

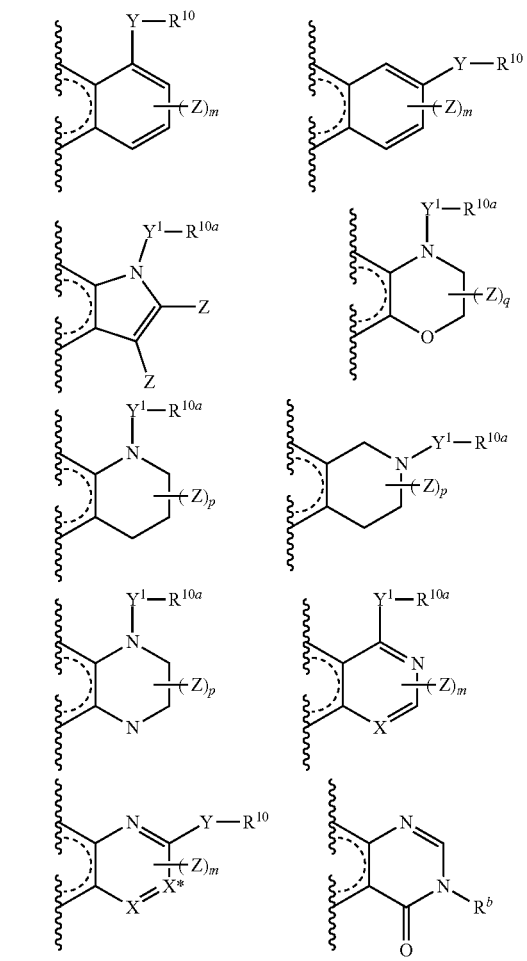

X is C or N;
X* is C or N provided X* is not N when X is N;
Y is selected from —$NR^b(CR^3R^4)_p$—, —$NR^bC(=O)(CR^3R^4)_p$—, —$NR^bC(=O)NR^b(CR^3R^4)_p$—, —$NR^bC(=O)NR^b(CR^3R^4)_p$—, —$NR^bC(=O)(CR^3R^4)_pO$—, —$NR^bC(=O)O(CR^3R^4)_p$—, —$NR^bC(=S)(CR^3R^4)_pO$—, —$NR^bC(=S)$—$NR^b(CR^3R^4)_p$—, —$NR^bC(=S)$—

NR$^b$—C(=O)(CR$^3$R$^4$)$_p$—, —NR$^b$C(=NR$^a$)(CR$^3$R$^4$)$_p$—, —NR$^b$SO$_2$—(CR$^3$R$^4$)$_p$—, —OC(=O)(CR$^3$R$^4$)$_p$—, —O(CR$^3$R$^4$)$_p$—, —(CR$^3$R$^4$)$_p$—S(=O)$_t$—, —(CR$^3$R$^4$)$_p$—, —S(=O)$_2$NR$^b$(CR$^3$R$^4$)$_p$—, —S(=O)$_t$(CR$^3$R$^4$)$_p$—, —C(=O)(CR$^3$R$^4$)$_p$—, —C(=O)—O—(CR$^3$R$^4$)$_p$—, —C(=NR$^a$)NH(CR$^3$R$^4$)$_p$—, —C(=S)NH(CR$^3$R$^4$)$_p$— and —C(=O)NH(CR$^3$R$^4$)$_p$—; wherein Y is in either direction;

Y$^1$ is selected from —NR$^b$(CR$^3$R$^4$)$_p$—, —NR$^b$C(=O)(CR$^3$R$^4$)$_p$—, —NR$^b$C(=O)NR$^b$(CR$^3$R$^4$)$_p$—, —NR$^b$C(=O)O(CR$^3$R$^4$)$_j$—, —NR$^b$C(=S)(CR$^3$R$^4$)$_p$—, —NR$^b$C(=NR$^a$)(CR$^3$R$^4$)$_p$—, —NR$^b$SO$_2$—(CR$^3$R$^4$)$_p$, —(CR$^3$R$^4$)$_p$—S(=O)$_t$—, —(CR$^3$R$^4$)$_p$—, —S(=O)$_2$NR$^b$(CR$^3$R$^4$)$_p$—, —S(=O)$_t$(CR$^3$R$^4$)$_p$—, —C(=O)(CR$^3$R$^4$)$_p$—, —C(=NR$^a$)NH(CR$^3$R$^4$)$_p$—, —C(=S)NH(CR$^3$R$^4$)$_p$— and —C(=O)NH(CR$^3$R$^4$)$_p$—; wherein Y is in either direction;

R$^a$ and R$^b$ is each independently selected from H, alkyl, heterocyclyl, aryl, arylalkyl, heterocyclylalkyl, cycloalkyl, cycloalkylalkyl, alkenyl, alkynyl, R$^5$R$^5$N—(C=O)—, and R$^5$—(=O)—; wherein each of R$^a$ and R$^b$ is optionally substituted;

R$^3$ and R$^4$ is each independently selected from H, alkyl, aryl, heterocyclyl, arylalkyl, heterocyclylalkyl, haloalkyl, cycloalkyl, cycloalkylalkyl, R$^6$ and alkyl substituted with R$^6$;

R$^5$ at each occurrence is independently selected from H, alkyl, cycloalkyl, haloalkyl, arylalkyl, heteroarylalkyl, heterocycloalkyl, cycloalkylalkyl, aryl, heteroaryl, heterocyclyl, alkenyl, and alkynyl;

R$^6$ is selected from cyano, —OR$^9$, —SR$^9$, halo, —SO$_2$R$^9$, —C(=O)R$^9$, —SO$_2$NR$^9$R$^5$, —NR$^5$C(=O)OR$^9$, —NR$^5$C(=O)NR$^5$R$^9$, —NR$^5$C(=O)R$^9$, —CO$_2$R$^9$, —C(=O)NR$^9$R$^5$ and —NR$^9$R$^5$;

R$^7$, R$^{7a}$ and R$^8$ are independently H, alkyl, cycloalkyl, haloalkyl, arylalkyl, heteroarylalkyl, heterocycloalkyl, cycloalkylalkyl, aryl, heteroaryl, heterocyclyl, alkenyl, and alkynyl;

or R$^7$ and R$^8$ together with the nitrogen atom to which they are bonded combine to form a 5-10 membered heterocylo or heteroaryl ring, either of which may be optionally substituted with 1 to 4 Z groups;

R$^9$ at each occurance is independently
i) H; or
ii) alkyl, cycloalkyl, haloalkyl, arylalkyl, heteroarylalkyl, heterocycloalkyl, cycloalkylalkyl, aryl, or heteroaryl any of which may be optionally substituted with 1 or more Z groups;

R$^{10}$ and R$^{10a}$ are independently
i) H; or
ii) aryl, heteroaryl, heterocyclyl, cycloalkyl, cycloalkenyl, alkyl, alkenyl or alkynyl any of which may be optionally substituted with one or more Z groups;

Z at each occurance is independently selected from independently selected from cyano, hydroxy, halogen, alkyl, haloalkyl, oxo, amino, —OR$^9$, —NR$^{7a}$-(alkyl)-NR$^7$R$^8$, —NR$^{7a}$-(alkyl)-OR$^9$, —N(C=O)—NR$^7$R$^8$, —C(=O)NR$^7$R$^8$, Preferred compounds of Formula I include compounds of the following Formulae II, III and IV

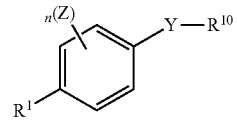

II

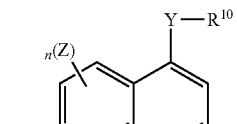

III

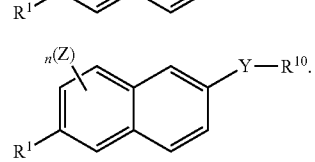

IV

Preferred R$^1$ groups for compounds of Formula I, II, III and IV include the following (shown with optional substituents Z$^1$ and Z$^2$):

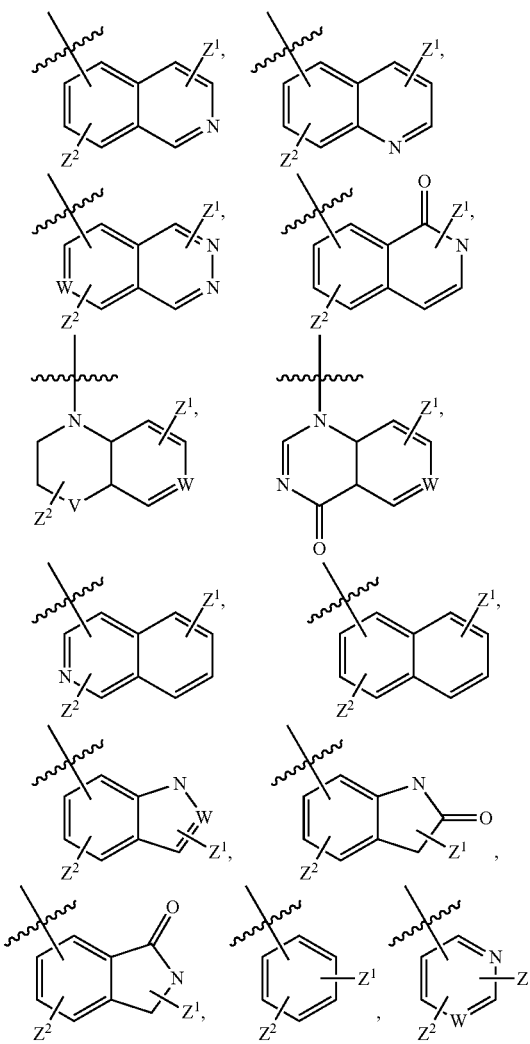

where W is C or N; and
V is C, O or N.

More preferred R¹ groups include:

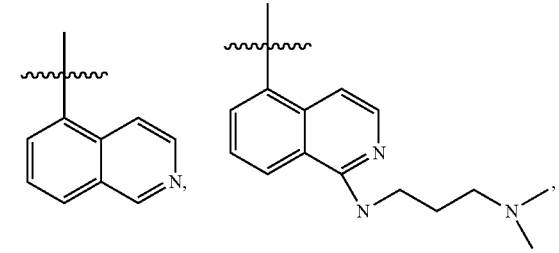
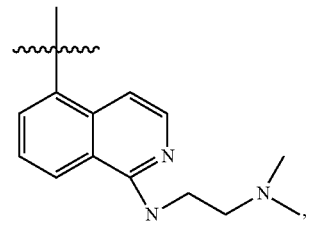
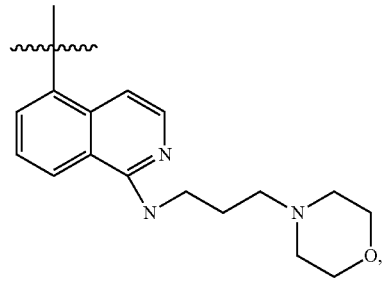
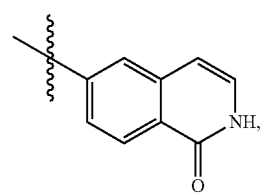
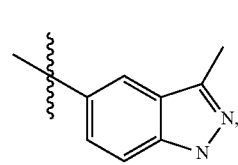
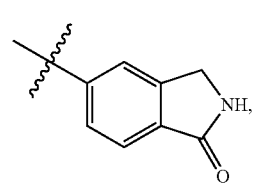

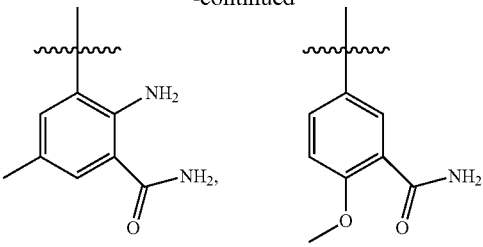

Preferred Y groups for compounds of Formula I, II, III and IV include the following:

—NR$^b$(CR$^3$R$^4$)$_p$—,

—NR$^b$C(=O)(CR$^3$R$^4$)$_p$—,

—NR$^b$C(=O)NR$^b$(CR$^3$R$^4$)$_p$—,

—(CR$^3$R$^4$)$_p$—,

—C(=O)(CR$^3$R$^4$)$_p$—,

—C(=O)NH(CR$^3$R$^4$)$_p$—

—C(=O)—O—(CR$^3$R$^4$)$_p$—,

—NR$^b$C(=S)—NR$^b$(CR$^3$R$^4$)$_p$—

Preferred R¹⁰ groups for compounds of Formula I, II, III and IV include phenyl, thiazolyl, and thienyl any of which may be optionally substituted with one or more Z groups.

Preferred compounds of Formulae II, III and IV include compounds of the following Formulae IIa, IIIa and IVa

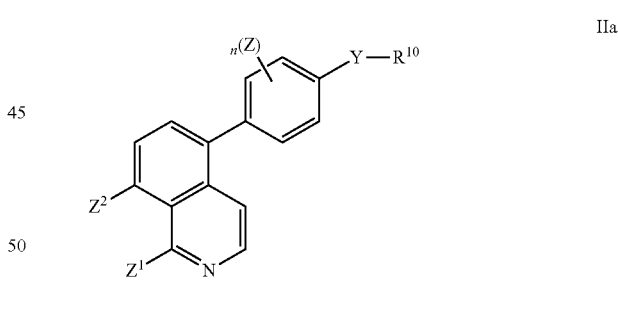

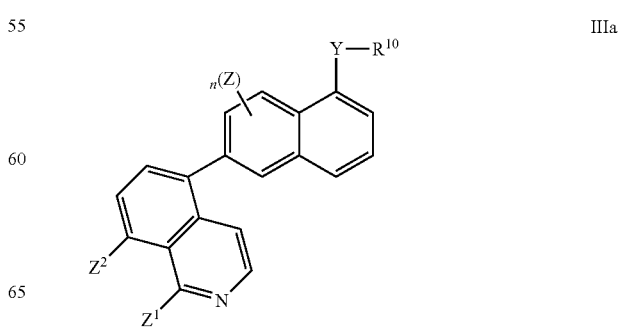

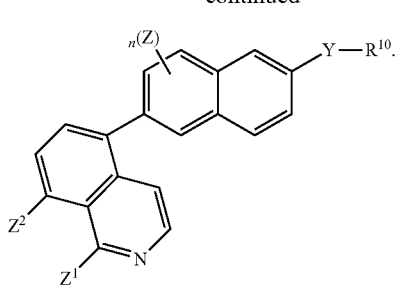

Although the pharmacological properties of the compounds of Formulas I-VII vary with structural change, in general, activity possessed by compounds of Formulas I-VII may be demonstrated in vivo. The pharmacological properties of the compounds of this invention may be confirmed by a number of pharmacological in vitro assays. The exemplified pharmacological assays, which follow, have been carried out with the compounds according to the invention and their salts. Compounds of the present invention showed inhibition of Lck kinase at doses less than 10 µM. Compounds of the present invention showed inhibition of c-Met kinase at doses less than 10 µM. Compounds of the present invention also showed inhibition of VEGFR kinase at doses less than 10 µM.

Indications

Compounds of the present invention would be useful for, but not limited to, the prevention or treatment of angiogenesis related diseases. The compounds of the invention have kinase inhibitory activity, such as VEGFR/KDR, c-kit, abl, and/or c-Met inhibitory activity. The compounds of the invention are useful in therapy as antineoplasia agents or to minimize deleterious effects of VEGF and/or HGF. The compounds of the invention also inhibit lck and src activity.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer *Helicobacter* related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of sub-cutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of diabetic conditions such as diabetic retinopathy and microangiopathy.

Accordingly, the invention relates to a method of treating inflammation in a mammal, the method comprising administering to the mammal a therapeutically effective amount of a compound according to any one of the above embodiments.

The invention relates to a method of inhibiting T cell activation in a mammal, the method comprising administering to the mammal a therapeutically effective amount of a compound according to any one of the above embodiments.

The invention relates to a method of treating arthritis, rheumatoid arthritis, psoriatic arthritis, or osteoarthritis in a mammal, the method comprising administering to the mammal a therapeutically effective amount of a compound according to any one of the above embodiments.

The invention relates to a method of treating organ transplant, acute transplant or heterograft or homograft rejection, or transplantation tolerance induction in a mammal, the method comprising administering to the mammal a therapeutically effective amount of a compound according to any one of the above embodiments.

The invention relates to a method of treating ischemic or reperfusion injury, myocardial infarction, or stroke in a mammal, the method comprising administering to the mammal a therapeutically effective amount of a compound according to any one of the above embodiments.

The compounds of this invention may also act as inhibitors of other protein kinases, e.g. tie-2, lck, src, fgf, c-Met, ron, and ret, and thus be effective in the treatment of diseases associated with other protein kinases. The compounds of this invention may also act as inhibitors of mutants of the above-identified tyrosine kinases, including c-kit, abl and VEGFR.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Where the plural form is used for compounds, salts, and the like, this is taken to mean also a single compound, salt and the like.

DEFINITIONS

"Angiogenesis" is defined as any alteration of an existing vascular bed or the formation of new vasculature, which benefits tissue perfusion. This includes the formation of new vessels by sprouting of endothelial cells from existing blood vessels or the remodeling of existing vessels to alter size, maturity, direction or flow properties to improve blood perfusion of tissue.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, the terms "hepatocyte growth factor" and "HGF" refer to a growth factor typically having a structure with six domains (finger, Kringle 1, Kringle 2, Kringle 3, Kringle 4 and serine protease domains). Fragments of HGF constitute HGF with fewer domains and variants of HGF may have some of the domains of HGF repeated; both are included if they still retain their respective ability to bind a HGF receptor. The terms "hepatocyte growth factor" and "HGF" include hepatocyte growth factor from humans ("huHGF") and any non-human mammalian species, and in particular rat HGF.

The terms as used herein include mature, pre, pre-pro, and pro forms, purified from a natural source, chemically synthesized or recombinantly produced. Human HGF is encoded by the cDNA sequence published by Miyazawa et al. (1989), supra, or Nakamura et al. (1989), supra. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms. It will be understood that natural allelic variations exist and can occur among individuals, as demonstrated by one or more amino acid differences in the amino acid sequence of each individual. The terms "hepatocyte growth factor" and "HGF" specifically include the delta 5 huHGF as disclosed by Seki et al., supra.

The terms "HGF receptor" and "c-Met" when used herein refer to a cellular receptor for HGF, which typically includes an extracellular domain, a transmembrane domain and an intracellular domain, as well as variants and fragments thereof which retain the ability to bind HGF. The terms "HGF receptor" and "c-Met" include the polypeptide molecule that comprises the full-length, native amino acid sequence encoded by the gene variously known as $p^{190}$MET. The present definition specifically encompasses soluble forms of HGF receptor, and HGF receptor from natural sources, synthetically produced in vitro or obtained by genetic manipulation including methods of recombinant DNA technology. The HGF receptor variants or fragments preferably share at least about 65% sequence homology, and more preferably at least about 75% sequence homology with any domain of the human c-Met amino acid sequence published in Rodrigues et al., Mol. Cell. Biol., 11:2962-2970 (1991); Park et al., Proc. Natl. Acad. Sci., 84:6379-6383 (1987); or Ponzetto et al., Oncogene, 6:553-559 (1991).

The terms "agonist" and "agonistic" when used herein refer to or describe a molecule which is capable of, directly or indirectly, substantially inducing, promoting or enhancing HGF biological activity or HGF receptor activation.

The terms "cancer" and "cancerous" when used herein refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by increased levels of HGF or expression of c-Met in the mammal.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

Given that elevated levels of c-Met and HGF are observed in hypertension, arteriosclerosis, myocardial infarction, and rheumatoid arthritis, nucleic acid ligands will serve as useful therapeutic agents for these diseases.

The term "treatment" includes therapeutic treatment as well as prophylactic treatment (either preventing the onset of disorders altogether or delaying the onset of a pre-clinically evident stage of disorders in individuals).

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" embraces bridging divalent alkyl radicals such as methylenyl and ethylenyl. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, amino, alkoxy and lower alkylamino. Phenyl substituted with —O—CH$_2$—O— forms the aryl benzodioxolyl substituent.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term heterocyclyl also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heterocyclyl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —SO$_2$—.

The terms "sulfamyl," "aminosulfonyl" and "sulfonamidyl," denotes a sulfonyl radical substituted with an amine radical, forming a sulfonamide (—SO$_2$NH$_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "aminocarbonyl" denotes an amide group of the formula —C(=O)NH$_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S—$).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups, which have been substituted with one or two aryl radicals, such as N-phenylamino. The arylamino radicals may be further substituted on the aryl ring portion of the radical.

The term "heteroarylamino" denotes amino groups, which have been substituted with one or two heteroaryl radicals, such as N-thienylamino. The "heteroarylamino" radicals may be further substituted on the heteroaryl ring portion of the radical.

The term "aralkylamino" denotes amino groups, which have been substituted with one or two aralkyl radicals. More preferred are phenyl-$C_1$-$C_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups, which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "cycloalkyl" includes saturated carbocyclic groups. Preferred cycloalkyl groups include $C_3$-$C_6$ rings. More preferred compounds include, cyclopentyl, cyclopropyl, and cyclohexyl.

The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Even more preferred are "5-6-membered cycloalkylalkyl" attached to alkyl portions having one to three carbon atoms. Examples of such radicals include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The term "Formulas I-IV" includes any sub formulas.

The compounds of the invention are endowed with kinase inhibitory activity, such as Lck, KDR VEGF and/or c-Met inhibitory activity.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of Lck, KDR VEGF and/or c-Met.

The present invention comprises a pharmaceutical composition comprising a therapeutically-effective amount of a compound of Formulas I-VII in association with a least one pharmaceutically-acceptable carrier, adjuvant or diluent.

The present invention also comprises a method of treating angiogenesis related disorders in a subject having or susceptible to such disorder, the method comprising treating the subject with a therapeutically-effective amount of a compound of Formula Combinations While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents, which may be used in combination with compounds of the present invention, consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents, which may be used in combination with compounds of the present invention, consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibringen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SR1 International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICU-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit anti-thymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other agents, such as other kinase inhibitors including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors, and anti-inflammatories.

The present invention comprises processes for the preparation of a compound of Formula I-IV.

Also included in the family of compounds of Formula I-IV are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I-VII may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I-VII include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I-VII. When a basic group and an acid group are present in the same molecule, a compound of Formula I-VII may also form internal salts.

General Synthetic Procedures

The compounds of the invention can be synthesized according to the following procedures of Schemes 1-16, wherein the substituents are as defined for Formulas I-VII, above, except where further noted.

The following abbreviations are used throughout the specification:

| | |
|---|---|
| AcOH | acetic acid |
| BINAP | 2,2'-bis(diphenylphosphino)-1,1'-binapthyl |
| BBr₃ | boron tribromide |
| BH₃—THF | borane-tetrahydrofuran complex |
| BOC | t-butoxycarbonyl |
| BSA | bovine serum albumin |
| n-BuLi | n-butyl lithium |
| CO | carbon monoxide |
| C₂O₂Cl₂ or (COCl)₂ | oxalyl chloride |
| Cs₂CO₃ | cesium carbonate |
| CHCl₃ | chloroform |
| Et₂O | diethyl ether |
| DCM, CH₂Cl₂ | methylene chloride |
| DIBAL | diisobutylaluminum hydride |
| DIEA, DIPEA, Hunig's base | diisopropylethylamine |
| DMF | dimethylformamide |
| dppa | diphenylphosphoryl azide |
| DPPP | 1,3-diphenylphosphino propane |
| DMAP | 4-dimethylaminopyridine |
| EtOAc, EA | ethyl acetate |

-continued

| | |
|---|---|
| EtOH | ethanol |
| Et₂O | diethyl ether |
| EDC, EDCI | 1-(3-dimethylaminopropyl)-3-ethylcarbodiimide hydrochloride |
| EtNH₂ | ethyl amine |
| FBS | fetal bovine serum |
| g | gram |
| h | hour |
| HCl | hydrochloric acid |
| HOAt | 1-hydroxy-7-azabenzotriazole |
| HOBt | 1-hydroxybenzotriazole hydrate |
| H₂ | hydrogen |
| H₂0 | water |
| H₂O₂ | hydrogen peroxide |
| HATU | O-(7-azabenzotriazol-1-yl-)N,N,N',N',tetramethyluronium hexafluorophosphate |
| KOH | potassium hydroxide |
| K₂CO₃ | potassium carbonate |
| K₃PO₄ | potassium phosphate |
| KMnO₄ | potassium permanganate |
| LAH | lithium aluminum hydride |
| LiHMDS | lithium bis(trimethylsilyl)-amide |
| LiOH | lithium hydroxide |
| MgSO₄ | magnesium sulfate |
| MCPBA | meta-chloroperbenzoic acid |
| MeOH, CH₃OH | methanol |
| MeNH₂ | methyl amine |
| NH₄Cl | ammonium chloride |
| NH₄OH | ammonium hydroxide |
| NMP | N-methylpyrrolidinone |

-continued

| | |
|---|---|
| NaHCO₃ | sodium bicarbonate |
| NaN₃ | sodium azide |
| Na₂SO | sodium sulfate |
| NaOH | sodium hydroxide |
| NaH | sodium hydride |
| Na₂SO₄ | sodium sulfate |
| NaOt-Bu | sodium tert-butoxide |
| NaHB(OAc)₃ | sodium triacetoxyborohydride |
| N₂ | nitrogen |
| O/N | overnight |
| POCl₃ | phosphorus oxychloride |
| Pd/C | palladium on carbon |
| Pd₂(dba)₃ | bis(dibenzylideneacetone) palladium |
| Pd(OAC)₂ | palladium (II) acetate |
| P(t-bu)₃ | tri(tert-butyl)phosphine |
| PBS | phospate buffered saline |
| PyBop | Benzotriazol-1-yl-oxy-tripyrrolidino-phosphonium hexafluorophosphate |
| RT | room temperature |
| SOCl₂ | thionyl chloride |
| TBTU | O-benzotriazol-1-yl-N,N,N',N'-tetramethyluronium tetrafluoroborate |
| TBAI | tetrabutylammonium iodide |
| TFA | trifluoroacetic acid |
| THF | tetrahydrofuran |
| TEA, Et₃N | triethylamine |

Examples

| Ex. | Structure | MW | Mass (M + 1) |
|---|---|---|---|
| 1 | 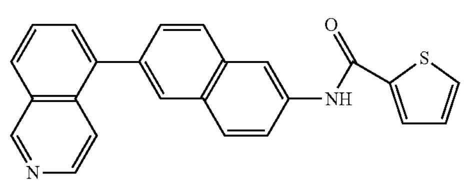 | 380 | 381 |
| 2 | 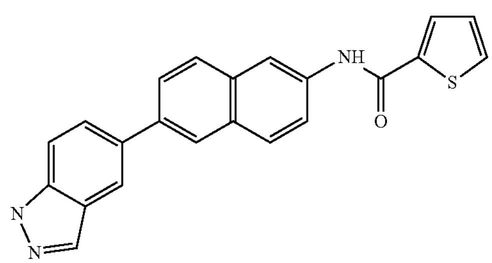 | 369 | 370 |
| 3 | 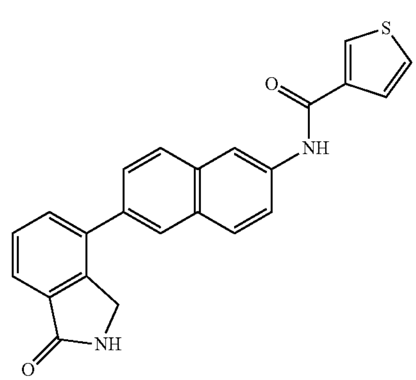 | 384 | 385 |

-continued

| Ex. | Structure | MW | Mass (M + 1) |
|---|---|---|---|
| 4 | 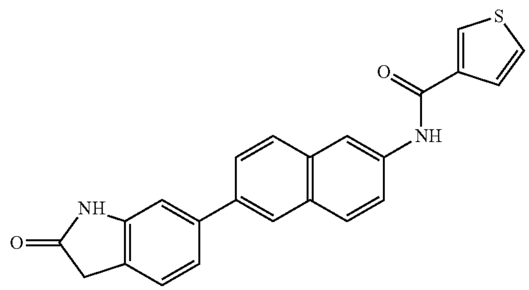 | 384 | 385 |
| 5 | 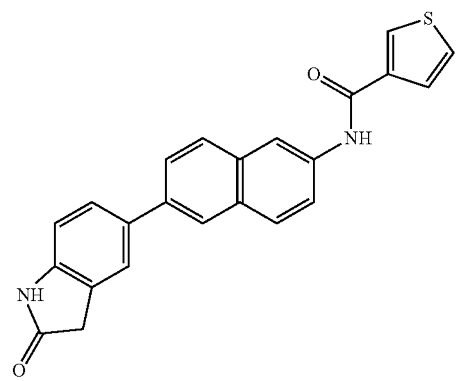 | 384 | 385 |
| 6 | 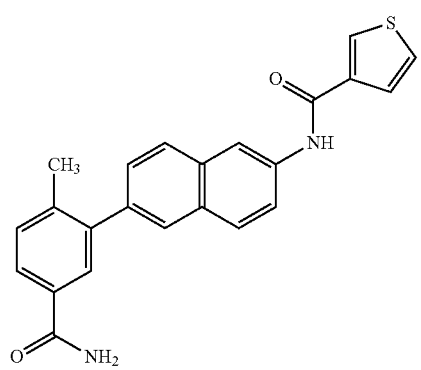 | 386 | 387 |
| 7 | 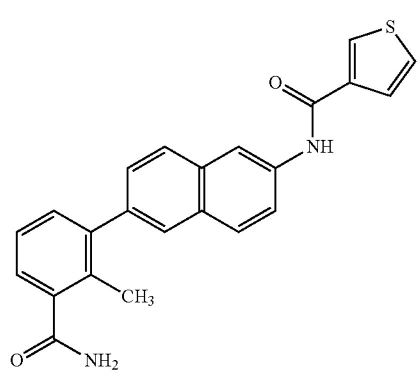 | 386 | 387 |

-continued

| Ex. | Structure | MW | Mass (M + 1) |
|---|---|---|---|
| 8 | 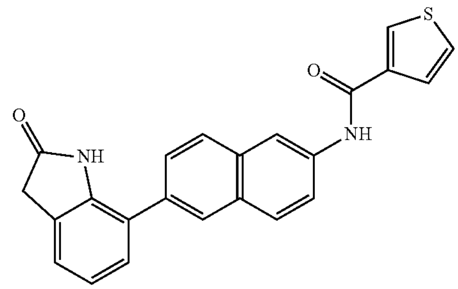 | 384 | 385 |
| 9 | 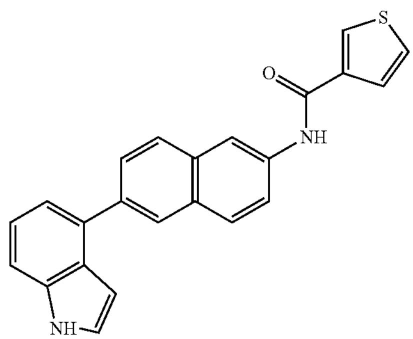 | 368 | 369 |
| 10 | 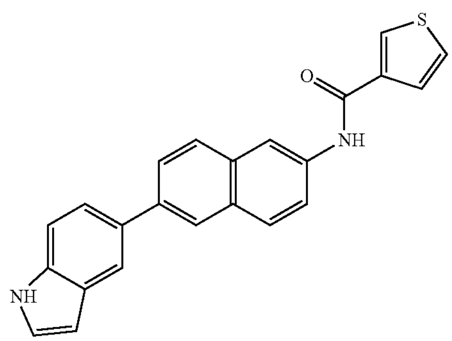 | 368 | 369 |
| 11 | 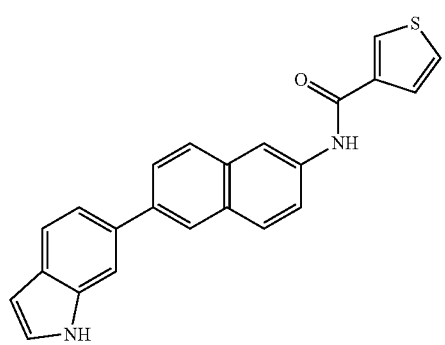 | 368 | 369 |
| 12 | 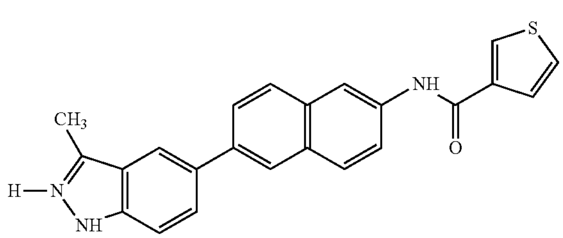 | 383 | 384 |

-continued

| Ex. | Structure | MW | Mass (M + 1) |
|---|---|---|---|
| 13 | 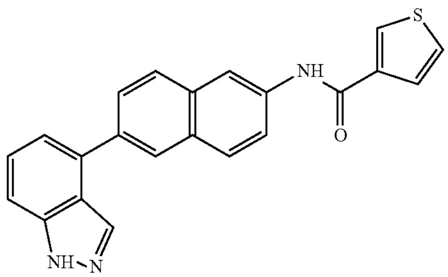 | 369 | 370 |
| 14 | 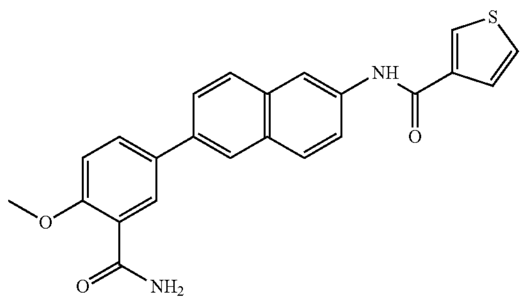 | 402 | 403 |
| 15 | 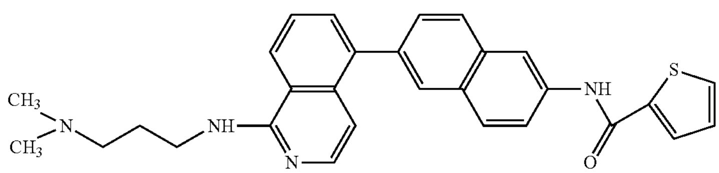 | 481 | 482 |
| 16 | 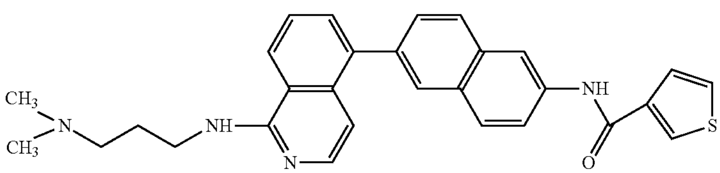 | 481 | 482 |
| 17 | 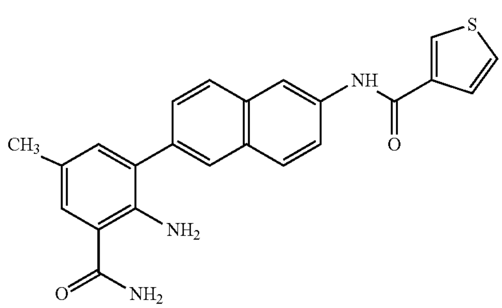 | 401 | 402 |
| 18 | 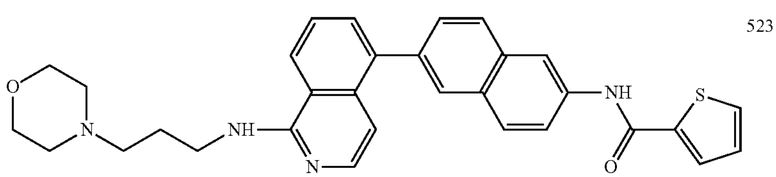 | 523 | 524 |
| 19 | 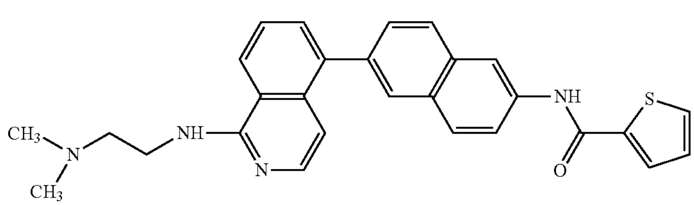 | 467 | 468 |

-continued

| Ex. | Structure | MW | Mass (M + 1) |
|---|---|---|---|
| 20 | 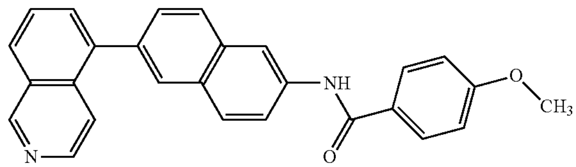 | 404 | 405 |
| 21 | 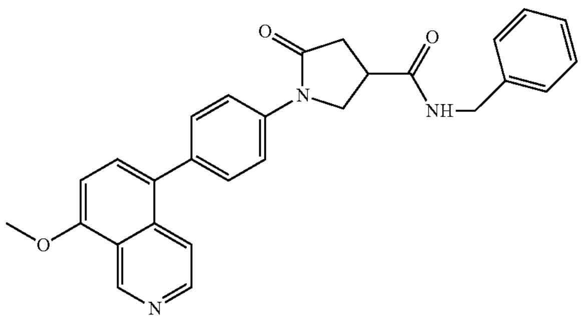 | 451 | 452 |
| 22 | 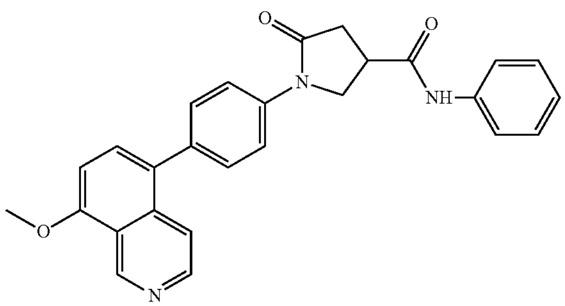 | 437 | 438 |
| 23 | 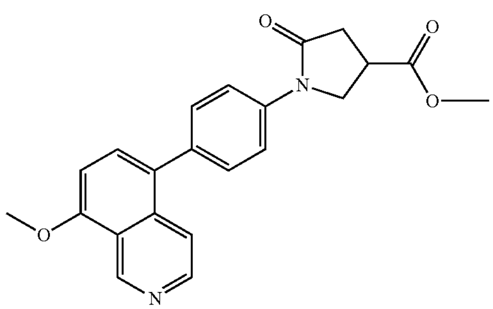 | 376 | 377 |
| 24 | 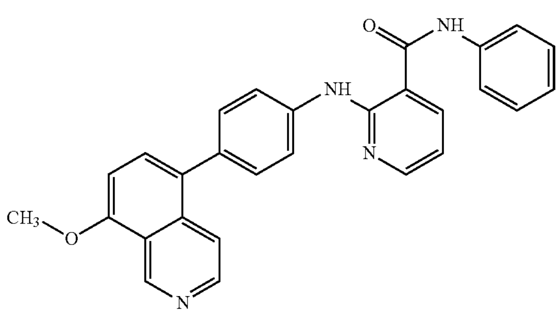 | 447 | 448 |

| Ex. | Structure | MW | Mass (M + 1) |
|---|---|---|---|
| 25 | 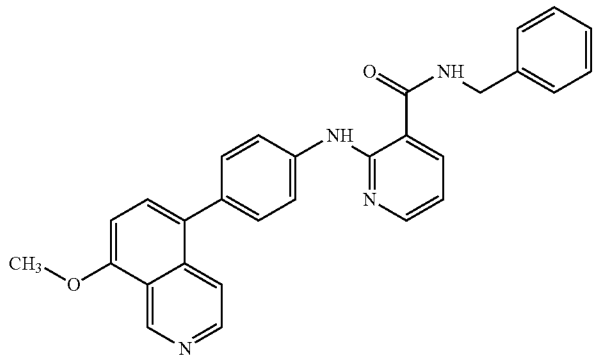 | 461 | 462 |
| 26 | 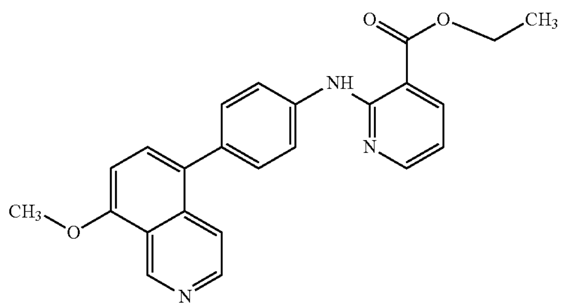 | 399 | 400 |
| 27 | 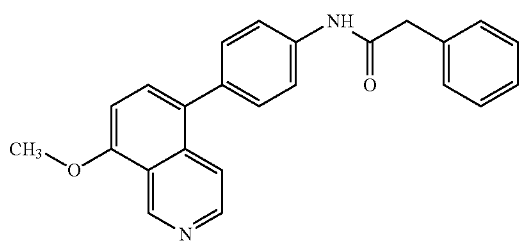 | 368 | 369 |
| 28 | 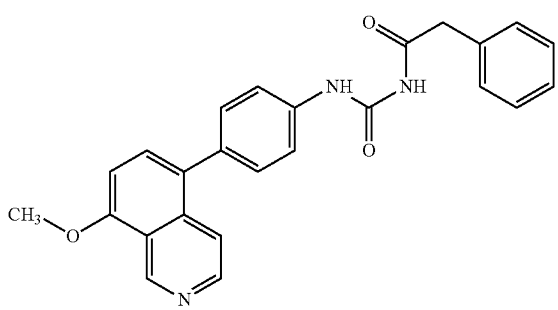 | 428 | 429 |
| 29 | 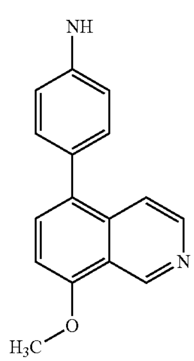 | 250 | 251 |

-continued

| Ex. | Structure | MW | Mass (M + 1) |
|---|---|---|---|
| 30 | 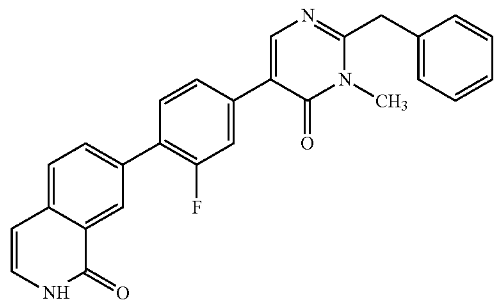 | 437 | 438 |
| 31 | 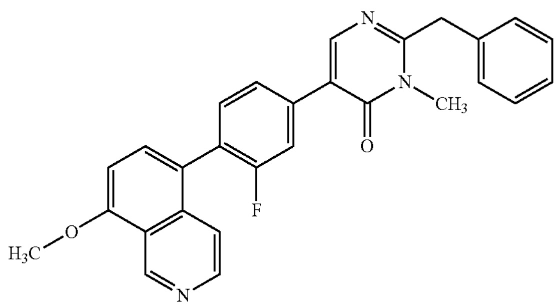 | 451 | 452 |
| 32 | 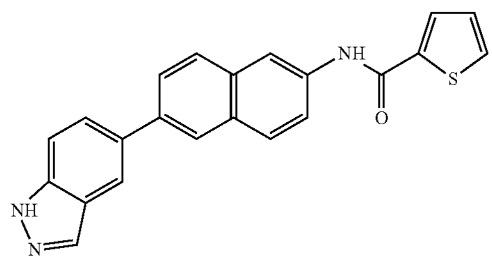 | 369 | 370 |

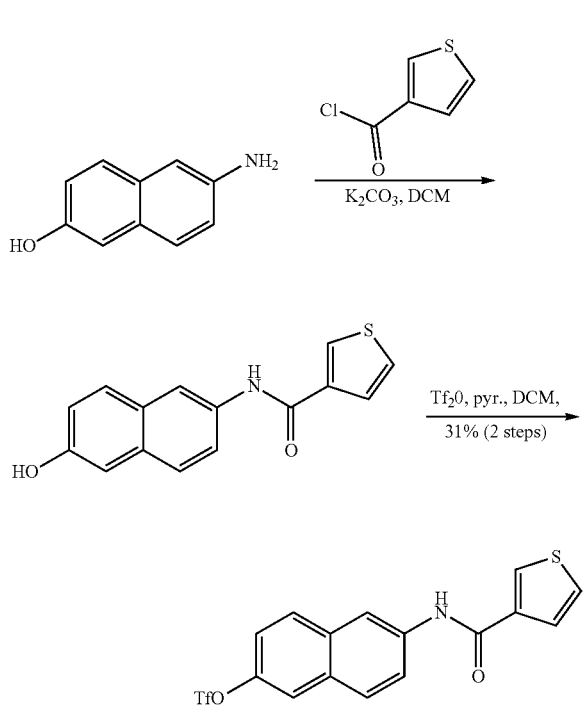

6-(thiophene-4-carboxamido)naphthalen-2-yl trifluoromethanesulfonate

The hydrochloride salt of 6-aminonaphthalen-2-ol (3.93 g, 20.1 mmol) and $K_2CO_3$ (9.45 g, 68.5 mmol) were suspended in $CH_2Cl_2$ (38 ml) and 3-thiophenecarbonyl chloride (4.3 g, 29.3 mmol) was added. The reaction was stirred at room temperature for 17.5 hours and then quenched with water (50 ml) and filtered. The solid was washed with $CH_2Cl_2$ and then the solvent was removed in vacuo to provide the intermediate napthyl alcohol.

This material was suspended in $CH_2Cl_2$ (100 ml) and pyridine (7.0 ml, 86.5 mmol) was added. The reaction was cooled in an ice water bath, and then $Tf_2O$ (5.0 ml, 29.7 mmol) was added via syringe over about 1 minute. The reaction was stirred at 0 C for 25 minutes, and then more $Tf_2O$ (0.8 ml, 5 mmol) was added. The reaction was stirred for 20 more minutes and then quenched with saturated $NaHCO_3$ (150 ml). The reaction was stirred for 1 hour, the layers were separated, and the aqueous phase was extracted with EtOAc (3×80 ml). The organic extracts were combined, washed with brine (50 ml), dried over $MgSO_4$, filtered, and concentrated. At this time, the reaction was repeated using $CH_2Cl_2$ (10 ml), pyridine (6.0 ml), and $Tf_2O$ (5.6 ml), following the procedure and workup described above. The crude material obtained was purified on silica gel (3:1->2:1->1:1 hexanes/EtOAc) to give title compound (2.52 g, 31% over two steps). MS (ESI pos. ion) m/z: 402.0 (M+H). Calc'd Exact Mass for $C_{16}H_{10}F_3NO_4S_2$: 401.

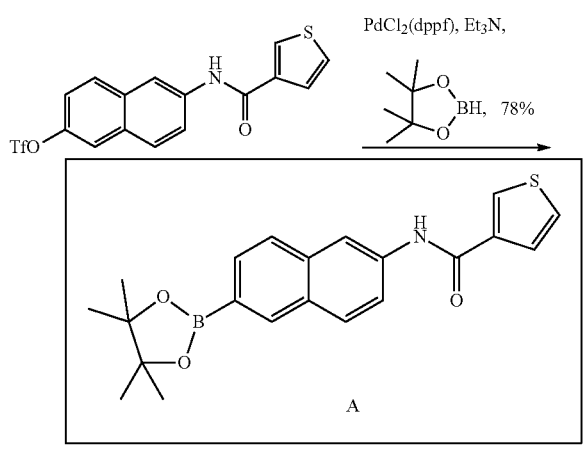

N-(6-(4,4,5,5-tetramethyl-1,3,2-dioxaborolan-2-yl) naphthalen-2-yl)thiophene-3-carboxamide (A)

The starting triflate (454.8 mg, 1.13 mmol) was dissolved in 1,4-dioxane (7.0 ml) and Et₃N (0.48 ml, 3.4 mmol) and PdCl₂(dppf) (100.2 mg, 0.123 mmol) was added. Argon was bubbled through for 15 minutes, and then 4,4,5,5-Tetramethyl-1,3,2-dioxaborolane solution (2.4 ml, 1.0 M in THF) was added via syringe, causing gas evolution. The reaction was stirred at room temperature for 20 minutes, and then placed in a preheated oil bath (79 C) and stirred overnight under argon. The reaction was then cooled to room temperature, diluted with water (15 ml), and extracted with CH₂Cl₂ (3×15 ml). The organic extracts were washed with water (2×20 ml), dried over MgSO₄, filtered, concentrated, and purified on silica gel (4:1->3:1 hexanes/EtOAc) to give title compound (335.4 mg, 78% yield).

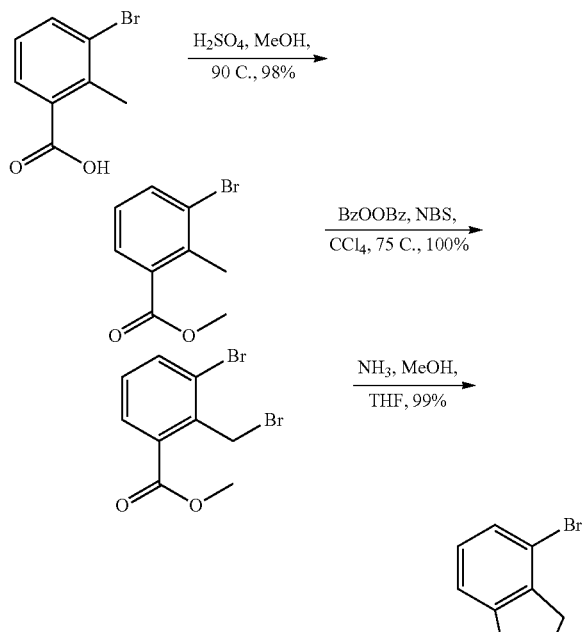

Bromoisoindolin-1-one 3-bromo-2-methylbenzoic acid (6.13 g, 28.5 mmol) was suspended in MeOH (52 ml) and concentrated H₂SO₄ (10.0 ml) was added via syringe over 4 minutes at room temperature. The reaction was heated to 90 C, stirred for 4 hours, cooled in an ice water bath, and then quenched with saturated NaHCO₃ (250 ml). The reaction was extracted with EtOAc (3×50 ml), and the organic layers were combined, dried over MgSO₄, filtered, and concentrated to give methyl 3-bromo-2-methylbenzoate (6.43 g, 98%).

Methyl 3-bromo-2-methylbenzoate (7.45 g, 32.5 mmol) was dissolved in CCl₄ (94 ml) and N-bromosuccinimide (6.67 g, 37.5 mmol) and benzoyl peroxide (0.38 g, 1.6 mmol) were added. The reaction was heated to 75 C-85 C, stirred for 3 hours and 45 minutes, cooled to room temperature, and filtered. The filtrate was concentrated and purified on SiO₂ (Biotage instrument; 0%->20% EtOAc/hexanes) to give methyl 3-bromo-2-(bromomethyl)benzoate (10.07 g, 100%).

Methyl 3-bromo-2-(bromomethyl)benzoate (10.30 g, 33.44 mmol) was dissolved in THF (93 ml) and cooled in an ice water bath. Then, NH₃ (60 ml, ~7N in MeOH) was added via syringe over 4.5 minutes. The reaction was warmed to room temperature, stirred for 7.5 hours, and then diluted with water. The aqueous phase was extracted repeatedly with CH₂Cl₂ and EtOAc. The organic extracts were combined, dried over sodium sulfate, filtered, and concentrated to give title compound (6.99 g, 99%) as a white powder. MS (ESI pos. ion) m/z: 212.0 (M+H). Calc'd Exact Mass for $C_8H_6BrNO$: 211.

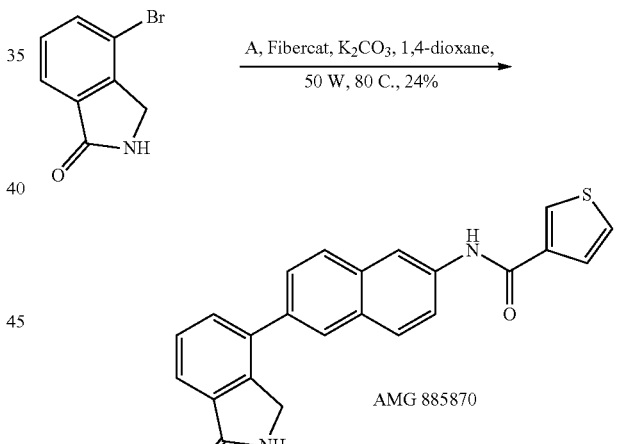

N-(6-(1-oxoisoindolin-4-yl)naphthalen-2-yl) thiophene-3-carboxamide

Bromoisoindolin-1-one (11.5 mg, 0.0542 mmol), N-(6-(4,4,5,5-tetramethyl-1,3,2-dioxaborolan-2-yl)naphthalen-2-yl) thiophene-3-carboxamide (43.3 mg, 0.114 mmol), Fibercat palladium catalyst (Johnson-Matthey, 21.0 mg), and K₂CO₃ (2 M in water, 0.1 ml, 0.2 mmol) were combined in a microwave reaction vessel and 1,4-dioxane (0.55 ml) was added. The reaction tube was sealed and heated in the microwave (CEM microwave) for 10 minutes at 50 Watts and 80 C. The reaction was cooled to room temperature, diluted with water (10 ml), and extracted with dichloromethane (6×5 ml). The organic extracts were combined, dried over sodium sulfate, filtered, and concentrated. The crude material was washed with 15:1 hexanes/EtOAc and then purified on HPLC (10%->95% MeCN/water with 0.1% TFA) to afford title compound (4.9 mg, 24%). MS (ESI pos. ion) m/z: 385 (M+H). Calc'd Exact Mass for $C_{23}H_{16}N_2O_2S$: 384.

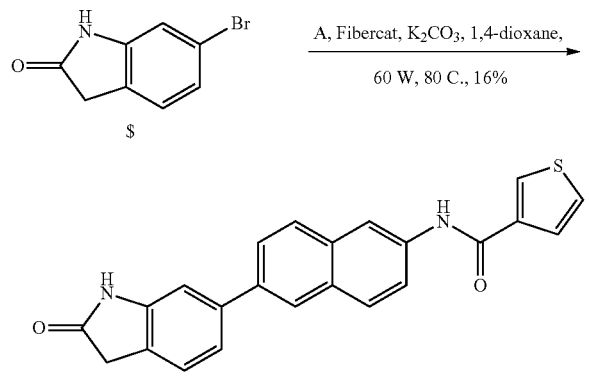

AMG 886268

N-(6-(2-oxoindolin-6-yl)naphthalen-2-yl)thiophene-3-carboxamide 6-bromoindolin-2-one (25.2 mg, 0.119 mmol), N-(6-(4,4,5,5-tetramethyl-1,3,2-dioxaborolan-2-yl)naphthalen-2-yl)thiophene-3-carboxamide (72.1 mg, 0.190 mmol), Fibercat palladium catalyst (Johnson-Matthey, 35.4 mg), and $K_2CO_3$ (2 M in water, 0.25 ml, 0.5 mmol) were combined in a microwave reaction vessel and 1,4-dioxane (1.1 ml) was added. The reaction tube was sealed and heated in the microwave (CEM microwave) at 60 Watts and 80 C, first for 10 minutes, and then for 20 minutes. The reaction was cooled to room temperature, diluted with water (5 ml), and extracted with dichloromethane (3×10 ml) and EtOAc (6×10 ml). The organic extracts were combined, dried over sodium sulfate, filtered, concentrated, and purified on HPLC (10%->95% MeCN/water with 0.1% TFA) to afford title compound (7.1 mg, 16%). MS (ESI pos. ion) m/z: 385 (M+H). Calc'd Exact Mass for $C_{23}H_{16}N_2O_2S$: 384.

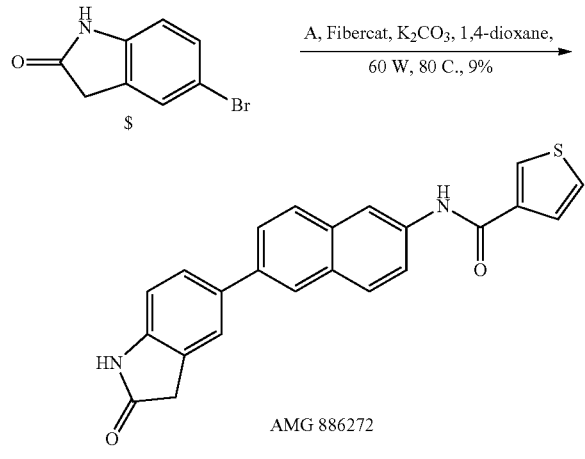

AMG 886272

N-(6-(2-oxoindolin-5-yl)naphthalen-2-yl)thiophene-3-carboxamide 5-bromoindolin-2-one (23.6 mg, 0.111 mmol), N-(6-(4,4,5,5-tetramethyl-1,3,2-dioxaborolan-2-yl)naphthalen-2-yl)thiophene-3-carboxamide (75.0 mg, 0.198 mmol), Fibercat palladium catalyst (Johnson-Matthey, 36.3 mg), and $K_2CO_3$ (2 M in water, 0.25 ml, 0.5 mmol) were combined in a microwave reaction vessel and 1,4-dioxane (1.1 ml) was added. The reaction tube was sealed and heated in the microwave (CEM microwave) at 60 Watts and 80 C, first for 10 minutes, and then for 20 minutes. The reaction was cooled to room temperature, diluted with water (5 ml), and extracted with dichloromethane (3×10 ml) and EtOAc (6×10 ml). The organic extracts were combined, dried over sodium sulfate, filtered, concentrated, and purified two times on HPLC (10%->95% MeCN/water with 0.1% TFA) to afford title compound (3.8 mg, 9%). MS (ESI pos. ion) m/z: 385 (M+H). Calc'd Exact Mass for $C_{23}H_{16}N_2O_2S$: 384.

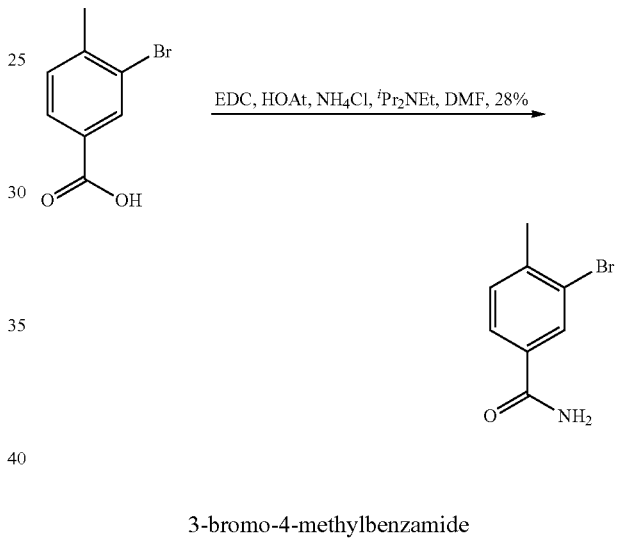

3-bromo-4-methylbenzamide 3-bromo-4-methylbenzoic acid (3.12 g, 14.5 mmol) was dissolved in DMF (26 ml) and EDC (3.51 g, 18.3 mmol), HOAt (2.79 g, 20.5 mmol), ammonium chloride (3.05 g, 57.0 mmol), and diisopropylethylamine (7.5 ml, 43.1 mmol) were added. The reaction was stirred at room temperature over the weekend, and then poured into water (100 ml), and diluted with more water. The resultant precipitate was filtered, washed with water, collected as a solution in EtOAc, and concentrated to give title compound (858.7 mg, 28%). MS (ESI pos. ion) m/z: 214 (M+H). Calc'd Exact Mass for $C_8H_8BrNO$: 213.

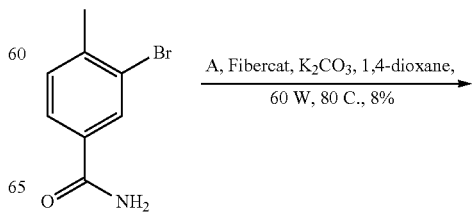

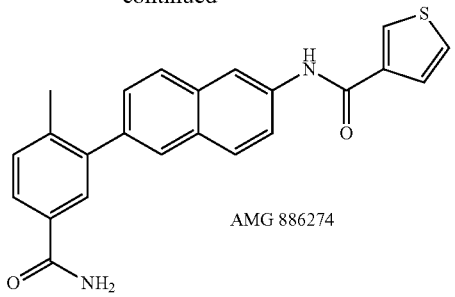

AMG 886274

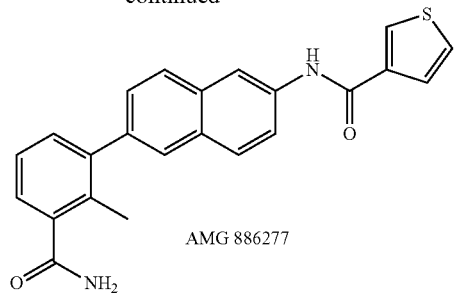

AMG 886277

N-(6-(5-carbamoyl-2-methylphenyl)naphthalen-2-yl)thiophene-3-carboxamide 3-bromo-4-methylbenzamide (22.7 mg, 0.106 mmol), N-(6-(4,4,5,5-tetramethyl-1,3,2-dioxaborolan-2-yl)naphthalen-2-yl)thiophene-3-carboxamide (62.5 mg, 0.165 mmol), Fibercat palladium catalyst (Johnson-Matthey, 35.1 mg), and $K_2CO_3$ (2 M in water, 0.24 ml, 0.48 mmol) were combined in a microwave reaction vessel and 1,4-dioxane (1.1 ml) was added. The reaction tube was sealed and heated in the microwave (CEM microwave) at 60 Watts and 80 C for 10 minutes and then for 20 minutes. The reaction was cooled to room temperature, diluted with water (5 ml), extracted with dichloromethane (3×10 ml), diluted with 1,4-dioxane (10 ml), and extracted with EtOAc (3×10 ml). The organic extracts were combined, dried over magnesium sulfate, filtered, concentrated, and purified on HPLC (10%->95% MeCN/water with 0.1% TFA) to afford title compound (3.2 mg, 8%). MS (ESI pos. ion) m/z: 387 (M+H). Calc'd Exact Mass for $C_{23}H_{18}N_2O_2S$: 386.

N-(6-(3-carbamoyl-2-methylphenyl)naphthalen-2-yl)thiophene-3-carboxamide 3-bromo-2-methylbenzamide (12.5 mg, 0.0584 mmol), N-(6-(4,4,5,5-tetramethyl-1,3,2-dioxaborolan-2-yl)naphthalen-2-yl)thiophene-3-carboxamide (45.8 mg, 0.121 mmol), Fibercat palladium catalyst (Johnson-Matthey, 31.9 mg), and $K_2CO_3$ (2 M in water, 0.15 ml, 0.30 mmol) were combined in a microwave reaction vessel and 1,4-dioxane (0.7 ml) was added. The reaction tube was sealed and heated in the microwave (CEM microwave) at 60 Watts and 80 C for 10 minutes and then cooled to room temperature. The reaction was diluted with water (5 ml) and extracted with dichloromethane (3×10 ml) and EtOAc (10 ml). The organic extracts were combined, dried over magnesium sulfate, filtered, concentrated, and purified on HPLC (10%->95% MeCN/water with 0.1% TFA) to afford title compound (6.6 mg, 29%). MS (ESI pos. ion) m/z: 387 (M+H). Calc'd Exact Mass for $C_{23}H_{18}N_2O_2S$: 386.

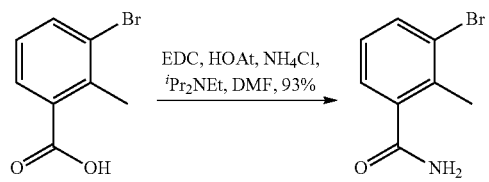

3-bromo-2-methylbenzamide 3-bromo-2-methylbenzoic acid (5.00 g, 23.3 mmol) was dissolved in DMF (41.6 ml) and EDC (5.46 g, 28.5 mmol), HOAt (3.97 g, 29.2 mmol), ammonium chloride (4.90 g, 90.9 mmol), and diisopropylethylamine (12.5 ml, 71.8 mmol) were added. The reaction was stirred at room temperature over the weekend, and then poured into water (100 ml). The resultant precipitate was filtered, washed with water, collected, and dried under vacuum to give the title compound (4.63 g, 93%). MS (ESI pos. ion) m/z: 214 (M+H). Calc'd Exact Mass for $C_8H_8BrNO$: 213.

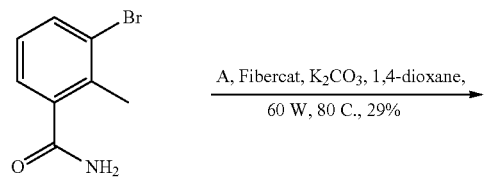

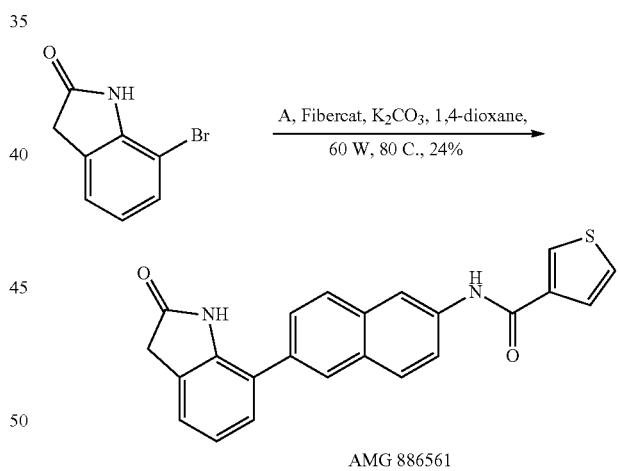

AMG 886561

N-(6-(2-oxoindolin-7-yl)naphthalen-2-yl)thiophene-3-carboxamide 7-bromoindolin-2-one (25.4 mg, 0.120 mmol), N-(6-(4,4,5,5-tetramethyl-1,3,2-dioxaborolan-2-yl)naphthalen-2-yl)thiophene-3-carboxamide (89.5 mg, 0.236 mmol), Fibercat palladium catalyst (Johnson-Matthey, 35.4 mg), and $K_2CO_3$ (2 M in water, 0.34 ml, 0.68 mmol) were combined in a microwave reaction vessel and 1,4-dioxane (1.2 ml) was added. The reaction tube was sealed and heated in the microwave (CEM microwave) at 60 Watts and 80 C, first for 10 minutes, and then for 20 minutes. The reaction was cooled to room temperature, diluted with water (5 ml), and extracted with EtOAc (20 ml, 5 ml, 2×10 ml). The organic extracts were combined, dried over sodium sulfate, filtered, concentrated, and purified on HPLC (10%->95% MeCN/water with 0.1% TFA). The fractions with product were purified on silica gel (3:2 hexanes/EtOAc->EtOAc->4:1 EtOAc/MeOH) to afford title compound (11.2 mg, 24%). MS (ESI pos. ion) m/z: 385 (M+H). Calc'd Exact Mass for $C_{23}H_{16}N_2O_2S$: 384.

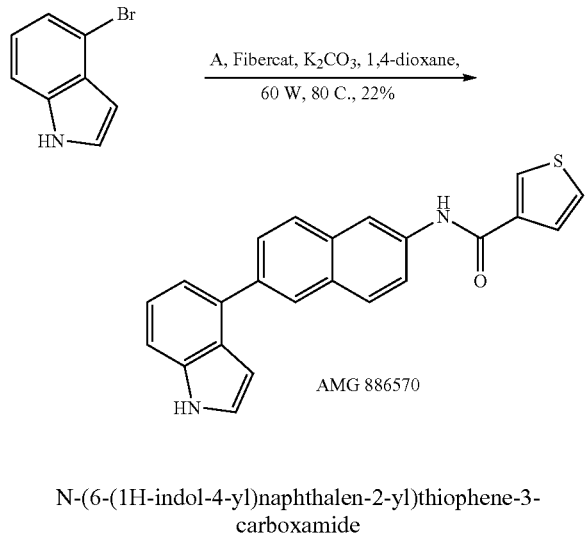

AMG 886570

N-(6-(1H-indol-4-yl)naphthalen-2-yl)thiophene-3-carboxamide 4-bromo-1H-indole (31.0 mg, 0.158 mmol), N-(6-(4,4,5,5-tetramethyl-1,3,2-dioxaborolan-2-yl)naphthalen-2-yl)thiophene-3-carboxamide (114.5 mg, 0.302 mmol), Fibercat palladium catalyst (Johnson-Matthey, 34.5 mg), and $K_2CO_3$ (2 M in water, 0.45 ml, 0.90 mmol) were combined in a microwave reaction vessel and 1,4-dioxane (1.5 ml) was added. The reaction tube was sealed and heated in the microwave (CEM microwave) at 60 Watts and 80 C, first for 10 minutes, and then for 20 minutes. The reaction was cooled to room temperature, diluted with water (5 ml), and extracted with EtOAc (10 ml, 2×5 ml). The organic extracts were combined, dried over sodium sulfate, filtered, concentrated, and purified on HPLC (10%->95% MeCN/water with 0.1% TFA). The fractions with product were purified on silica gel (3:1->1:1 hexanes/EtOAc) to afford title compound (12.8 mg, 22%). MS (ESI pos. ion) m/z: 369 (M+H). Calc'd Exact Mass for $C_{23}H_{16}N_2OS$: 368.

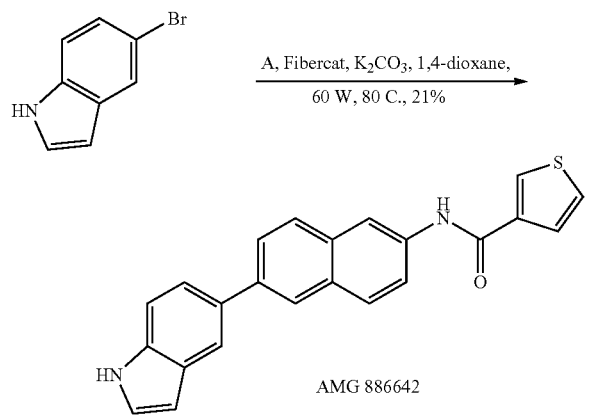

AMG 886642

N-(6-(1H-indol-5-yl)naphthalen-2-yl)thiophene-3-carboxamide 5-bromo-1H-indole (31.4 mg, 0.160 mmol), N-(6-(4,4,5,5-tetramethyl-1,3,2-dioxaborolan-2-yl)naphthalen-2-yl)thiophene-3-carboxamide (114 mg, 0.301 mmol), Fibercat palladium catalyst (Johnson-Matthey, 31 mg), and $K_2CO_3$ (2 M in water, 0.45 ml, 0.90 mmol) were combined in a microwave reaction vessel and 1,4-dioxane (1.5 ml) was added. The reaction tube was sealed and heated in the microwave (CEM microwave) at 60 Watts and 80 C for 20 minutes. The reaction was cooled to room temperature, diluted with water (5 ml), and extracted with EtOAc (3×10 ml). The organic extracts were combined, dried over sodium sulfate, filtered, concentrated, and purified on silica gel (5:1->4:1->2:1 hexanes/EtOAc) to afford crude product. This crude material was then purified two times via HPLC (10%->95% MeCN/water with 0.1% TFA) afford title compound (12.2 mg, 21%). MS (ESI pos. ion) m/z: 369 (M+H). Calc'd Exact Mass for $C_{23}H_{16}N_2OS$: 368.

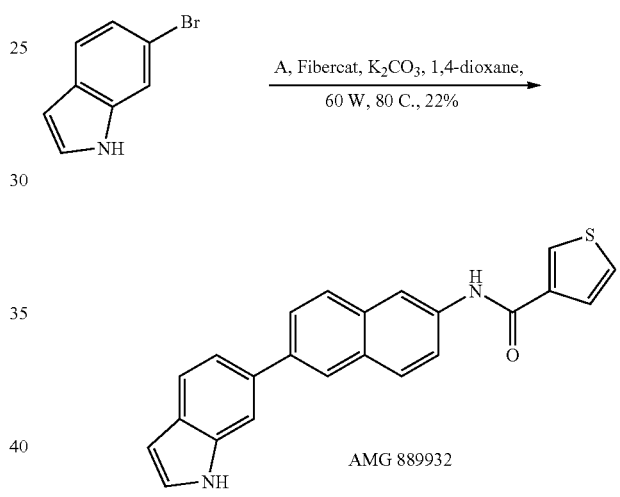

AMG 889932

N-(6-(1H-indol-6-yl)naphthalen-2-yl)thiophene-3-carboxamide 6-bromo-1H-indole (28.8 mg, 0.147 mmol), N-(6-(4,4,5,5-tetramethyl-1,3,2-dioxaborolan-2-yl)naphthalen-2-yl)thiophene-3-carboxamide (109.2 mg, 0.288 mmol), Fibercat palladium catalyst (Johnson-Matthey, 55.5 mg), and $K_2CO_3$ (2 M in water, 0.50 ml, 1.0 mmol) were combined in a microwave reaction vessel and 1,4-dioxane (1.5 ml) was added. The reaction tube was sealed and heated in the microwave (CEM microwave) at 60 Watts and 80 C for 20 minutes. The reaction was then cooled to room temperature, diluted with water (5 ml), and extracted with EtOAc (10 ml; 2×5 ml). The organic extracts were combined, dried over sodium sulfate, filtered, concentrated, and purified via HPLC (10%->95% MeCN/water with 0.1% TFA), silica gel (4:1->3:1->2:1->1:1 hexanes/EtOAc) to afford crude product. This crude material was then purified again via HPLC (same conditions as above) to afford title compound (11.9 mg, 22%). MS (ESI pos. ion) m/z: 369 (M+H). Calc'd Exact Mass for $C_{23}H_{16}N_2OS$: 368.

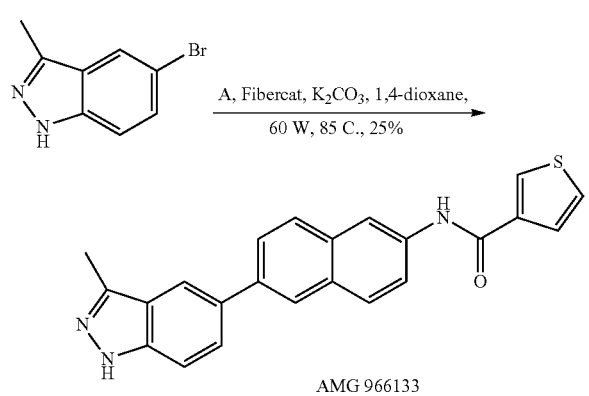

N-(6-(3-methyl-1H-indazol-5-yl)naphthalen-2-yl)thiophene-3-carboxamide 5-bromo-3-methyl-1H-indazole (30.7 mg, 0.145 mmol), N-(6-(4,4,5,5-tetramethyl-1,3,2-dioxaborolan-2-yl)naphthalen-2-yl)thiophene-3-carboxamide (110.3 mg, 0.291 mmol), Fibercat palladium catalyst (Johnson-Matthey, 59.3 mg), and $K_2CO_3$ (2 M in water, 0.50 ml, 1.0 mmol) were combined in a microwave reaction vessel and 1,4-dioxane (1.6 ml) was added. The reaction tube was sealed and heated in the microwave (CEM microwave) at 60 Watts and 85 C for 20 minutes. The reaction was then cooled to room temperature, diluted with water (5 ml), and extracted with EtOAc (3×10 ml). The organic extracts were combined, dried over sodium sulfate, filtered, concentrated, and purified via silica gel (Biotage instrument, 13% EtOAc/hexanes->100% EtOAc). This crude material was then purified via HPLC (10%->95% MeCN/water with 0.1% TFA) to afford title compound (14.0 mg, 25%). MS (ESI pos. ion) m/z: 384 (M+H). Calc'd Exact Mass for $C_{23}H_{17}N_3OS$: 383.

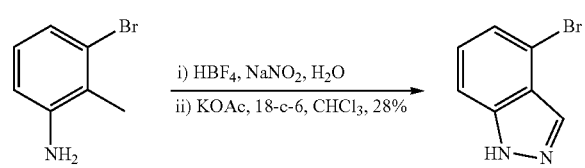

4-bromo-1H-indazole 3-bromo-2-methylaniline (1.70 ml, 13.8 mmol) was added to water (6 ml) in a corning, conical reaction vessel cooled in an ice water bath, and $HBF_4$ (6.5 ml, 49.7 mmol) was added. Then, $NaNO_2$ (0.99 g, 14.3 mmol) in water (2 ml), cooled in an ice water bath, was added via syringe, and the thick suspension was stirred while being warmed to room temperature over 45 minutes. It was then recooled in an ice water bath and filtered via a Buchner funnel. The solid was washed with 5% aqueous $HBF_4$ (100 ml), the filtrate was filtered again, and the solid from both filtrations was washed with precooled (0 C) MeOH (4×25 ml) and precooled (0 C) diethyl ether (2×25 ml). The solid was then dried on a Buchner funnel for 30 minutes and then added to a flask containing KOAc (2.90 g, 29.5 mmol) and 18-c-6 (203 mg, 0.768 mmol) suspended in chloroform (100 ml). The reaction was stirred at room temperature for 2 hours and 20 minutes and then filtered, and the solid was washed with chloroform. The filtrate was washed with water (50 ml) and brine (50 ml), dried over sodium sulfate, filtered, concentrated, and diluted with water (150 ml). The suspension was filtered, and the solid was washed with hexanes, collected, and put under vacuum overnight to give title compound (773.6 mg, 28%). MS (ESI pos. ion) m/z: 197 (M+H). Calc'd Exact Mass for $C_7H_5BrN_2$: 196.

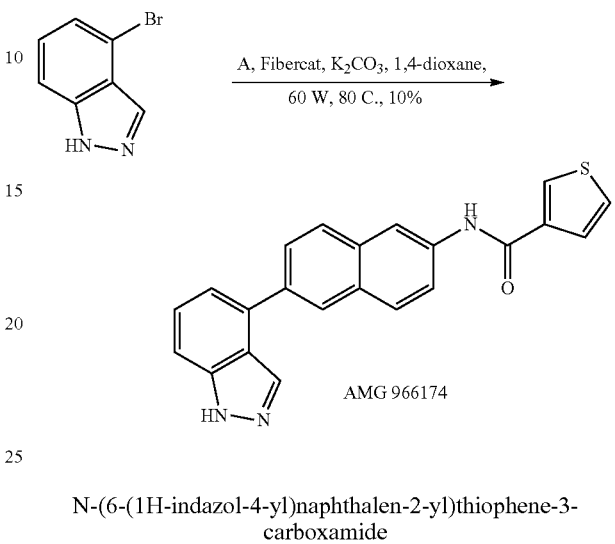

N-(6-(1H-indazol-4-yl)naphthalen-2-yl)thiophene-3-carboxamide 4-bromo-1H-indazole (37.9 mg, 0.192 mmol), N-(6-(4,4,5,5-tetramethyl-1,3,2-dioxaborolan-2-yl)naphthalen-2-yl)thiophene-3-carboxamide (145.7 mg, 0.384 mmol), Fibercat palladium catalyst (Johnson-Matthey, 64.7 mg), and $K_2CO_3$ (2 M in water, 0.75 ml, 1.5 mmol) were combined in a microwave reaction vessel and 1,4-dioxane (2.3 ml) was added. The reaction tube was sealed and heated in the microwave (CEM microwave) at 60 Watts and 85 C for 20 minutes. The reaction was then cooled to room temperature, diluted with water (5 ml), and extracted with EtOAc (3×10 ml). The organic extracts were combined, washed with water (3×5 ml), dried over sodium sulfate, filtered, concentrated, and purified via silica gel (Biotage instrument, 13%->75% EtOAc/hexanes). This crude material was then purified via HPLC (10%->95% MeCN/water with 0.1% TFA) to afford title compound (7.4 mg, 10%). MS (ESI pos. ion) m/z: 370 (M+H). Calc'd Exact Mass for $C_{22}H_{15}N_3OS$: 369.

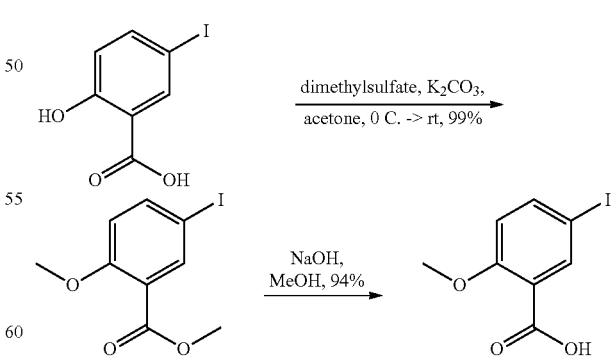

5-iodo-2-methoxybenzoic acid 5-iodo-2-hydroxybenzoic acid (2.81 g, 10.6 mmol) was suspended in acetone (50 ml) and $K_2CO_3$ (6.77 g, 49.0 mmol)

was added. The reaction was cooled in an ice water bath, and dimethylsulfate (2.4 ml, 25 mmol) was added via syringe. The reaction was warmed to room temperature, then heated to reflux, and stirred overnight. After 14.75 hours, the reaction was cooled to room temperature, diluted with water (150 ml), and stirred for 30 minutes. It was then extracted with EtOAc (3×50 ml), and the organic extracts were combined, dried over magnesium sulfate, filtered, concentrated, and purified on silica gel (Biotage instrument, 5% EtOAc/hexanes->100% EtOAc) to give methyl 5-iodo-2-methoxybenzoate (3.08 g, 99%).

This material was dissolved in MeOH (25 ml) and 1 N NaOH (15 ml, 15 mmol) was added. The reaction was stirred at room temperature for 2 hours, at which time more MeOH (8 ml) and 1 N NaOH (8 ml, 8 mmol) were added. The reaction was heated to 60 C and stirred for 2.25 hours, and then cooled to room temperature. The resultant suspension was filtered, and the solid was collected and dried in vacuo to give the title compound (2.75 g, 94%). MS (ESI pos. ion) m/z: 279 (M+H). Calc'd Exact Mass for $C_8H_7IO_3$: 278.

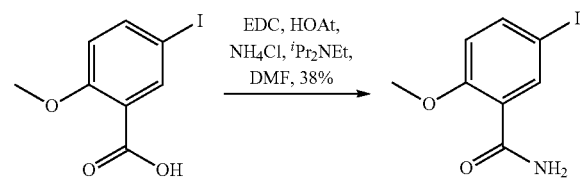

5-iodo-2-methoxybenzamide 5-iodo-2-methoxybenzoic acid (1.01 g, 3.63 mmol) was dissolved in DMF (8.0 ml) and EDC (0.86 g, 4.5 mmol), HOAt (0.59 g, 4.3 mmol), ammonium chloride (0.79 g, 14.8 mmol), and $^iPr_2NEt$ (2.0 ml, 11.5 mmol) were added. The reaction was stirred at room temperature under nitrogen overnight, and then poured into water (40 ml), resulting in the formation of a precipitate. The suspension was filtered and the solid was collected. The filtrate was extracted with EtOAc (3×25 ml), and the organic extracts were combined, dried over sodium sulfate, filtered, combined with the filtered solid, and concentrated. The crude was dissolved in DMF (ca. 10 ml) and poured into water (60 ml). This was then cooled in an ice water bath, and filtered, and the solid was collected and dried in vacuo to give title compound (0.38 g, 38%). MS (ESI pos. ion) m/z: 278 (M+H). Calc'd Exact Mass for $C_8H_8INO_2$: 277.

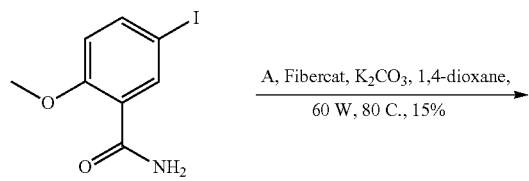

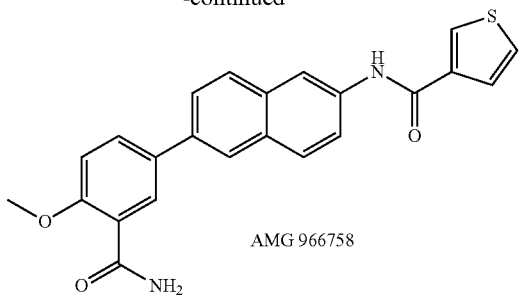

N-(6-(3-carbamoyl-4-methoxyphenyl)naphthalen-2-yl)thiophene-3-carboxamide 5-iodo-2-methoxybenzamide (47.9 mg, 0.173 mmol), N-(6-(4,4,5,5-tetramethyl-1,3,2-dioxaborolan-2-yl)naphthalen-2-yl)thiophene-3-carboxamide (140.4 mg, 0.370 mmol), Fibercat palladium catalyst (Johnson-Matthey, 70.1 mg), and $K_2CO_3$ (2 M in water, 0.65 ml, 1.3 mmol) were combined in a microwave reaction vessel and 1,4-dioxane (1.8 ml) was added. The reaction tube was sealed and heated in the microwave (CEM microwave) at 60 Watts and 85 C for 20 minutes. The reaction was then cooled to room temperature, diluted with water (5 ml), and extracted with EtOAc (4×10 ml). The organic extracts were combined, dried over sodium sulfate, filtered, concentrated, and purified via silica gel (Biotage instrument, 13%->100% EtOAc/hexanes). This crude material was then purified via HPLC (10%->95% MeCN/water with 0.1% TFA) to afford title compound (10.6 mg, 15%). MS (ESI pos. ion) m/z: 403 (M+H). Calc'd Exact Mass for $C_{23}H_{18}N_2O_3S$: 402.

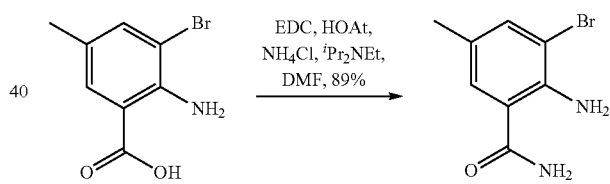

2-amino-3-bromo-5-methylbenzamide 2-amino-3-bromo-5-methylbenzoic acid (2.06 g, 8.95 mmol) was dissolved in DMF (19 ml) and EDC (2.10 g, 11.0 mmol), HOAt (1.56 g, 11.5 mmol), ammonium chloride (2.03 g, 38.0 mmol), and $^iPr_2NEt$ (6.5 ml, 37.3 mmol) were added. The reaction was stirred at room temperature under nitrogen for 21.5 hours, and then poured into water (50 ml), resulting in the formation of a precipitate. The suspension was filtered and the solid was washed with water and dried in vacuo to give title compound (1.83 g, 89%). MS (ESI pos. ion) m/z: 229 (M+H). Calc'd Exact Mass for $C_8H_9BrN_2O$: 228.

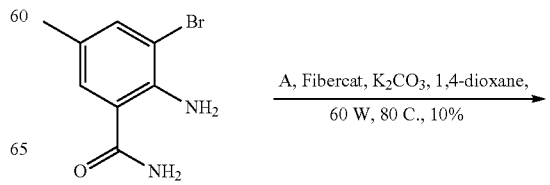

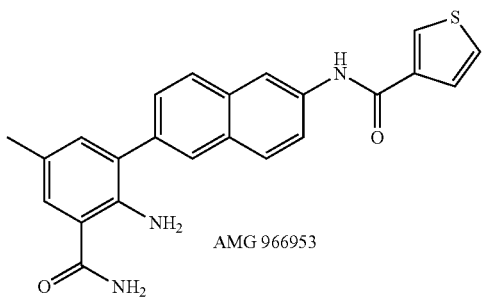

AMG 966953

N-(6-(2-amino-3-carbamoyl-5-methylphenyl)naphthalen-2-yl)thiophene-3-carboxamide 2-amino-3-bromo-5-methylbenzamide (31.8 mg, 0.139 mmol), N-(6-(4,4,5,5-tetramethyl-1,3,2-dioxaborolan-2-yl)naphthalen-2-yl)thiophene-3-carboxamide (122 mg, 0.370 mmol), Fibercat palladium catalyst (Johnson-Matthey, 68.2 mg), and $K_2CO_3$ (2 M in water, 0.51 ml, 1.0 mmol) were combined in a microwave reaction vessel and 1,4-dioxane (1.5 ml) was added. The reaction tube was sealed and heated in the microwave (CEM microwave) at 60 Watts and 80 C for 20 minutes. The reaction was then cooled to room temperature, diluted with water (5 ml), and extracted with EtOAc (4×10 ml). The organic extracts were combined, dried over sodium sulfate, filtered, concentrated, and purified via silica gel (Biotage instrument, 13%->50%->100% EtOAc/hexanes) to afford title compound (5.6 mg, 10%). MS (ESI pos. ion) m/z: 402 (M+H). Calc'd Exact Mass for $C_{23}H_{19}N_3O_2S$: 401.

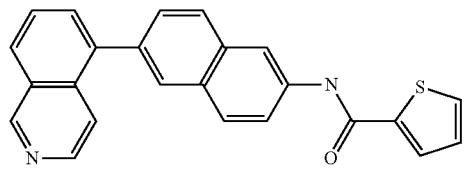

N-(6-(isoquinolin-5-yl)naphthalen-2-yl)thiophene-2-carboxamide

To a microwave vial containing 6-(thiophene-2-carboxamido)naphthalen-2-yl trifluoromethanesulfonate (0.100 g, 0.2 mmol), in 1,4-Dioxane (3 mL), was added isoquinolin-5-ylboronic acid (0.129 g, 0.8 mmol), Fibrecat catalyst (0.005 g, 5% by wt.), and Potassium Carbonate (2 M, 0.50 mL, 1 mmol). The vial was capped and placed into CEM Microwave for 10 minutes at 80° C., while supplying 50 Watts of power through power-max. The mixture was diluted with DCM (2 mL) and water (2 mL). The aqueous layer was extracted with DCM (3×10 mL). The combined organics was dried over sodium sulfate, filtered, and concentrated in-vacuo. The crude was purified from reverse-phase HPLC. This gave a yellow colored amorphous solid, which was titled product (0.078 g, 0.2 mmol). MS (ESI pos. ion) m/z: 381 (M+H).

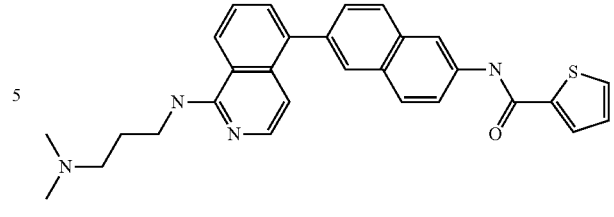

N-(6-(1-(3-(dimethylamino)propylamino)isoquinolin-5-yl)naphthalen-2-yl)thiophene-2-carboxamide Step 1: 1-chloro-5-nitroisoquinoline To a 500 mL 3-neck round-bottomed flask containing 1-Chloroisoquinoline (6.50 g, 39.8 mmol), was added $H_2SO_4$ (10.59 mL, 198.8 mmol), the mixture was heated to 60° C., with stirring under inert atmosphere. After 5 minutes, Potassium Nitrate (2.01 g, 19.9 mmol) was added and the mixture was stirred an additional 5 minutes. The heat source was removed, and the mixture was stirred for 5 minutes before it was cooled to 0° C. in an ice bath. Fuming Nitric Acid (8.41 mL, 198.8 mmol) was added into the mixture drop-wise by addition funnel over 20 minutes, while the reaction mixture was kept cold in ice bath. After the addition, the mixture was allowed to slowly warm to ambient temperature overnight. Then water was added to the mixture (200 mL), and stirred an additional 30 minutes. The solid was collected by filtration. After drying in a reduced-pressure oven for 6 hours, a light yellow powder was recovered, which was titled product (8.2 g, 39.3 mmol). MS (ESI pos. ion) m/z: 209 (M+H). Calc'd Exact Mass for $C_9H_5N_2O_2Cl$: 208.5

Step 2: 1-chloroisoquinolin-5-amine

To a 1000 mL 3-neck round-bottomed flask containing 1-chloro-5-nitroisoquinoline (Step 1, 8.200 g, 39.3 mmol) was added Iron powder (11.80 g, 211.2 mmol), while under a flow of inert gas. A 3:1 mixture of $EtOH/H_2O$ (240 mL), and $NH_4Cl$ (1.19 g, 22.4 mmol) were added. The mixture was heated to 80° C., while stirring under inert atmosphere for 1 hour. The oil bath was removed and the mixture was allowed to cool to ambient temperature. The crude material was filtered through a plug of Celite, and the filtrate was concentrated in-vacuo. Recrystallization from DCM/Hexanes, and further washing the solid with hexanes (3×100 mL) afforded a brown crystalline solid, which was titled product (7.015 g, 39.3 mmol). MS (ESI pos. ion) m/z: 179 (M+H). Calc'd Exact Mass for $C_9H_7N_2Cl$: 178.5

Step 3: 5-bromo-1-chloroisoquinoline

To a 500 mL round-bottomed flask containing 1-chloroisoquinolin-5-amine (Step 2, 5.8 g, 32.5 mmol) in $H_2O$ (33 mL) and 40% HBr (14 mL) chilled to −50 C in an ice bath, was added a freshly prepared solution of (Sodium nitrate (2.47 g, 35.7 mmol) in 8 mL of $H_2O$) drop-wise over 15 minutes. After the addition, the mixture was kept at 2° C., while stirred an additional 20 minutes. Then urea (0.192 g, 3.2 mmol) was added in order to decompose excess nitrate in the reaction mixture. After an additional 5 minutes of stirring the diazonium salt mixture was transferred into a dropping funnel. The diazonium salt was added drop-wise into a heated (70° C.) solution of Copper (1) Bromide (4.66 g, 32.5 mmol) in 40% HBr (30 mL)). After the addition, the mixture was heated to 80° C. for 1.5 hours. Then the mixture was allowed to cool to ambient temperature. The solid, which had formed in the reaction mixture, was collected by filtration. Then recrystallized from hot EtOAc and Hexanes, after drying, gave a brown crystalline solid, which was titled product (4.576 g; 18.9 mmol). MS (ESI pos. ion) m/z: 243 (M+H). Calc'd Exact Mass for $C_9H_5BrCl$: 242.5

Step 4: 5-bromo-N-(3-(dimethylamino)propyl)isoquinolin-1-amine

To a microwave vial containing 5-bromo-1-chloroisoquinoline (Step 3, 0.300 g, 1.2 mmol), dissolved in pyridine (3 mL), was added Dimethylaminopropyl-amine (0.16 mL, 1.3 mmol). The mixture was placed into CEM Microwave for 8 minutes at 100° C., while supplying 80 Watts of power via power-max. The mixture was diluted with DCM and water, and extracted with DCM (3×10 mL). Then dried organics (over sodium sulfate) was filtered, and concentrated in-vacuo. It was then purified by Amino-Propyl Silica-gel chromatography in MeOH/DCM. This gave tan colored oil, which was titled product (0.085 g, 0.3 mmol). MS (ESI pos. ion) m/z: 309; 310 (M+H). Calc'd Exact Mass for $C_{14}H_{18}N_3Br$: 308

Step 5: N-(6-(1-(3-(dimethylamino)propylamino)isoquinolin-5-yl)naphthalen-2-yl)thiophene-2-carboxamide To a microwave vial containing 5-bromo-N-(3(dimethylamino)propyl) isoquinolin-1-amine (Step 4, 0.055 g, 0.2 mmol) in 1,4-Dioxane (2 mL), was added N-(6-(4,4,5,5-tetramethyl-1,3,2-dioxaborolan-2-yl)naphthalen-2-yl)thiophene-2-carboxamide (0.076 g, 0.2 mmol), Fibrecat catalyst (0.005 g, 5% by wt.), along with 2 M Potassium Carbonate (0.5 mL, 1 mmol). The mixture was placed into CEM Microwave for 10 minutes at 80° C., while supplying 60 Watts of energy via power-max. Then mixture was diluted with DCM and $H_2O$, and extracted with DCM (3×10 mL). Then dried organics (over sodium sulfate) was filtered, and concentrated in-vacuo. The crude was purified on reverse-phase HPLC. This gave a light yellow amorphous solid after drying, which was titled product (0.026 g, 0.03 mmol). MS (ESI pos. ion) m/z: 481 (M+H). Calc'd Exact Mass for $C_{29}H_{28}N_4OS$: 480

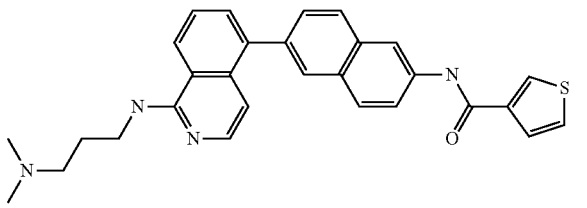

N-(6-(1-(3-(dimethylamino)propylamino)isoquinolin-5-yl)naphthalen-2-yl)thiophene-3-carboxamide To a microwave vial containing 5-bromo-N-(3(dimethylamino)propyl) isoquinolin-1-amine (Step 5, 0.055 g, 0.2 mmol) in 1,4-Dioxane (2 mL), was added N-(6-(4,4,5,5-tetramethyl-1,3,2-dioxaborolan-2-yl)naphthalen-2-yl)thiophene-3-carboxamide (0.100 g, 0.3 mmol), Fibrecat catalyst (0.005 g, 5% by wt.), along with 2 M Potassium Carbonate (0.5 mL, 1 mmol). The reaction mixture was placed into CEM Microwave for 10 minutes at 80° C., while supplying 60 Watts of energy via power-max. The mixture was diluted with DCM and $H_2O$, and extracted with DCM (3×10 mL). Then dried organics (over sodium sulfate), was filtered, and concentrated in-vacuo. The crude was purified on reverse-phase HPLC. This gave an off-white amorphous solid after drying, which was titled product (0.023 g, 0.08 mmol). MS (ESI pos. ion) m/z: 481 (M+H). Calc'd Exact Mass for $C_{29}H_{28}N_4OS$: 480

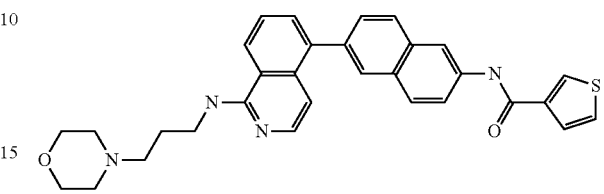

N-(6-(1-(3-morpholinopropylamino)isoquinolin-5-yl)naphthalen-2-yl)thiophene-2-carboxamide 5-bromo-N-(3-morpholinopropyl)isoquinolin-1-amine Followed similar experimental procedure for 5-bromo-N-(3-(dimethylamino)propyl)isoquinolin-1-amine. A tan colored amorphous solid was recovered after drying, which was titled product (0.119 g, 0.3 mmol). MS (ESI pos. ion) m/z: 351; 352 (M+H). Calc'd Exact Mass for $C_{16}H_{20}N_3OBr$: 350.

N-(6-(1-(3-morpholinopropylamino)isoquinolin-5-yl)naphthalen-2-yl)thiophene-2-carboxamide Follow exact experimental procedure in Step 5. Cloudy-white oil was recovered after drying, which was titled product (0.037 g, 0.07 mmol). MS (ESI pos. ion) m/z: 523 (M+H). Calc'd Exact Mass for $C_{31}H_{30}N_4O_2S$: 522.

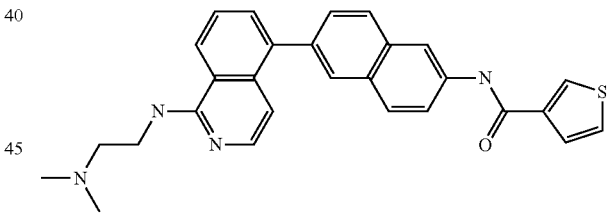

N-(6-(1-(2-(dimethylamino)ethylamino)isoquinolin-5-yl)naphthalen-2-yl)thiophene-2-carboxamide 5-bromo-N-(2-(dimethylamino)ethyl)isoquinolin-1-amine Following exact experimental procedure in Step 4, a tan colored amorphous solid was recovered after drying, which was titled product (0.102 g, 0.4 mmol). MS (ESI pos. ion) m/z: 295; 296 (M+H). Calc'd Exact Mass for $C_{13}H_{16}N_3OBr$: 294.

N-(6-(1-(2-(dimethylamino)ethylamino)isoquinolin-5-yl)naphthalen-2-yl)thiophene-2-carboxamide Following exact experimental procedure in Step 5, a tan colored oil was recovered after drying, which was titled product (0.034 g, 0.07 mmol). MS (ESI pos. ion) m/z: 467 (M+H). Calc'd Exact Mass for $C_{28}H_{26}N_4OS$: 466.

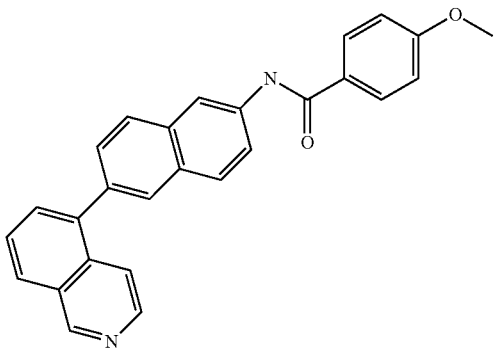

N-(6-(isoquinolin-5-yl)naphthalen-2-yl)-4-methoxybenzamide (1) N-(6-hydroxynaphthalen-2-yl)-4-methoxybenzamide To a 100 mL round-bottomed flask containing 6-aminonaphthalen-2-ol (0.600 g, 3.8 mmol), in DCM (10 mL), was added p-Anisoyl chloride (0.972 g, 5.7 mmol), along with $K_2CO_3$ (1.57 g, 11.4 mmol). The mixture was stirred at ambient temperature overnight and was diluted with DCM and $H_2$., Extraction with DCM (3×10 mL), drying of the organics over sodium sulfate, filtration, and concentration in-vacuo afforded the crude product. Recrystallization of the crude from DCM/Hexanes gave a tan colored amorphous solid, after drying (0.300 g, 1.0 mmol). MS (ESI pos. ion) m/z: 294 (M+H). Calc'd Exact Mass for $C_{18}H_{15}NO_3$: 293.

(2) 6-(4-methoxybenzamido)naphthalen-2-yl trifluoromethanesulfonate

To a 100 mL round-bottomed flask containing N-(6-hydroxynaphthalen-2-yl)-4-methoxybenzamide (0.300 g, 1.0 mmol) in DCM (10 mL), was added Pyridine (0.16 mL, 2.0 mmol). Then chilled mixture to 0° C. in ice bath, while stirring under inert atmosphere. Trifluoroacetic anhydride (0.25 mL, 1.5 mmol) was added to the mixture drop-wise. The resulting mixture was then stirred at 0° C. for 4 hours. $H_2O$ was added into the mixture, which was then extracted with DCM (3×10 mL). The dried organics (over sodium sulfate) was filtered, and concentrated in-vacuo. This product was carried into the next step of synthesis without further purification, to prevent decomposition. A tan colored oil was recovered after drying (0.100 g, 0.2 mmol). MS (ESI pos. ion) m/z: 426 (M+H). Calc'd Exact Mass for $C_{19}H_{14}F_3NO_5S$: 425.
(3) To a microwave vial containing 6-(4-methoxybenzamido) naphthalen-2-yl trifluoromethanesulfonate (0.100 g, 0.2 mmol), in 1,4-Dioxane (3 mL), was added isoquinolin-5-ylboronic acid (0.129 g, 0.8 mmol), Fibrecat catalyst (0.005 g, 5% by wt.), 2 M Potassium Carbonate (0.50 mL, 1 mmol). The vial was capped and placed into CEM Microwave for 10 minutes at 80° C., while supplying 50 Watts of power through power-max. The diluted mixture [with DCM (2 ml) and water (2 mL)] was extracted with DCM (3×10 mL). The dried organics (over sodium sulfate) was filtered, and concentrated in-vacuo. The crude was purified from reverse-phase HPLC. This gave a tan colored amorphous solid, which was titled product (0.0023 g, 0.006 mmol) MS (ESI pos. ion) m/z: 405 (M+H). Calc'd Exact Mass for $C_{27}H_{20}N_2O_2$: 404.

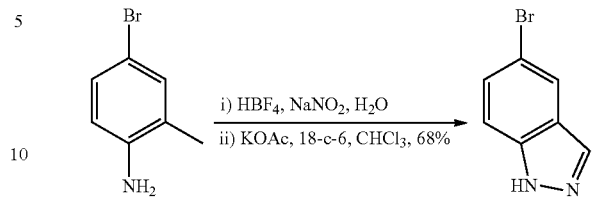

5-bromo-1H-indazole 4-bromo-2-methylaniline (5.0 g, 27 mmol) was added to a mixture of water (12.3 ml) and $HBF_4$ (48% by weight in water, 12.3 ml, 67 mmol) in a Nalger reaction vessel cooled in an ice water bath. Then, $NaNO_2$ (1.85 g, 27 mmol) in water (3.8 ml) was added while maintaining the temperature of the reaction around 10 C. After 15 minutes, the was then recooled in an ice water bath and filtered via a Buchner funnel. The solid was washed with cold 5% aqueous $HBF_4$, cold MeOH (20 ml) and diethyl ether (3×10 ml). The solid was dried on a Buchner funnel for 1 hour and then added to a flask containing KOAc (5.3 g, 54 mmol, dried in vacuo overnight) and 18-c-6 (0.35 g, 1.3 mmol) suspended in chloroform (250 ml). The reaction was stirred at room temperature for 2 hours and then filtered, and the solid was washed with chloroform. The filtrate was washed with water and brine, dried over sodium sulfate, filtered, concentrated, and diluted with water (250 ml). The suspension was filtered, and the solid was washed with hexanes (50 ml) and diethyl ether (50 ml), collected, and dried in vacuo to give title compound (3.6 g, 68%). MS (ESI pos. ion) m/z: 197 (M+H). Calc'd Exact Mass for $C_7H_5BrN_2$: 196.

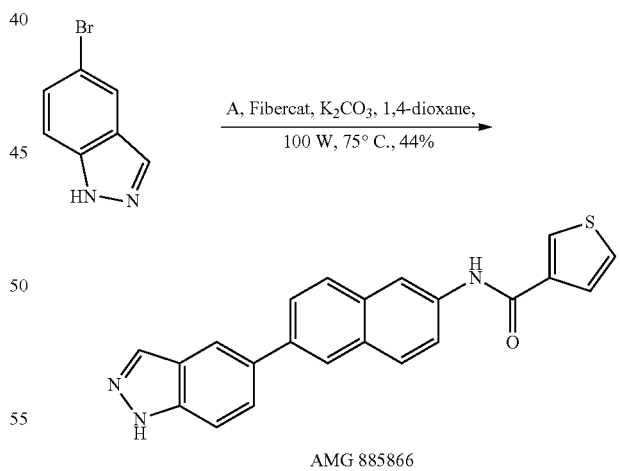

AMG 885866

N-(6-(1H-indazol-5-yl)naphthalen-2-yl)thiophene-3-carboxamide 5-bromo-1H-indazole (21 mg, 0.087 mmol), N-(6-(4,4,5, 5-tetramethyl-1,3,2-dioxaborolan-2-yl)naphthalen-2-yl) thiophene-3-carboxamide (50 mg, 0.13 mmol), Fibrecat palladium catalyst (Johnson-Matthey, 2.5 mg), and $K_2CO_3$ (2 M in water, 0.25 ml, 0.5 mmol) were combined in a microwave reaction vessel and 1,4-dioxane (2 ml) was added. The reaction tube was sealed and heated in the microwave (CEM microwave) at 50 Watts and 80 C for 10 minutes. The reaction was then cooled to room temperature, and more Fibercat palladium catalyst (8 mg) was added, along with 2 M $Na_2CO_3$ (0.25 ml). The reaction was heated in the microwave at 100 C and 75 Watts for 10 minutes, and then re-cooled to room temperature. The reaction was then diluted with water and methylene chloride, and the organic layer was separated, dried over sodium sulfate, filtered, concentrated, and treated with methylene chloride to afford a precipitate. This suspension was filtered, and the solid was collected to afford the title compound (14 mg, 44%). MS (ESI pos. ion) m/z: 370 (M+H). Calc'd Exact Mass for $C_{22}H_{15}N_3OS$: 369.

again separated, dried over sodium sulfate, filtered through a short plug of silica gel, and concentrated to give 17 g of intermediate product.

8.5 grams of this crude material was treated with glacial HOAc (54 ml) and aqueous HBr (40%, 270 ml) and stirred at 130 C for 1.5 hours. The reaction was immediately filtered while still hot through Celite, and the filtrate was cooled to room temperature and then cooled in an ice water bath. The precipitate was collected by filtration. This procedure was repeated on the rest of the material from the first reaction, and the total precipitate collected was 9.32 g (84%) of the title compound. MS (ESI pos. ion) m/z: 311 (M+H). Calc'd Exact Mass for $C_{18}H_{15}FN_2O_2$: 310.

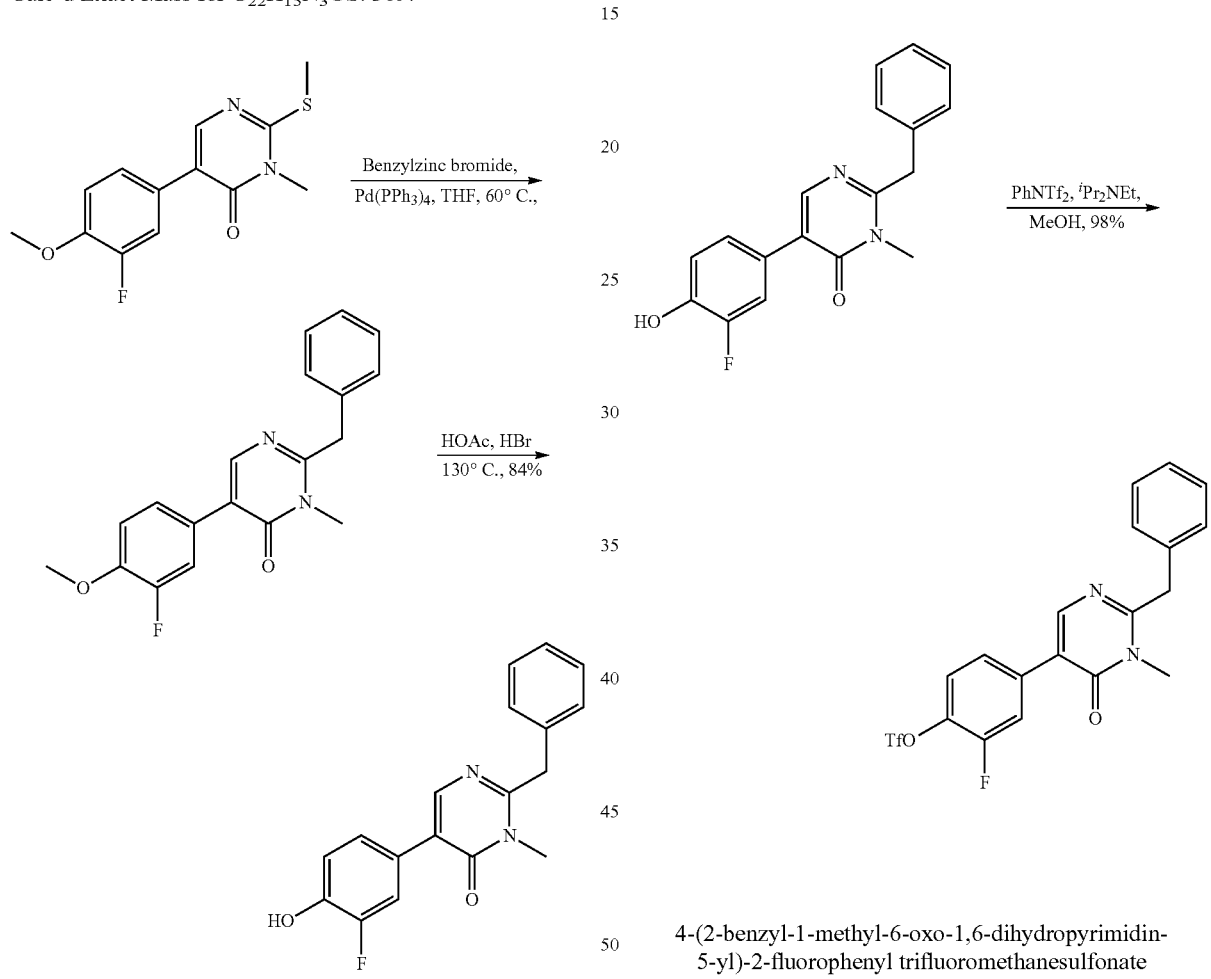

4-(2-benzyl-1-methyl-6-oxo-1,6-dihydropyrimidin-5-yl)-2-fluorophenyl trifluoromethanesulfonate 2-benzyl-5-(3-fluoro-4-hydroxyphenyl)-3-methylpyrimidin-4(3H)-one 5-(3-fluoro-4-methoxyphenyl)-3-methyl-2-(methylthio)pyrimidin-4(3H)-one (10.0 g, 36 mmol) and Pd(PPh₃)₄ (4.5 g, 3.9 mmol) were dissolved in THF and benzylzinc bromide (0.5 M in THF, 100 ml, 49 mmol) was added. The reaction was heated in a preheated oil bath (60 C) and stirred for 2 hours. The reaction was then cooled to room temperature, quenched with saturated ammonium chloride (100 ml), and diluted with chloroform and water. The organic layer was separated, washed with brine, and filtered through a pad of celite. The filtrate was concentrated, dissolved in chloroform, and washed with saturated EDTA. The chloroform layer was 2-benzyl-5-(3-fluoro-4-hydroxyphenyl)-3-methylpyrimidin-4(3H)-one (100 mg, 0.323 mmol) and $^i$Pr₂NEt (0.053 ml, 0.30 mmol) were suspended in MeOH (1.5 ml) and PhNTf₂ (173 mg, 0.484 mmol) was added. The reaction was stirred at room temperature for one hour and then concentrated. The same reaction was run using 2-benzyl-5-(3-fluoro-4-hydroxyphenyl)-3-methylpyrimidin-4(3H)-one (300 mg) and $^i$Pr₂NEt (0.15 ml) in MeOH (3 ml) and PhNTf₂ (245 mg). After 1 hour, more $^i$Pr₂NEt (0.1 ml) and PhNTf₂ (100 mg) were added. Stirring was continued for another hour and this reaction was also concentrated. Both were combined and purified using the ISCO purification system (40 g column, 0->5% MeOH/CH₂Cl₂) to afford title compound (0.53 g, 98%). MS (ESI pos. ion) m/z: 443 (M+H). Calc'd Exact Mass for $C_{19}H_{14}F_4N_2O_4S$: 442.

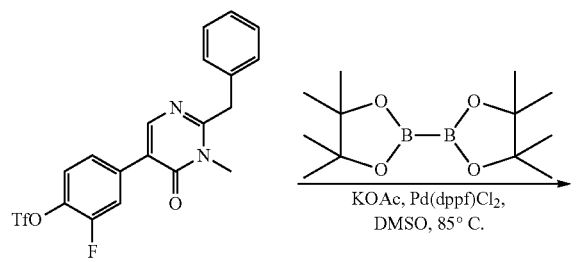

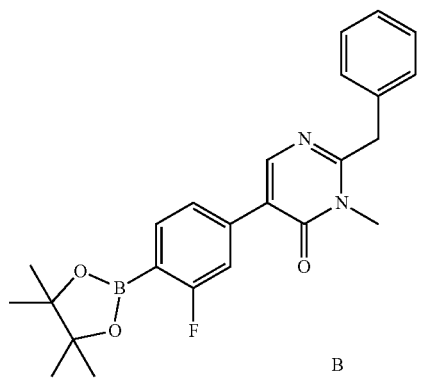

2-benzyl-5-(3-fluoro-4-(4,4,5,5-tetramethyl-1,3,2-dioxaborolan-2-yl)phenyl)-3-methylpyrimidin-4(3H)-one (B)

4-(2-benzyl-1-methyl-6-oxo-1,6-dihydropyrimidin-5-yl)-2-fluorophenyl trifluoromethanesulfonate (330 mg, 0.78 mmol), bispinacolatoborane (218 mg, 0.86 mmol), KOAc (230 mg, 2.3 mmol) and Pd(dppf)Cl$_2$ (32 mg, 0.039 mmol) were combined in DMSO and heated to 85 C. The reaction was stirred and then cooled to room temperature and diluted with methylene chloride and washed with water. The organic layer was dried over sodium sulfate, filtered through celite, and concentrated to give crude boronate ester, along with some of the corresponding boronic acid. This mixture was used for subsequent Suzuki couplings.

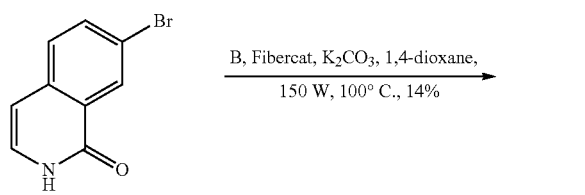

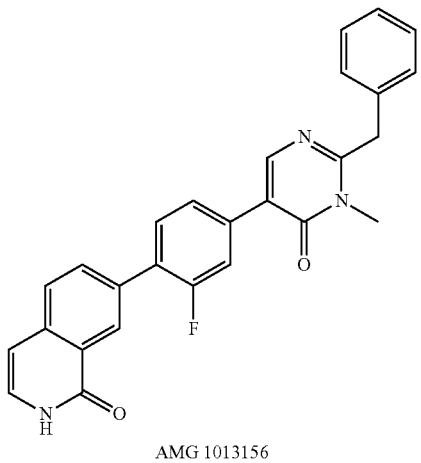

7-(4-(2-benzyl-1-methyl-6-oxo-1,6-dihydropyrimidin-5-yl)-2-fluorophenyl)isoquinolin-1(2H)-one 7-bromoisoquinolin-1(2H)-one (20 mg, 0.089 mmol), N-(6-(4,4,5,5-tetramethyl-1,3,2-dioxaborolan-2-yl)naphthalen-2-yl)thiophene-3-carboxamide (50 mg), Fibercat palladium catalyst (Johnson-Matthey, 8 mg), and K$_2$CO$_3$ (2 M in water, 0.25 ml, 0.5 mmol) were combined in a microwave reaction vessel and 1,4-dioxane (2 ml) was added. The reaction tube was sealed and heated in the microwave (CEM microwave) at 150 Watts and 100 C for 10 minutes. The reaction was cooled to room temperature and diluted with water and dichloromethane. The organic extracts were combined, dried over sodium sulfate, filtered, concentrated, and purified using the ISCO purification system (40 g column, 0->5% MeOH/CH$_2$Cl$_2$) to afford title compound (5.5 mg, 14%). MS (ESI pos. ion) m/z: 438 (M+H). Calc'd Exact Mass for C$_{27}$H$_{20}$FN$_3$O$_2$: 437.

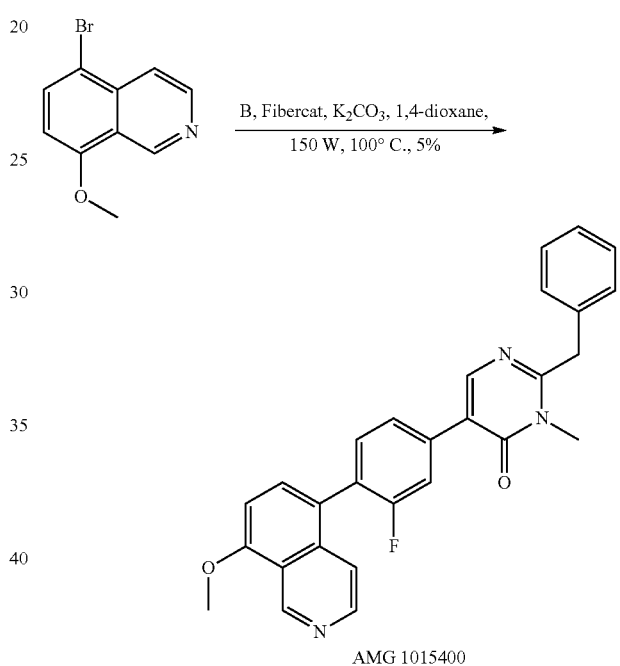

2-benzyl-5-(3-fluoro-4-(8-methoxyisoquinolin-5-yl)phenyl)-3-methylpyrimidin-4(3H)-one 5-bromo-8-methoxyisoquinoline (56 mg, 0.235 mmol), N-(6-(4,4,5,5-tetramethyl-1,3,2-dioxaborolan-2-yl)naphthalen-2-yl)thiophene-3-carboxamide (~100 mg), Fibercat palladium catalyst (Johnson-Matthey, 10 mg), and K$_2$CO$_3$ (2 M in water, 0.25 ml, 0.5 mmol) were combined in a microwave reaction vessel and 1,4-dioxane (2 ml) was added. The reaction tube was sealed and heated in the microwave (CEM microwave) at 150 Watts and 100 C for 10 minutes. The reaction was cooled to room temperature and diluted with water and dichloromethane. The organic extracts were combined, dried over sodium sulfate, filtered, concentrated, and purified two times using the ISCO purification system (40 g column, 0->5% MeOH/CH$_2$Cl$_2$) and one time using Varian prep HPLC (1%-95% MeCN/water with 0.1% TFA over 70 minutes) to afford title compound (5 mg, 5%) contaminated with about 2 mg of the corresponding phenol. MS (ESI pos. ion) m/z: 452 (M+H). Calc'd Exact Mass for C$_{28}$H$_{22}$FN$_3$O$_2$: 451.

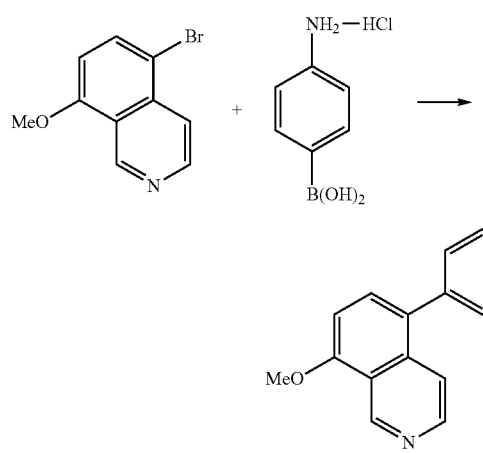

4-(5-methoxynaphthalen-1-yl)benzenamine

To a mixture of 1-bromo-5-methoxynaphthalene[1] (320 mg, 1.3 mmol) and 4-aminophenylboronic acid (HCl salt, 320 mg, 1.85 mmol) in dioxane (3 mL)-$H_2O$ (3 mL) was added $PdCl_2$ (dppf)-dichloromethane (53 mg, 0.063 mmol) and $Na_2CO_3$ (530 mg, 4.2 mmol). The mixture was heated to 100° C. for 12 h and cooled to room temperature. The mixture was extracted with dichloromethane and the organic phase was dried over $Na_2SO_4$, concentrated, and purified on silica with 5% (2N $NH_3$ in MeOH) in dichloromethane to afford the product as a tan solid (300 mg, 89%). MS (ESI pos. ion) m/z: 251 (M+H).

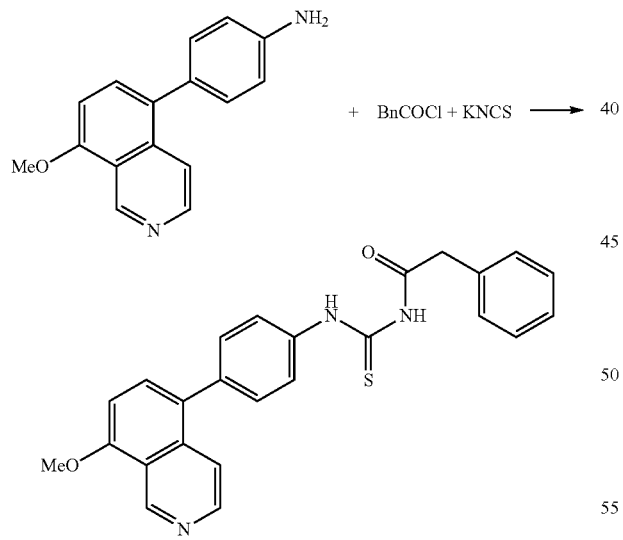

1-(4-(8-methoxyisoquinolin-5-yl)phenyl)-3-(2-phenylacetyl)thiourea

N-(4-(8-methoxyisoquinolin-5-yl)phenyl)-2-phenylacetamide

A solution of 4-(5-methoxynaphthalen-1-yl)benzenamine (140 mg, 0.56 mmol) and 2-phenylethanoyl isothiocyanate (320 mg, 1.98 mmol), prepared by condensing 2-phenylacetyl chloride and isothiocyanatopotassium in MeCN at 80° C., in MeOH (5 mL) was stirred at room temperature overnight. The reaction mixture quenched with $NaHCO_3$ (aq. 10 mL) and extracted with dichloromethane 3×5 mL. The combined organic phase was dried over $Na_2SO_4$, and concentrated, and purified on silica with 3% MeOH in dichloromethane to afford 1-(4-(8-methoxyisoquinolin-5-yl)phenyl)-3-(2-phenylacetyl)thiourea as a yellow solid (25 mg, 11%). MS (ESI pos. ion) m/z: 428 (M+H).

[1] (a) Hendrickson, J. B.; Radriguez, C. *J. Org. Chem.* 1983, 48, 3344-3346. (b) S-Y Sit, et al. *Bioorg. Med. Chem.*, 2004, 12, 715-736.

N-(4-(8-methoxyisoquinolin-5-yl)phenyl)-2-phenylacetamide was isolated from the above reaction as a yellow solid (122 mg, 59%). MS (ESI pos. ion) m/z: 369 (M+H).

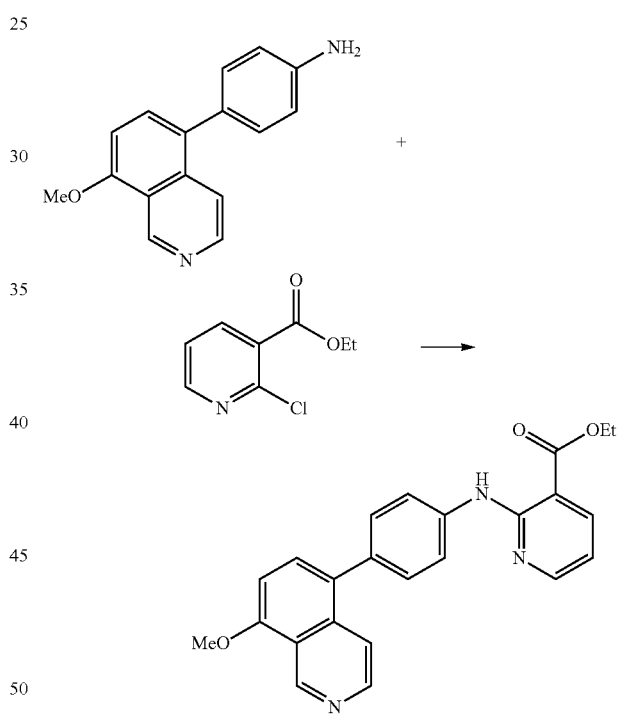

Ethyl 2-(4-(8-methoxyisoquinolin-5-yl)phenylamino)nicotinate

A mixture of 4-(8-methoxyisoquinolin-5-yl)benzenamine (690 mg, 2.7 mmol), 2-chloronicotinaten (750 mg, 4.0 mmol), Pd(OAc)$_2$ (30 mg, 0.13 mmol), BINAP (107 mg, 0.17 mmol), and $K_2CO_3$ (750 mg, 5.4 mmol) in PhMe (3 mL) under nitrogen was heated to 110° C. for 16 h. The mixture was cooled to room temperature and diluted with water (10 mL). The slurry was filtered and washed with water (3×5 mL) and then 1:1 hexane-EtOAc (20 mL). The resulting solid was further triturated with ether (2×5 mL), MeOH (5 mL), and EtOAc (5 mL) to yield the product as a yellow solid (450 mg, 41%). MS (ESI pos. ion) m/z: 400 (M+H).

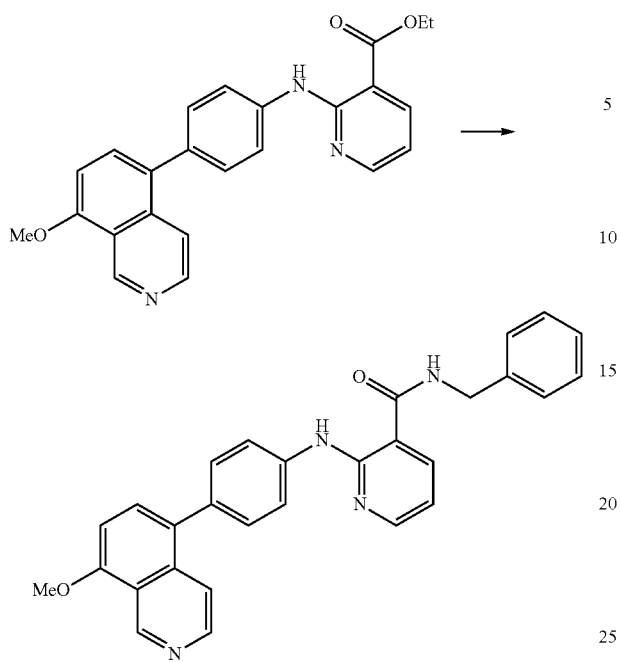

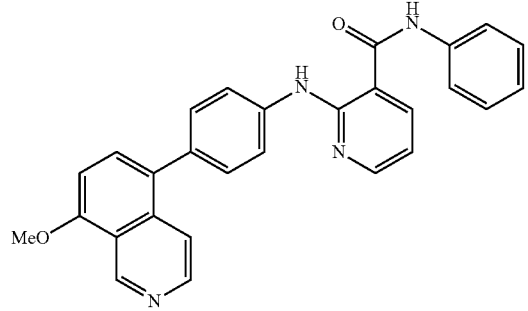

2-(4-(8-methoxyisoquinolin-5-yl)phenylamino)-N-phenylnicotinamide

Similar reaction as step 2 of last reaction with aniline (0.5 mL) afforded the desired product (19 mg, 3%). MS (ESI pos. ion) m/z: 447 (M+H).

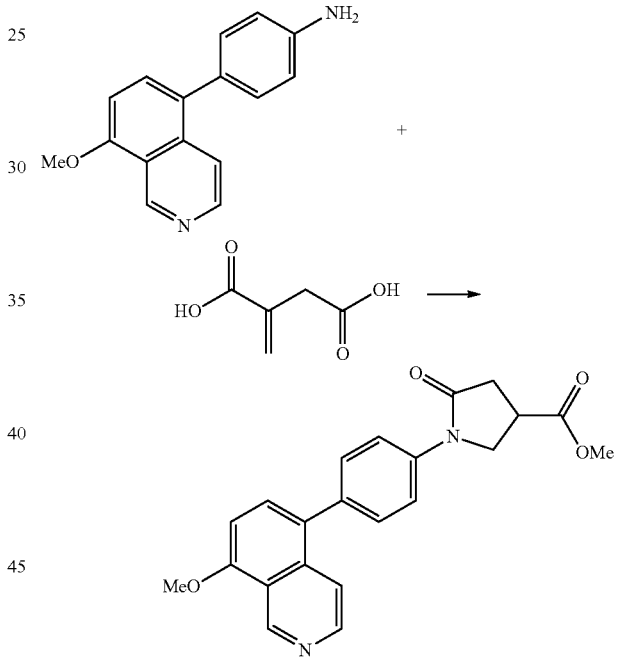

N-benzyl-2-(4-(8-methoxyisoquinolin-5-yl)phenylamino)nicotinamide

Step 1: A suspension of Ethyl 2-(4-(8-methoxyisoquinolin-5-yl)phenylamino)nicotinate (430 mg, 1.08 mmol) in MeOH (5 mL) and dioxane (2 mL) was treated with NaOH (1 N, 2 mL) and the mixture was heated to 60° C. for 2 h. The mixture was cooled to room temperature and filtered through a pad of Celite. The filtrate was concentrated to a yellow solid which was neutralized with HCl (0.2 N) to pH ~7. The slurry was filtered and dried in the air to afford the acid as a brown solid (430 mg). The acid was mixed with carbonyl diimidazole (400 mg, 2.4 mmol) in DMF (2 mL). The mixture was heated to 80° C. for 5 h and cooled to room temperature. The acylimidazole thus prepared was divided to two equal portions.

Step 2: One portion of the acid solution from step 1 was treated with benzylamine (0.5 mL). The mixture was stirred at room temperature for two days and was diluted with EtOAc (20 mL). The mixture was washed with NaOH (1 N, 5 mL), H$_2$O (5 mL), brine (5 mL), and dried over Na$_2$SO$_4$. The solvent was evaporated and the resulting solid was purified on silica with 2% (2N NH$_3$ in MeOH) in dichloromethane, followed by preparative TLC using 5% (2N NH$_3$ in MeOH) in dichloromethane to afford the product (57 mg, 9%). MS (ESI pos. ion) m/z: 461 (M+H).

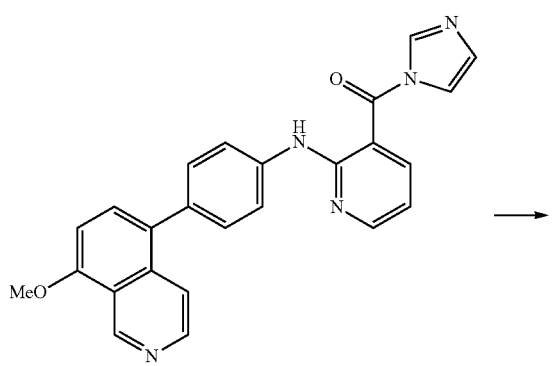

methyl 1-(4-(8-methoxyisoquinolin-5-yl)phenyl)-5-oxopyrrolidine-3-carboxylate

A mixture of 4-(8-methoxyisoquinolin-5-yl)benzenamine (600 mg, 2.4 mmol) and 2-methylenesuccinic acid (320 mg, 2.46 mmol) in dichloromethane (5 mL) was heated gradually to 100° C. and continued overnight. The melt was cooled to room temperature and was dissolved in MeOH-dichloromethane (1:1, 5 mL). SOCl$_2$ (2 mL) was added slowly and the reaction mixture was stirred at room temperature for 2 h. The mixture was diluted with dichloromethane (40 mL) and the mixture was washed with H$_2$O, NaHCO$_3$ (sat), dried over Na$_2$SO$_4$, and concentrated. Flash chromatography on silica with 1% (2 N NH$_3$ in MeOH) in EtOAc afforded the product as a white solid (220 mg, 24%). MS (ESI pos. ion) m/z: 377 (M+H).

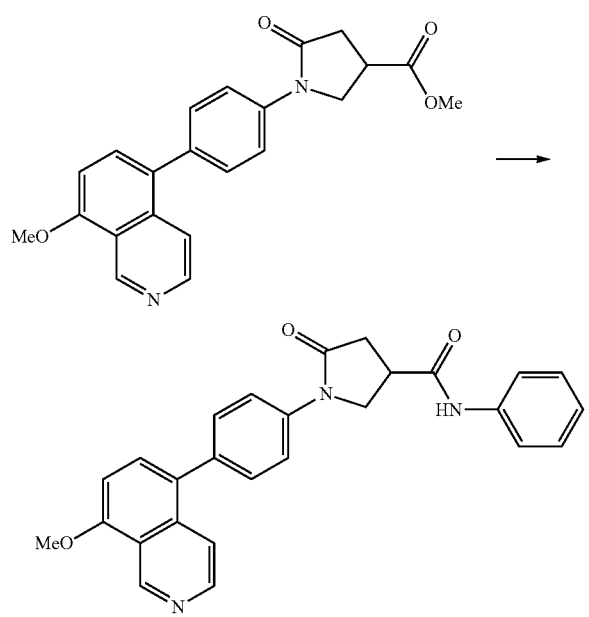

1-(4-(8-methoxyisoquinolin-5-yl)phenyl)-5-oxo-N-phenylpyrrolidine-3-carboxamide

Step 1: 1-(4-(8-methoxyisoquinolin-5-yl)phenyl)-5-oxopyrrolidine-3-carboxylic acid A mixture of methyl 1-(4-(8-methoxyisoquinolin-5-yl)phenyl)-5-oxopyrrolidine-3-carboxylate (220 mg, 0.58 mmol) in dioxane (2 mL) was treated with NaOH (1N, 1 mL). The mixture was heated to 80° C. for 17 h and the solvents were evaporated to dryness. MS (ESI pos. ion) m/z: 363 (M+H). The acid was dissolved in DMF (2 mL) and was treated with HBTU (450 mg, 1.25 mmol) and Et₃N (1 mL). The solution was divided into two equal portions and was used directly.

Step 2: The acid solution was treated with aniline (0.2 mL) and the reaction was let go overnight. The mixture was diluted with NaHCO₃ (half sat., 10 mL) and was extracted with dichloromethane (3×6 mL). The combined organic phase was dried over Na₂SO₄, and concentrated. Flash chromatography on silica with 0-5% MeOH in EtOAc afforded the product as an oil (140 mg). MS (ESI pos. ion) m/z: 438 (M+H).

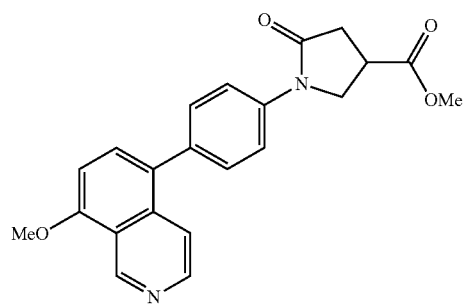

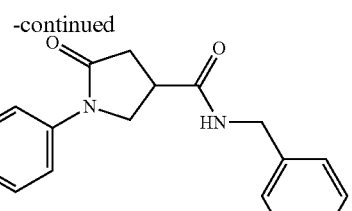

N-benzyl-1-(4-(8-methoxyisoquinolin-5-yl)phenyl)-5-oxopyrrolidine-3-carboxamide

Similarly the second portion of acid from step 2, above, was treated with benzyl amine (0.2 mL) and after similar workup, afforded the product as a white solid (90 mg, 70%). MS (ESI pos. ion) m/z: 352 (M+H).

Examples 33-39

Example compounds 33 to 39 were synthesized using the following general procedure:

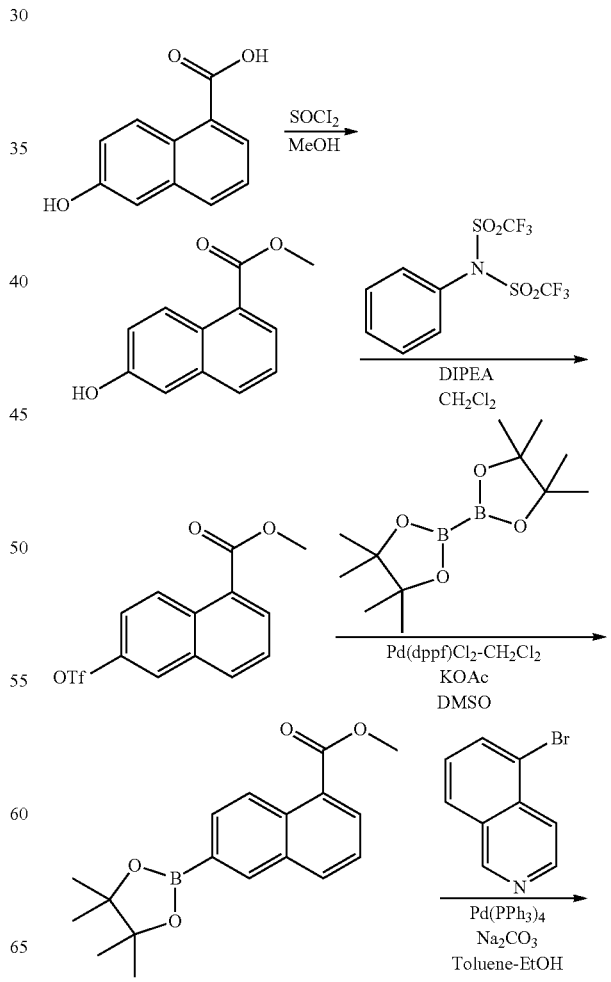

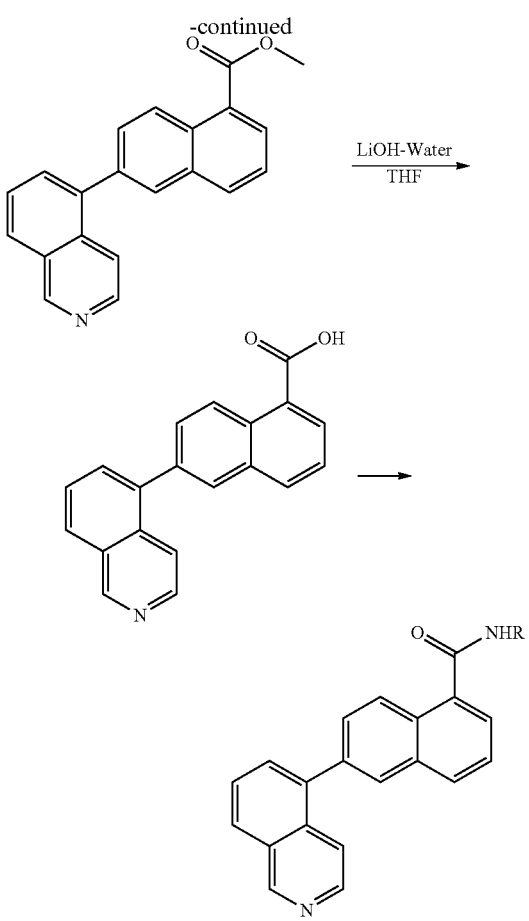

Methyl 6-hydroxy-1-naphthoate

To a solution of 6-Hydroxy-1-naphthoic acid (6.9 g. 37 mmol) in 200 mL of MeOH at 0° C. was added drop wise over 5 minutes thionyl chloride (3.26 mL). The resulting mixture was stirred overnight at room temperature and another 2.5 mL of Thionyl chloride was added and mixture was stirred at room temperature. Solvent was evaporated and residue was dried under vacuo to give 7.49 g the title compound as a brown solid.

Methyl 6-(trifluoromethylsulfonyloxy)-1-naphthoate

To a 0° C. solution of Methyl 6-hydroxy-1-naphthoate (2.94 g, 14.5 mmol) in 100 mL of $CH_2Cl_2$ was added Diisopropylethylamine (6.34 mL, 36.37 mmol) followed by N-Phenyltrifluoromethane-sulphonimide (10.39 g, 29.09 mmol). The resulting mixture was warmed to room temperature and stirred overnight. Solvent was evaporated and residue was purified by chromatography (Hexanes->4.5:1 Hexanes:$CH_2Cl_2$->4:1 $CH_2Cl_2$:Hexanes) to give 4.7 g of the title compound as a white solid.

Methyl 6-(4,4,5,5-tetramethyl-1,3,2-dioxaborolan-2-yl)-1-naphthoate

Methyl 6-(trifluoromethylsulfonyloxy)-1-naphthoate (2.58 g, 7.7 mmol), 4,4,5,5-tetramethyl-2-(4,4,5,5-tetramethyl-1,3,2-dioxaborolan-2-yl)-1,3,2-dioxaborolane (2.1 g, 8.12 mmol), potassium acetate (2.27 g, 23 mmol) were placed in DMSO (36 mL) and then Pd(dppf)$_2$Cl$_2$ (170 mg, 0.23 mmol) was added. Mixture was stirred at 80° C. overnight and then cooled to room temperature. Water was added and the mixture was extracted with ethyl acetate. Organic phase was dried, filtered and evaporated. Residue was purified by chromatography (3:1 hexanes-$CH_2Cl_2$->4:1 $CH_2Cl_2$-hexanes->1:2 ethyl acetate-hexanes) to give 2.2 g of the title compound.

Methyl 6-(isoquinolin-5-yl)-1-naphthoate

Methyl 6-(4,4,5,5-tetramethyl-1,3,2-dioxaborolan-2-yl)-1-naphthoate (2.2 g, 7.0 mmol), 5-Bromoisoquinoline (1.33 g, 6.3 mmol), a 2M solution of sodium carbonate (9.6 mL) and palladium tetrakistriphenylphospine (0.37 g, 0.32 mmol) were heated in Toluene-EtOH (105 mL-21 mL) at 80° C. overnight. Solvent was evaporated and mixture was extracted with ethyl acetate. Organic phase was washed with brine, dried, filtered and evaporated. Residue was purified by chromatography (ethyl acetate-hexane 10:90->20:80->30:70->40:60->60-40. to give 1.4 g of the title compound as an off-white solid

6-(isoquinolin-5-yl)-1-naphthoic acid

To a solution of Methyl 6-(isoquinolin-5-yl)-1-naphthoate (1.4 g, 4.4 mmol) in THF (445 mL) was added 1N LiOH (89 mL) and the resulting mixture was stirred at room temperature. The mixture was concentrated down to a small aqueous volume, which was acidified to pH 5 with conc HCl. The solid was isolated by filtration, washed with a small amount of water and dried overnight under vacuum to give 1.65 g of the titled compound.

6-(isoquinolin-5-yl)-1-naphthoyl chloride 6-(isoquinolin-5-yl)-1-naphthoic acid (0.123 g, 0.4 mmol) was suspended in $CH_2Cl_2$ (15 mL) and oxallyl chloride was (0.036 mL, 0.4 mmol) was added followed by a drop of DMF. The resulting mixture was stirred at room temperature overnight and the solvent was evaporated to give a solid. The solid was dried under vacuum.

Preparation 1

N-(4-chlorophenyl)-6-(isoquinolin-5-yl)-1-naphthamide

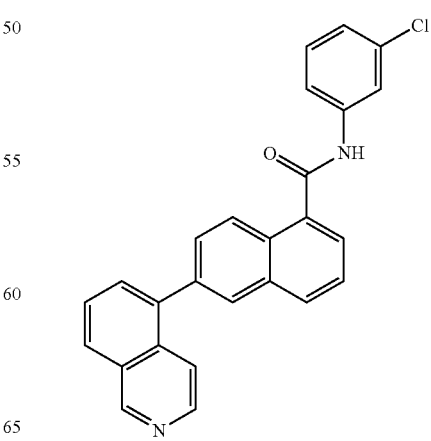

6-(isoquinolin-5-yl)-1-naphthoyl chloride (0.85 g, 0.27 mmol) was suspended in CH$_2$Cl$_2$ (1 mL) and triethylamine (0.057 mL, 0.4 mmol) was added followed by 4-chloroaniline (33 mg, 0.26 mol). The mixture was stirred at room temperature for 2 h, 0.1 mL of DMF was added and the mixture was stirred for an additional 72 h. A solution of aqueous NaHCO$_3$ was added and mixture was extracted with CH$_2$Cl$_2$. Organic phase was dried, filtered and evaporated. Residue was purified by prep plate (ethyl acetate) to give a white solid. MS (ESI pos. ion) m/z: 409 (M+H). Calc'd Exact Mass for C$_{26}$H$_{17}$ClN$_2$O: 408.

Example 33

N-(4-tert-butylphenyl)-6-(isoquinolin-5-yl)-1-naphthamide

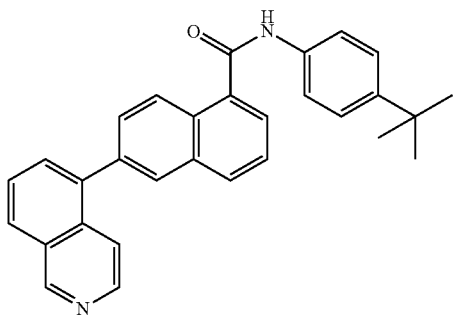

N-(4-tert-butylphenyl)-6-(isoquinolin-5-yl)-1-naphthamide was prepared similarly to the preparation 1 to give the title compound as a solid. MS (ESI pos. ion) m/z: 431.2 (M+H). Calc'd Exact Mass for C$_{30}$H$_{26}$N$_2$O: 430.

Example 34

N-(4-isopropylphenyl)-6-(isoquinolin-5-yl)-1-naphthamide

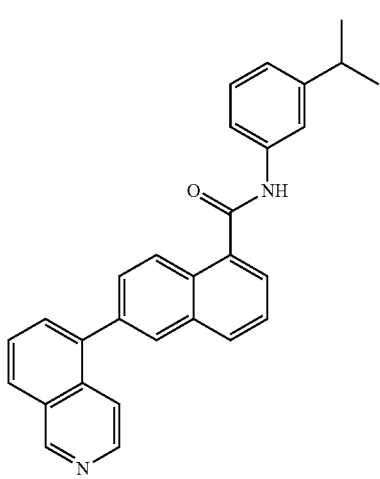

N-(4-isopropylphenyl)-6-(isoquinolin-5-yl)-1-naphthamide was prepared similarly to the preparation 1 to give the title compound as a solid. MS (ESI pos. ion) m/z: 417. (M+H). Calc'd Exact Mass for C$_{29}$H$_{24}$N$_2$O: 416.

Example 35

6-(isoquinolin-5-yl)-N-(4-(trifluoromethyl)phenyl)-1-naphthamide

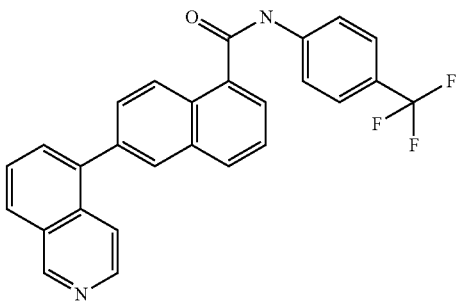

6-(isoquinolin-5-yl)-N-(4-(trifluoromethyl)phenyl)-1-naphthamide was prepared similarly to the preparation 1 to give the title compound as a solid. MS (ESI pos. ion) m/z: 443. (M+H). Calc'd Exact Mass for C$_{27}$H$_{17}$F$_3$N$_2$O: 442

Example 36

6-(isoquinolin-5-yl)-1-naphthamide

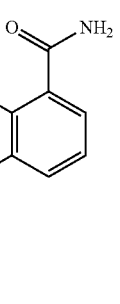

6-(isoquinolin-5-yl)-1-naphthoic acid (0.86 mg, 0.29 mmol) was suspended in CH$_2$Cl$_2$ (2 mL) and oxallyl chloride (0.038 mL, 0.4 mmol) was added followed by a drop of DMF. Mixture was stirred at room temperature for 3 h and solvent was evaporated and residue dried under vacuum. The crude acid chloride was dissolved in a solution of NH$_3$ in dioxane and was stirred at room temperature. Solvent was evaporated, a solution of aqueous NaHCO$_3$ was added and the mixture was extracted with CH$_2$Cl$_2$ and then with ethyl acetate. Residue was purified by prep plate (5% MeOH/CH$_2$Cl$_2$) to give the title compound as a solid. MS (ESI pos. ion) m/z: 299. (M+H). Calc'd Exact Mass for C$_{20}$H$_{14}$N$_2$O: 298.

Example 37

6-(isoquinolin-5-yl)-N-(methoxymethyl)-1-naphthamide

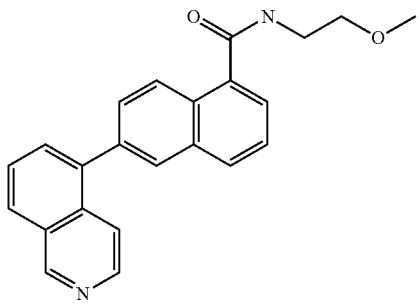

6-(isoquinolin-5-yl)-N-(methoxymethyl)-1-naphthamide was prepared similarly to the preparation V to give the title compound as a solid. MS (ESI pos. ion) m/z: 357. (M+H). Calc'd Exact Mass for $C_{23}H_{20}N_2O_2$: 356.

Example 38

6-(isoquinolin-5-yl)-N-(thiazol-2-yl)-1-naphthamide

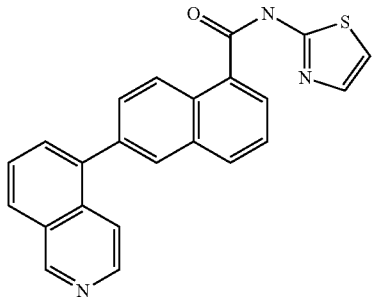

6-(isoquinolin-5-yl)-1-naphthoic acid (55 mg, 0.18 mmol), 2-aminothiazole (24 mg, 0.23 mmol), DIPEA (0.048 mL, 0.27 mmol) and HATU (0.1 g, 0.27 mmol) were stirred in CHCl$_3$ (1 mL) at room temperature overnight. The solid formed was filtered, rinsed with CHCl$_3$, MeOH and dried under vacuum to give the titled compound as a solid. MS (ESI pos. ion) m/z: 382. (M+H). Calc'd Exact Mass for $C_{23}H_{15}N_3OS$: 381.

Example 39

6-(isoquinolin-5-yl)-N-phenyl-1-naphthamide

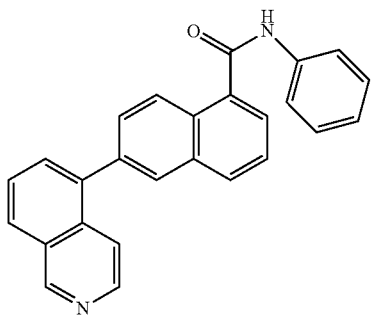

6-(isoquinolin-5-yl)-N-phenyl-1-naphthamide was prepared similarly to the preparation VII to give the title compound as an off-white solid. MS (ESI pos. ion) m/z: 375. (M+H). Calc'd Exact Mass for $C_{26}H_{18}N_2O$: 374.

Biological Testing

The efficacy of the compounds of the invention as inhibitors of Lck, VEGFR and/or HGF related activity are demonstrated as follows.

c-Met Receptor Assay

Cloning, Expression and Purification of c-Met Kinase Domain

A PCR product covering residues 1058-1365 of c-Met (c-Met kinase domain) is generated from Human Liver QuickClone™ cDNA (Invitrogen) using forward primer 5'-ATTGACGGATCCATGCTAAATCCA-GAGCTGGTCCAGGCA-3' (SEQ ID NO. 1) and reverse primer 5'-ACAACAGAATTCAATACGGAGCGACA-CATTTTACGTT-3' (SEQ ID NO. 2). The PCR product is cloned into a modified pFastBac1 expression vector (harboring the gene for *S. japonicum* glutathione S-transferase immediately upstream of the multiple cloning site) using standard molecular biological techniques. The GST-c-Met kinase domain fusion (GST-Met) gene is transposed into full-length baculovirus DNA using the BacToBac™ system (Invitrogen). High 5 cells are infected with the recombinant baculovirus for 72 h at 27° C. The infected cells are harvested by centrifugation and the pellet is stored at −80° C. The pellet is resuspended in buffer A (50 mM HEPES, pH 8.0, 0.25 M NaCl, 10 mM 2-mercaptoethanol, 10% (w/v) glycerol, 0.5% (v/v) protease inhibitor cocktail (Sigma P8340), stirred at 4° C. to homogeneity, and the cells are disrupted by microfluidization (Microfluidics) at 10,000 psi. The resulting lysate is centrifuged at 50,000×g for 90 min at 4° C., and the supernatant is adsorbed onto 10 mL of glutathione Sepharose™ 4B (Amersham) by batch method. The slurry is rocked gently overnight at 4° C. The glutathione resin is harvested by centrifugation and washed three times with 40 mL buffer A by batch method. The resin is washed three times with buffer B (buffer A adjusted to 0.1 M NaCl, less protease inhibitors). The protein is eluted with buffer B containing 25 mM reduced glutathione. Eluted fractions are analyzed by SDS-PAGE and concentrated to <10 mL (~10 mg/mL total protein). The concentrated protein is separated by Superdex™ 200 (Amersham) size exclusion chromatography in buffer C (25 mM Tris, pH 7.5, 0.1 M NaCl, 10 mM 2-mercaptoethanol, 10% glycerol). The fractions are analyzed by SDS-PAGE and the appropriate fractions are pooled and concentrated to ~1 mg/mL. The protein is aliquotted and stored at −80° C.

Alternative Purification of Human GST-cMET from Baculovirus Cells

Baculovirus cells are broken in 5×(volume/weight) of Lysis Buffer (50 mM HEPES, pH 8.0, 0.25 M NaCl, 5 mM mercaptoethanol, 10% glycerol plus Complete Protease Inhibitors (Roche (#10019600), 1 tablet per 50 mL buffer). The lysed cell suspension is centrifuged at 100,000×g (29, 300 rpm) in a Beckman ultracentrifuge Ti45 rotor for 1 h. The supernatant is incubated with 10 ml of Glutathione Sepharose 4B from Amersham Biosciences (#27-4574-01). Incubation is carried out overnight in a cold room (approximately 8° C.). The resin and supernatant is poured into an appropriately sized disposable column and the flow through supernatant was collected. The resin is washed with 10 column volumes (100 mL) of Lysis Buffer. The GST-cMET is eluted with 45 mL of 10 mM Glutathione (Sigma #G-4251) in Lysis Buffer. The elution is collected as 15 mL fractions. Aliquots of the elution fractions are run on SDS PAGE (12% Tris Glycine gel, Invitrogen, #EC6005BOX). The gel is stained with 0.25% Coomassie Blue stain. Fractions with GST-cMET are concentrated with a Vivaspin 20 mL Concentrator (#VS2002; 10,00 MW cutoff) to a final volume less than 2.0 ml. The concentrated GST-cMET solution is applied to a Superdex 75 16/60 column (Amersham Biosciences #17-1068-01) equilibrated with 25 mM Tris, pH 7.5, 100 mM NaCl, 10 mM mercaptoethanol, 10% glycerol. The GST-cMET is eluted with an isocratic run of the above buffer, with the eluent collected in 1.0 mL fractions. Fractions with significant $OD_{280}$ readings are run on another 12% Tris Glycine gel. The peak tubes with GST-cMET are pooled and the $OD_{280}$ is read with the column buffer listed above as the blank buffer.

Phosphorylation of the purified GST-cMET is performed by incubating the protein for 3 h at RT with the following:

| | Final concentration |
|---|---|
| a) 100 mM ATP (Sigma #A7699) | 25 mM |
| b) 1.0 M MgCl$_2$ (Sigma #M-0250) | 100 mM |
| c) 200 mM Sodium Orthovanadate (Sigma #S-6508) | 15 mM |
| d) 1.0 M Tris-HCl, pH 7.00 (in house) | 50 mM |
| e) H$_2$0 | |
| f) GST-cMET | 0.2-0.5 mg/mL |

After incubation, the solution is concentrated in a Vivaspin 20 mL Concentrator to a volume less than 2.00 mL. The solution is applied to the same Superdex 75 16/60 column used above after re-equilibration. The GST-cMET is eluted as described above. The elution fractions corresponding to the first eluted peak on the chromatogram are run on a 12% Tris Glycine gel, as above, to identify the fractions with GST-cMET. Fractions are pooled and the $OD_{280}$ is read with the column buffer used as the blank.

A Kinase reaction Buffer is prepared as follows:

| | | | Per 1 L |
|---|---|---|---|
| 60 mM HEPES $_p$H 7.4 | 1 M stock | 16.7 X | 60 mL |
| 50 mM NaCl | 5 M stock | 100 X | 10 mL |
| 20 mM MgCl$_2$ | 1 M stock | 50 X | 20 mL |
| 5 mM MnCl$_2$ | 1 M stock | 200 X | 5 mL |

When the assay is carried out, freshly add:

| | | |
|---|---|---|
| 2 mM DTT | 1 M stock | 500 X |
| 0.05% BSA | 5% stock | 100 X |
| 0.1 mM Na$_3$OV$_4$ | 0.1 M stock | 1000 X |

The HTRF buffer contains:
50 mM Tris-HCl ($_p$H 7.5), 100 mM NaCl, 0.1% BSA, 0.05% Tween 20.5 mM EDTA Fresh add SA-APC (PJ25S Phycolink Streptavidin-Allophycocyanin Conjugate, Prozyme Inc.) and Eu-PT66 (Eu-W1024 labeled anti-phosphorotyrosine antibody PT66, AD0069, Lot 168465, Perkin-Elmer Inc.) to reach the final concentration:
 0.1 nM final Eu-PT66
 11 nM final SA-APC Methods:
1. Dilute GST-cMet (P) enzyme in kinase buffer as follows:
Prepare 8 nM GST-cMet (P) working solution (7.32 µM to 8 nM, 915×, 10 µL to 9.15 mL). In a 96 well clear plate [Costar #3365] add 100 µL in eleven columns, in one column add 100 µL kinase reaction buffer alone.

2. Assay plate preparation:
Use Biomek FX to transfer 10 µL 8 nM GST-cMet (P) enzyme, 48.4 µL kinase reaction buffer, 1.6 µL compound (in DMSO) (Start concentration at 10 mM, 1 mM and 0.1 mM, sequential dilution 1:3 to reach 10 test points) in a 96 well costar clear plate [Costar #3365], mix several times. Then incubate the plate at RT for 30 min.

3. Prepare Gastrin and ATP working solution in kinase reaction buffer as follows: Prepare 4 µM Gastrin and 16 µM ATP working solution

| | | Per 10 mL |
|---|---|---|
| Gastrin 4 µM stock | (500 µM to 4 µM, 125 X) | 80 µL |
| ATP 16 µM stock | (1000 µM to 16 µM, 62.5 X) | 160 µL |

Use Biomek FX to Add 20 µl ATP and Gastrin Working Solution to the Assay Plate to Start Reaction, Incubate the Plate at RT for 1 h 4. Transfer 5 µL reaction product at the end of 1 h into 80 µL HTRF buffer in black plate [Costar #3356], read on Discover after 30 min incubation.
Assay Condition Summary:

| | |
|---|---|
| $K_M$ATP* | 6 µM |
| [ATP] | 4 µM |
| $K_M$Gastrin/p(EY) | 3.8 µM |
| [gastrin] | 1 µM |
| [enzyme] | 1 nM |

$K_M$ATP, $K_M$ gastrin for various enzymes were determined by HTRF/$^{33}$P labeling and HTRF methods.

c-Met Cell-Based Autophosphorylation Assay

Hunan PC3 and mouse CT26 cells are available obtained from ATCC. The cells were cultured in a growth medium containing RPMI 1640, penicillin/streptomycin/glutamine (1×) and 5% FBS. $2 \times 10^4$ cells in medium were plated per well in a 96 well plate and incubated at 37° C. overnight. The cells were serum-starved by replacing the growth media with basic medium (DMEM low glucose+0.1 BSA, 120 µL per well) at 37° C. for 16 h. Compounds (either 1 mM and 0.2 mM) in 100% DMSO were serially diluted (1:3) 3333 fold on a 96 well plate, diluting 1:3 with DMSO from column 1 to 11 (columns 6 and 12 receive no compound). Compound samples (2.4 µL per well) were diluted with basic medium (240 µL) in a 96 well plate. The cells were washed once with basic medium (GIBCO, DMEM 11885-076) then compound solution was added (100 µL). The cells were incubated at 37° C. for 1 h. A (2 mg/mL) solution of CHO-HGF (7.5 µL) was diluted with 30 mL basic medium to provide a final concentration of 500 ng/mL. This HGF-containing media (120 µL) was transferred to a 96 well plate. Compounds (1.2 µL) was added to the HGF-containing media and mixed well. The mixture of media/HGF/compound (100 μL) was added to the cells (final HGF concentration—250 ng/mL) then incubated at 37° C. for 10 min. A cell lysate buffer (20 mL) was prepared containing 1% Triton X-100, 50 mM Tris pH 8.0, 100 mM NaCl, Protease inhibitor (Sigma, #P-8340) 200 μL, Roche Protease inhibitor (Complete, #1-697-498) 2 tablets, Phosphatase Inhibitor II (Sigma, #P-5726) 200 μL, and a sodium vanadate solution (containing 900 μL PBS, 100 μL 300 mM NaVO$_3$, 6 μL H$_2$O$_2$ (30% stock) and stirred at RT for 15 min) (90 μL). The cells were washed once with ice cold 1×PBS (GIBCO, #14190-136), then lysis buffer (60 μL) was added and the cells were incubated on ice for 20 min.

The IGEN assay was performed as follows: Dynabeads M-280 streptavidin beads were pre-incubated with biotinylated anti-human HGFR (240 μL anti-human-HGFR (R&D system, BAF527 or BAF328) @ 100 μg/mL+360 μL Beads (IGEN #10029+5.4 μL buffer–PBS/1% BSA/0.1% Tween20) by rotating for 30 min at RT. Antibody beads (25 μL) were transferred to a 96 well plate. Cell lysate solution (25 μL) was transferred added and the plate was shaken at RT for 1 h. Anti-phosphotyrosine 4G10 (Upstate 05-321) (19.7 μL antibody+6 mL 1×PBS) (12.5 μL) was added to each well, then incubated for 1 h at RT. Anti-mouse IgG ORI-Tag (ORIGEN #110087) (24 μL Antibody+6 mL buffer) (12.5 μL) was added to each well, then incubated at RT for 30 min. 1×PBS (175 μL) was added to each well and the electrochemiluminescence was read by an IGEN M8. Raw data was analyzed using a 4-parameter fit equation in XLFit. IC$_{50}$ values are then determined using Grafit software. Examples 3-4, 9, 25-27, and 37-38 exhibited activity in PC3 cells with IC$_{50}$ values less than 1.0 μM. Examples 1, 3-4, 9, 25-27, and 38 exhibited activity in CT26 cells with IC$_{50}$ values less than 1.0 μM.

Human Umbilical Vein Endothelial cells are purchased from Clonetics, Inc., as cryopreserved cells harvested from a pool of donors. These cells, at passage 1, are thawed and expanded in EBM-2 complete medium, until passage 2 or 3. The cells are trypsinized, washed in DMEM+10% FBS+antibiotics, and spun at 1000 rpm for 10 min. Prior to centrifugation of the cells, a small amount is collected for a cell count. After centrifugation, the medium is discarded, and the cells are resuspended in the appropriate volume of DMEM+10% FBS+antibiotics to achieve a concentration of 3×10$^5$ cells/mL. Another cell count is performed to confirm the cell concentration. The cells are diluted to 3×10$^4$ cells/mL in DMEM+10% FBS+antibiotics, and 100 μL of cells are added to a 96-well plate. The cells are incubated at 37° C. for 22 h.

Prior to the completion of the incubation period, compound dilutions are prepared. Five-point, five-fold serial dilutions are prepared in DMSO, at concentrations 400-fold greater than the final concentrations desired. 2.5 μL of each compound dilution are diluted further in a total of 1 mL DMEM+10% FBS+antibiotics (400× dilution). Medium containing 0.25% DMSO is also prepared for the 0 μM compound sample. At the 22 h timepoint, the medium is removed from the cells, and 100 μL of each compound dilution is added. The cells are incubated at 37° C. for 2-3 h.

During the compound pre-incubation period, the growth factors are diluted to the appropriate concentrations. Solutions of DMEM+10% FBS+antibiotics, containing either VEGF or bFGF at the following concentrations: 50, 10, 2, 0.4, 0.08, and 0 ng/mL are prepared. For the compound-treated cells, solutions of VEGF at 550 ng/mL or bFGF at 220 ng/mL for 50 ng/mL or 20 ng/mL final concentrations, respectively, are prepared since 10 μL of each will be added to the cells (110 μL final volume). At the appropriate time after adding the compounds, the growth factors are added. VEGF is added to one set of plates, while bFGF is added to another set of plates. For the growth factor control curves, the media on wells B4-G6 of plates 1 and 2 are replaced with media containing VEGF or bFGF at the varying concentrations (50-0 ng/mL). The cells are incubated at 37° C. for an additional 72 h.

At the completion of the 72 h incubation period, the medium is removed, and the cells are washed twice with PBS. After the second wash with PBS, the plates are tapped gently to remove excess PBS, and the cells are placed at −70° C. for at least 30 min. The cells are thawed and analyzed using the CyQuant fluorescent dye (Molecular Probes C-7026), following the manufacturer's recommendations. The plates are read on a Victor/Wallac 1420 workstation at 485 nm/530 nm (excitation/emission). Raw data are collected and analyzed using a 4-parameter fit equation in XLFit. IC$_{50}$ values are then determined.

Rat Corneal Neovascularization Micropocket Model

In Life Aspects: Female Sprague Dawley rats weighing approximately 250 g were randomized into one of five treatment groups. Pretreatment with the vehicle or compound was administered orally, 24 h prior to surgery and continued once a day for seven additional days. On the day of surgery, the rats were temporarily anesthetized in an Isofluorane gas chamber (delivering 2.5 liters/min oxygen+5% Isofluorane). An othoscope was then placed inside the mouth of the animal to visualize the vocal cords. A tip-blunted wire was advanced in between the vocal cords and used as a guide for the placement of an endotracheal Teflon tube (Small Parts Inc. TFE-standard Wall R-SWTT-18). A volume-controlled ventilator (Harvard Apparatus, Inc. Model 683) was connected to the endotracheal tube to deliver a mixture of oxygen and 3% Isofluorane. Upon achieving deep anesthesia, the whiskers were cut short and the eye areas and eyes gently washed with Betadine soap and rinsed with sterile saline. The corneas were irrigated with one to two drops of Proparacaine HCl ophthalmic topical anesthetic solution (0.5%) (Bausch and Lomb Pharmaceuticals, Tampa Fla.). The rat was then positioned under the dissecting microscope and the corneal surface brought into focus. A vertical incision was made on the midline of the cornea using a diamond blade knife. A pocket was created by using fine scissors to separate the connective tissue layers of the stroma, tunneling towards the limbus of the eye. The distance between the apex of the pocket and the limbus was approximately 1.5 mm. After the pocket had been made, the soaked nitrocellulose disk filter (Gelman Sciences, Ann Arbor Mich.) was inserted under the lip of the pocket. This surgical procedure was performed on both eyes. rHu-bFGF soaked disks were placed into the right eye, and the rHu-VEGF soaked disks were placed into the left eye. Vehicle soaked disks were placed in both eyes. The disk was pushed into position at the desired distance from the limbal vessels. Ophthalmic antibiotic ointment was applied to the eye to prevent drying and infection. After seven days, the rats were euthanized by CO$_2$ asphyxiation, and the eyes enucleated. The retinal hemisphere of the eye was windowed to facilitate fixation, and the eye placed into formalin overnight.

Post Mortem Aspects: After 24 h in fixative, the corneal region of interest was dissected out from the eye, using fine forceps and a razorblade. The retinal hemisphere was trimmed off and the lens extracted and discarded. The corneal dome was bisected and the superfluous cornea trimmed off. The iris, conjunctiva and associated limbal glands were then carefully teased away. Final cuts were made to generate a square 3×3 mm containing the disk, the limbus, and the entire zone of neovascularization.

Gross Image Recording: The corneal specimens were digitally photographed using a Sony CatsEye DKC5000 camera (A.G. Heinz, Irvine Calif.) mounted on a Nikon SMZ-U stereo microscope (A.G. Heinz). The corneas were submerged in distilled water and photographed via trans-illumination at approximately 5.0 diameters magnification.

Image analysis: Numerical endpoints were generated using digital micrographs collected from the whole mount corneas after trimming and were used for image analysis on the Metamorph image analysis system (Universal Imaging Corporation, West Chester Pa.). Three measurements were taken: Disk placement distance from the limbus, number of vessels intersecting a 2.0 mm perpendicular line at the midpoint of the disk placement distance, and percent blood vessel area of the diffusion determined by thresholding.

General Formulations:
0.1% BSA in PBS vehicle: 0.025 g of BSA was added to 25.0 mL of sterile 1× phosphate buffered saline, gently shaken until fully dissolved, and filtered at 0.2 µM. Individual 1.0 mL samples were aliquoted into 25 single-use vials, and stored at −20° C. until use. For the rHu-bFGF disks, a vial of this 0.1% BSA solution was allowed to thaw at RT. Once thawed, 10 µL of a 100 mM stock solution of DTT was added to the 1 ml BSA vial to yield a final concentration of 1 mM DTT in 0.1% BSA.

rHu-VEGF Dilutions: Prior to the disk implant surgery, 23.8 µL of the 0.1% BSA vehicle above was added to a 10 µg rHu-VEGF lyophilized vial yielding a final concentration of 10 µM.

rHu-bFGF: Stock concentration of 180 ng/µL: R&D rHu-bFGF: Added 139 µL of the appropriate vehicle above to the 25 µg vial lyophilized vial. 13.3 µL of the [180 ng/µL] stock vial and added 26.6 µL of vehicle to yield a final concentration of 3.75 µM concentration.

Nitro-cellulose disk preparation: The tip of a 20-gauge needle was cut off square and beveled with emery paper to create a punch. This tip was then used to cut out ≅0.5 mm diameter disks from a nitrocellulose filter paper sheet (Gelman Sciences). Prepared disks were then placed into Eppendorf microfuge tubes containing solutions of either 0.1% BSA in PBS vehicle, 10 µM rHu-VEGF (R&D Systems, Minneapolis, Minn.), or 3.75 µM rHu-bFGF (R&D Systems, Minneapolis, Minn.) and allowed to soak for 45-60 min before use. Each nitrocellulose filter disk absorbs approximately 0.1 µL of solution.

In the rat micropocket assay, compounds of the present invention will inhibit angiogenesis at a dose of less than 50 mg/kg/day.

Tumor Model

A431 cells (ATCC) are expanded in culture, harvested and injected subcutaneously into 5-8 week old female nude mice (CD1 nu/nu, Charles River Labs) (n=5-15). Subsequent administration of compound by oral gavage (10-200 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (Ora-Plus, pH 2.0) is the negative control. Compounds of the present invention will be active at doses less than 150 mpk.

Human glioma tumor cells (U87MG cells, ATCC) are expanded in culture, harvested and injected subcutaneously into 5-8 week old female nude mice (CD1 nu/nu, Charles River Labs) (n=10). Subsequent administration of compound by oral gavage or by IP (10-100 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (captisol, or the like) is the negative control. Compounds of the present invention will be active at doses less than 100 mpk.

LCK-Homogeneous Time Resolved Fluorescent (HTRF) Kinase Assay:

The LCK HTRF assay begins with LCK in the presence of ATP phosphorylating the biotinylated peptide Gastrin. The reaction incubates for 90 min. To quench the assay detection reagents are added which both stop the reaction by diluting out the enzyme and chelating the metals due to the presence of EDTA. Once the detection reagents are added the assay incubates for 30 min to allow for equilibration of the detection reagents.

The LCK HTRF assay is comprised of 10 µL of compound in 100% DMSO, 15 µL of ATP and biotinylated Gastrin, and 15 µL of LCK KD GST (225-509) for a final volume of 40 µL. The final concentration of gastrin is 1.2 µM. The final concentration of ATP is 0.5 µM (Km app=0.6 µM+/−0.1) and the final concentration of LCK is 250 µM. Buffer conditions are as follows: 50 mM HEPES pH 7.5, 50 mM NaCl, 20 mM MgCl, 5 mM MnCl, 2 mM DTT, 0.05% BSA.

The assay is quenched and stopped with 160 µL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.0004 mg/mL, and europilated anti-phosphotyrosine Ab (Eu-anti-PY) at a final conc of 0.025 nM.

The assay plate is read in either a Discovery or a RubyStar. The eu-anti-PY is excited at 320 nm and emits at 615 nm to excite the SA-APC, which in turn emits at 655 nm. The ratio of SA-APC at 655 nm (excited due to close proximity to the Eu-anti-PY because of phosphorylation of the peptide) to free Eu-anti-PY at 615 nm will give substrate phosphorylation.

Human Mixed Lymphocyte Reaction (huMLR):

The purpose of this assay is to test the potency of T cell activation inhibitors in an in vitro model of allogeneic T cell stimulation. Human peripheral blood lymphocytes (hPBL; $2 \times 10^5$/well) are incubated with mitomycin C-treated B lymphoblastoid cells (JY cell line; $1 \times 10^5$/well) as allogeneic stimulators in the presence or absence of dilutions of potential inhibitor compound in 96-well round-bottom tissue culture plates. These cultures are incubated at 37° C. in 5% $CO_2$ for 6 days total. The proliferative response of the hPBL is measured by $^3$H-thymidine incorporation overnight between days 5 and 6 after initiation of culture. Cells are harvested onto glass fiber filters and $^3$H-thymidine incorporation into DNA is analyzed by liquid scintillation counter.

Jurkat Proliferation/Survival Assay:

The purpose of this assay is to test the general anti-proliferative/cytotoxic effect of compounds on the Jurkat human T cell line. Jurkat cells ($1 \times 10^5$/well) are plated in 96-well flat-bottom tissue culture plates with or without compound dilutions and cultured for 72 h at 37° C. in 5% $CO_2$. Viable cell number is determined during the last 4 h of culture by adding 10 µL/well WST-1 dye. WST-1 dye conversion relies on active mitochondrial electron transport for reduction of the tetrazolium dye. The dye conversion is read by OD at 450-600 nm.

Anti-CD3/CD28-Induced T Cell IL-2 Secretion and Proliferation Assay:

The purpose of this assay is to test the potency of T cell receptor (TCR; CD3) and CD28 signaling pathway inhibitors in human T cells. T cells are purified from human peripheral blood lymphocytes (hPBL) and pre-incubated with or without compound prior to stimulation with a combination of an anti-CD3 and an anti-CD28 antibody in 96-well tissue culture plates ($1\times10^5$T cells/well). Cells are cultured for ~20 h at 37° C. in 5% $CO_2$, then secreted IL-2 in the supernatants is quantified by cytokine ELISA (Pierce/Endogen). The cells remaining in the wells are then pulsed with $^3$H-thymidine overnight to assess the T cell proliferative response. Cells are harvested onto glass fiber filters and 3H-thymidine incorporation into DNA is analyzed by liquid scintillation counter. For comparison purposes, phorbol myristic acid (PMA) and calcium ionophore can be used in combination to induce IL-2 secretion from purified T cells. Potential inhibitor compounds can be tested for inhibition of this response as described above for anti-CD3 and -CD28 antibodies.

Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. No. 6,630,500, U.S. Pat. No. 6,515,004, U.S. Pat. No. 6,713,485, U.S. Pat. No. 5,521,184, U.S. Pat. No. 5,770,599, U.S. Pat. No. 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089 and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTINT™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., US Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., US Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC: antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (WAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Formulations

Also embraced within this invention is a class of pharmaceutical compositions comprising the active compounds of Formula I-VII in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 100 mg/kg, or between about 0.01 and about 20 mg/kg, or between about 0.01 and about 10 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily, dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, EtOH, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes, which are obvious to one skilled in the art, are intended to be within the scope and nature of the invention, which are defined, in the appended claims.

From the foregoing description, one skilled in the art can easily ascertain the essential characteristics of this invention, and without departing from the spirit and scope thereof, can make various changes and modifications of the invention to adapt it to various usages and conditions.

No unacceptable toxological effects are expected when compounds of the present invention are administered in accordance with the present invention.

All mentioned references, patents, applications and publications, are hereby incorporated by reference in their entirety, as if here written.

We claim:

1. A compound of the following Formula I,

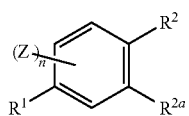

an enantiomer, a diastereomer, or a pharmaceutically acceptable salt thereof
wherein
j is one to six;
n and m are each independently zero to three;
p at each occurrence is independently zero to six;
q is zero to four;
t is zero, l is one or two;
$R^1$ is

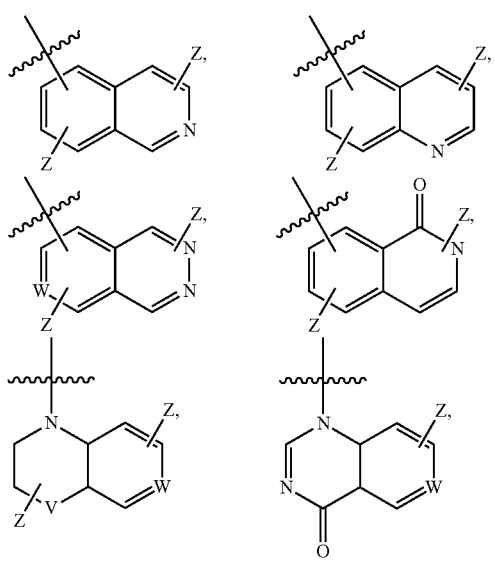

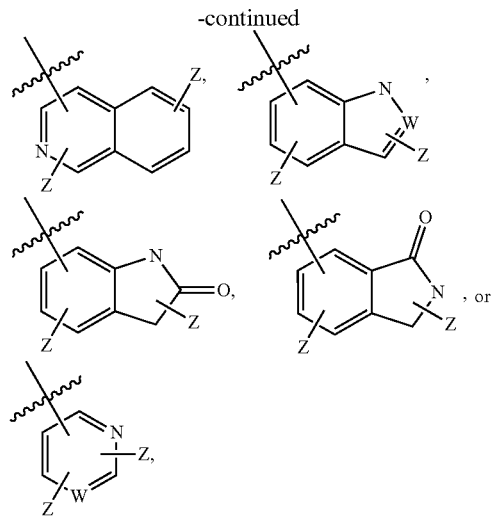

where W is C or N; and
V is C, O or N;
$R^2$ and $R^{2a}$ together with the respective phenyl ring carbon atoms to which they are each bonded combine to form one of the following ring systems:

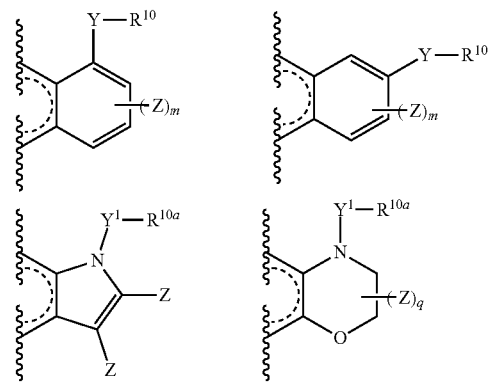

-continued

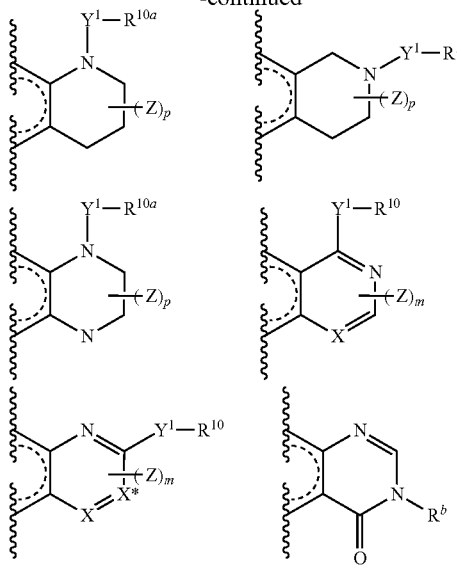

X is C or N;

X* is C or N provided X* is not N when X is N;

Y is selected from —$NR^b(CR^3R^4)_p$—, —$NR^bC(=O)(CR^3R^4)_p$—, —$NR^bC(=O)NR^b(CR^3R^4)_p$—, —$NR^bC(=O)NR^b(CR^3R^4)_p$—, —$NR^bC(=O)(CR^3R^4)_pO$—, —$NR^bC(=O)O(CR^3R^4)_p$—, —$NR^bC(=S)(CR^3R^4)_p$—O—, —$NR^bC(=S)$—$NR^b(CR^3R^4)_p$—, —$NR^bC(=S)$—$NR^b$—$C(=O)(CR^3R^4)_p$—, —$NR^bC(=NR^a)(CR^3R^4)_p$—, —$NR^bSO_2$—$(CR^3R^4)_p$—, —$OC(=O)(CR^3R^4)_p$—, —$O(CR^3R^4)_p$—, —$(CR^3R^4)_p$—$S(=O)_t$—, —$(CR^3R^4)_p$—, —$S(=O)_2NR^b(CR^3R^4)_p$—, —$S(=O)_t(CR^3R^4)_p$—, —$C(=O)(CR^3R^4)_p$—, —$C(=O)$—$O$—$(CR^3R^4)_p$—, —$C(=NR^a)NH(CR^3R^4)_p$—, —$C(=S)NH(CR^3R^4)_p$— and —$C(=O)NH(CR^3R^4)_p$—; wherein Y is in either direction;

$Y^1$ is selected from —$NR^b(CR^3R^4)_p$—, —$NR^bC(=O)(CR^3R^4)_p$—, —$NR^bC(=O)NR^b(CR^3R^4)_p$—, —$NR^bC(=O)O(CR^3R^4)_p$—, —$NR^bC(=S)(CR^3R^4)_p$—, —$NR^bC(=NR^a)(CR^3R^4)_p$—, —$NR^bSO_2$—$(CR^3R^4)_p$—, —$(CR^3R^4)_p$—$S(=O)_t$—, —$(CR^3R^4)_p$—, —$S(=O)_2NR^b(CR^3R^4)_p$—, —$S(=O)_t(CR^3R^4)_p$—, —$C(=O)(CR^3R^4)_p$—, —$C(=NR^a)NH(CR^3R^4)_p$—, —$C(=S)NH(CR^3R^4)_p$— and —$C(=O)NH(CR^3R^4)_p$—; wherein $Y^1$ is in either direction;

$R^a$ and $R^b$ is each independently selected from H, alkyl, heterocyclyl, aryl, arylalkyl, heterocyclylalkyl, cycloalkyl, cycloalkylalkyl, alkenyl, alkynyl, $R^5R^5N$—(C=O)—, and $R^5$—(=O)—; wherein each of $R^a$ and $R^b$ is optionally substituted;

$R^3$ and $R^4$ is each independently selected from H, alkyl, aryl, heterocyclyl, arylalkyl, heterocyclylalkyl, haloalkyl, cycloalkyl, cycloalkylalkyl, $R^6$ and alkyl substituted with $R^6$;

$R^5$ at each occurrence is independently selected from H, alkyl, cycloalkyl, haloalkyl, arylalkyl, heteroarylalkyl, heterocycloalkyl, cycloalkylalkyl, aryl, heteroaryl, heterocyclyl, alkenyl, and alkynyl;

$R^6$ is selected from cyano, —$SR^9$, halo, —$SO_2R^9$, —$C(=O)R^9$, —$SO_2NR^9R^5$, —$NR^5C(=O)OR^9$, —$NR^5C(=O)NR^5R^9$, —$NR^5C(=O)R^9$, —$CO_2R^9$, —$C(=O)NR^9R^5$ and —$NR^9R^5$;

$R^7$, $R^{7a}$ and $R^8$ are independently H, alkyl, cycloalkyl, haloalkyl, arylalkyl, heteroarylalkyl, heterocycloalkyl, cycloalkylalkyl, aryl, heteroaryl, heterocyclyl, alkenyl, and alkynyl;

or $R^7$ and $R^8$ together with the nitrogen atom to which they are bonded combine to form a 5-10 membered heterocyclo or heteroaryl ring, either of which may be optionally substituted with 1 to 4 Z groups;

$R^9$ at each occurrence is independently
i) H; or
ii) alkyl, cycloalkyl, haloalkyl, arylalkyl, heteroarylalkyl, heterocycloalkyl, cycloalkylalkyl, aryl, or heteroaryl any of which may be optionally substituted with 1 or more Z groups;

$R^{10}$ and $R^{10a}$ are independently
i) H; or
ii) aryl, heteroaryl, heterocyclyl, cycloalkyl, cycloalkenyl, alkyl, alkenyl or alkynyl any of which may be optionally substituted with one or more Z groups;

Z at each occurrence is independently selected from independently selected from cyano, hydroxy, halogen, alkyl, haloalkyl, oxo, amino, —$NR^{7a}$-(alkyl)-$NR^7R^8$, —$NR^{7a}$-(alkyl)-$OR^9$, —$N(C=O)$—$NR^7R^8$, —$C(=O)NR^7R^8$.

2. A compound of claim 1 or a pharmaceutically acceptable salt thereof wherein Y is —$NR^b(CR^3R^4)_p$—, $NR^bC(=O)(CR^3R^4)_p$—, $NR^bC(=O)NR^b(CR^3R^4)_p$—, —$(CR^3R^4)_p$—, —$C(=O)(CR^3R^4)_p$—, —$C(=O)NH(CR^3R^4)_p$—, —$C(=O)$—$O$—$(CR^3R^4)_p$—, or —$NR^bC(=S)$—$NR^b(CR^3R^4)_p$—.

3. A compound of claim 1 or a pharmaceutically acceptable salt thereof wherein $R^{10}$ is phenyl, thiazolyl, or thienyl, any of which may be optionally substituted with one or more Z groups.

4. A compound of claim 1 or a pharmaceutically acceptable salt thereof wherein $R^1$ is

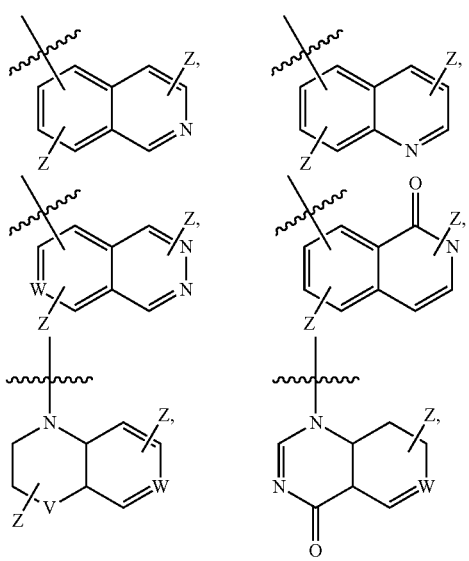

-continued

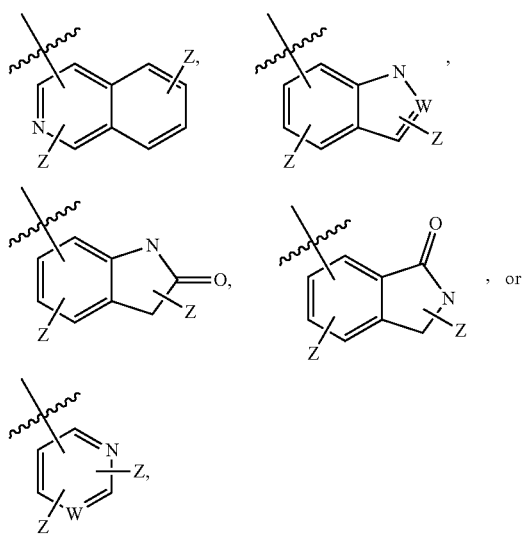

where W is C or N; and
V is C, O or N.

5. A compound of claim 1 or a pharmaceutically acceptable salt thereof wherein $R^1$ is

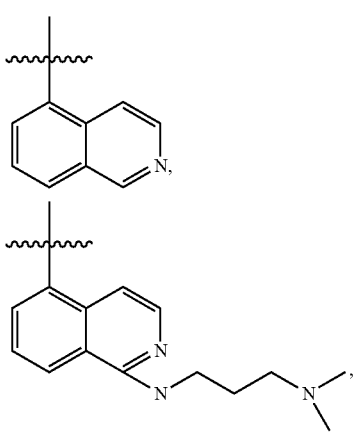

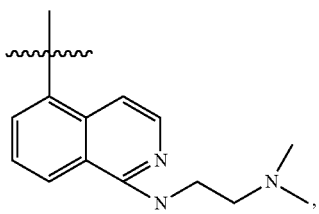

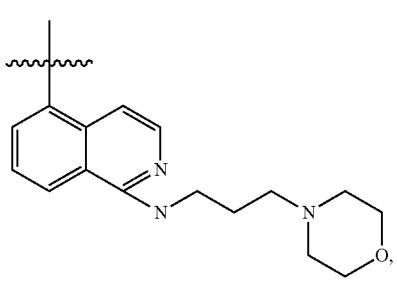

-continued

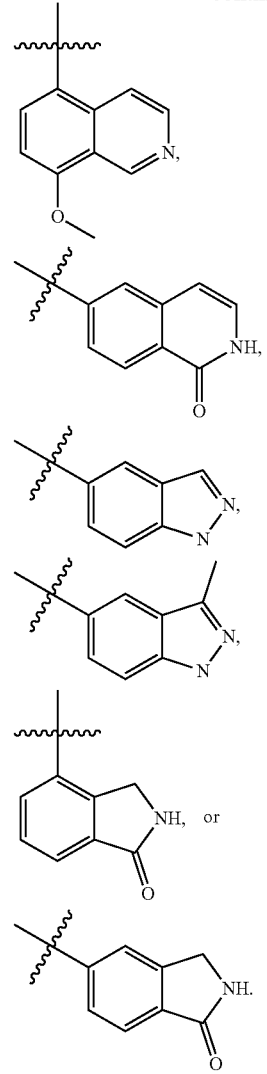

6. A compound of claim 1 or a pharmaceutically acceptable salt thereof having the structure of Formula III

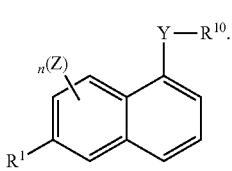

7. A compound of claim 6 or a pharmaceutically acceptable salt thereof wherein Y is —$NR^b(CR^3R^4)_p$—, —$NR^bC(=O)(CR^3R^4)_p$—, —$NR^bC(=O)NR^b(CR^3R^4)_p$—, —$(CR^3R^4)_p$—, —$C(=O)(CR^3R^4)_p$—, —$C(=O)NH(CR^3R^4)_p$—, —$C(=O)$—$O$—$(CR^3R^4)_p$—, or —$NR^bC(=S)$—$NR^b(CR^3R^4)_p$—.

8. A compound of claim 6 or a pharmaceutically acceptable salt thereof wherein $R^{10}$ is phenyl, thiazolyl, or thienyl, any of which may be optionally substituted with one or more Z groups.

9. A compound of claim 6 or a pharmaceutically acceptable salt thereof wherein $R^1$ is

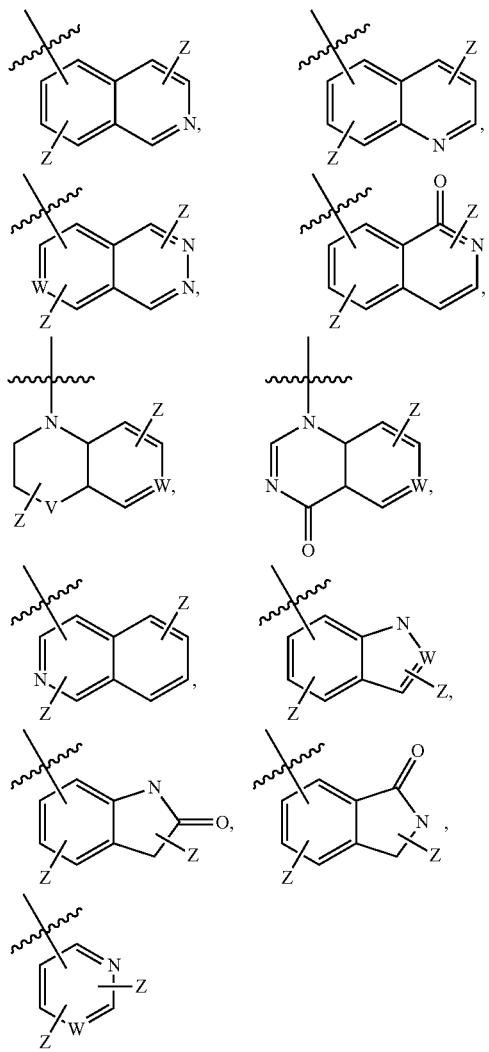

where W is C or N; and
V is C, O or N.

10. A compound of claim 6 wherein $R^1$ or a pharmaceutically acceptable salt thereof is

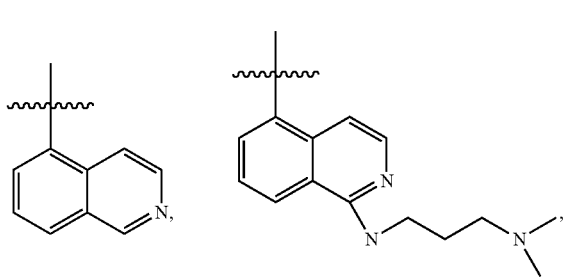

-continued

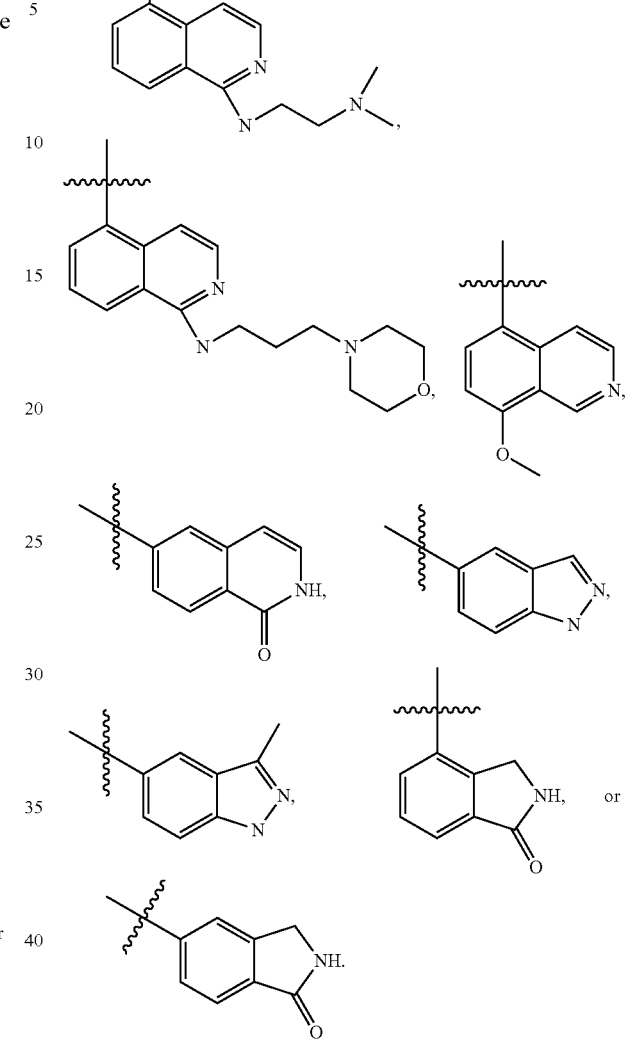

11. A compound of claim 1 or a pharmaceutically acceptable salt thereof having the structure of Formula IV

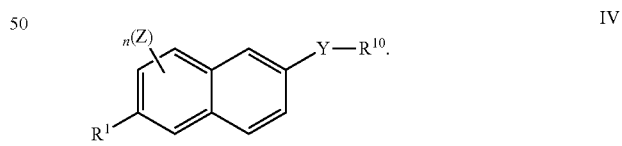

12. A compound of claim 11 or a pharmaceutically acceptable salt thereof wherein Y is —$NR^b(CR^3R^4)_p$—, —$NR^bC(=O)(CR^3R^4)_p$—, —$NR^bC(=O)NR^b(CR^3R^4)_p$—, —$(CR^3R^4)_p$—, —$C(=O)(CR^3R^4)_p$—, —C(=O)NH(CR$^3$R$^4$)$_p$—, —C(=O)—O—(CR$^3$R$^4$)$_p$—, or —NR$^b$C(=S)—NR$^b$(CR$^3$R$^4$)$_p$—.

13. A compound of claim 11 or a pharmaceutically acceptable salt thereof wherein R$^{10}$ is phenyl, thiazolyl, or thienyl, any of which may be optionally substituted with one or more Z groups.

14. A compound of claim 11 or a pharmaceutically acceptable salt thereof wherein R$^1$ is

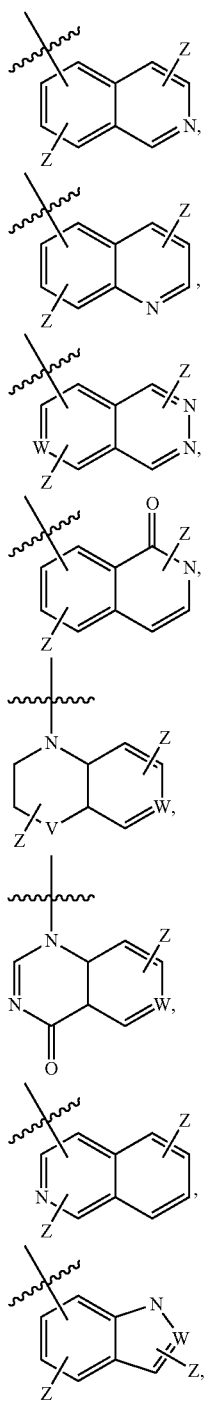

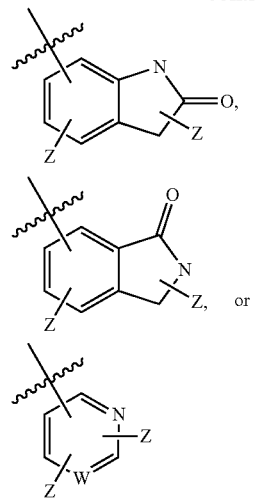

where W is C or N; and

V is C, O or N.

15. A compound of claim 11 or a pharmaceutically acceptable salt thereof wherein R$^1$ is

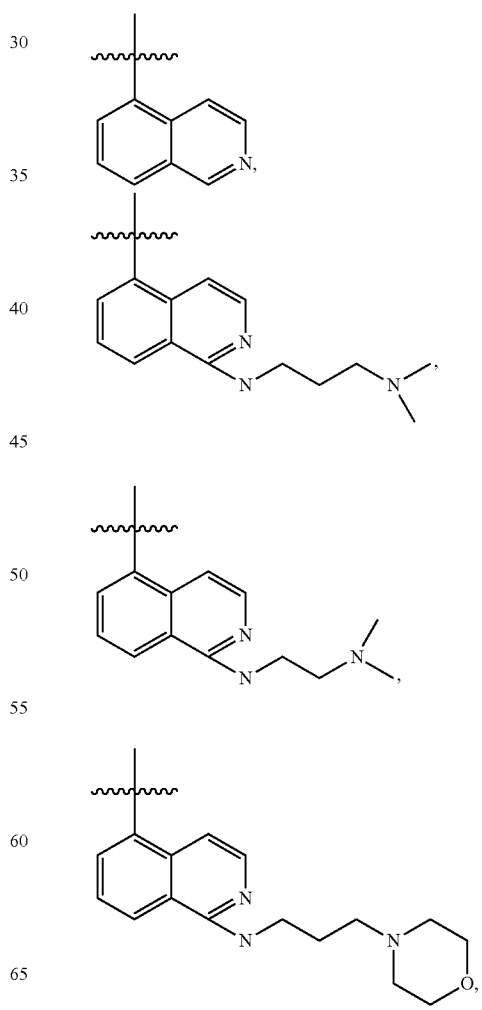

-continued

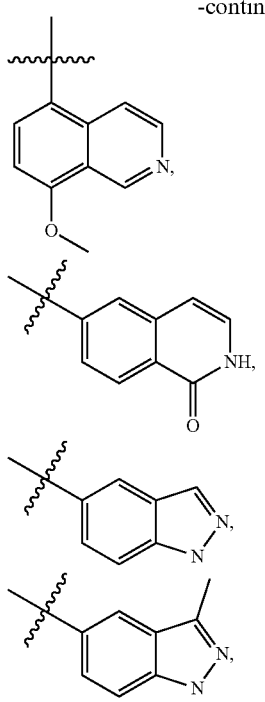

-continued

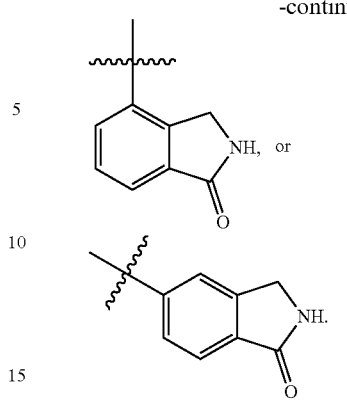

16. A pharmaceutical composition comprising a pharmaceutically-acceptable carrier and a compound of claim 1.

17. A method of treating cancer, wherein cancer is a gastric cancer or glioma, in a subject, said method comprising administering an effective amount of a compound of claim 1.

18. The method of claim 17 comprising a combination with a compound selected from antibiotic-type agents, alkylating agents, antimetabolite agents, hormonal agents, immunological agents, interferon-type agents and miscellaneous agents.

* * * * *